(12) United States Patent
Mercep et al.

(10) Patent No.: US 7,157,433 B2
(45) Date of Patent: *Jan. 2, 2007

(54) COMPOUNDS, COMPOSITIONS AS CARRIERS FOR STEROID/NONSTEROID ANTI-INFLAMMATORY; ANTIENOPLASTIC AND ANTIVIRAL ACTIVE MOLECULES

(75) Inventors: Mladen Mercep, Zagreb (HR); Milan Mesic, Zagreb (HR); Linda Tomaskovic, Zagreb (HR); Stribor Markovic, Zagreb (HR)

(73) Assignee: GlaxoSmithKline istrazivacki centar Zagreb, Zageb (HR)

( * ) Notice: Subject to any disclaimer, the term of this patent is extended or adjusted under 35 U.S.C. 154(b) by 0 days.

This patent is subject to a terminal disclaimer.

(21) Appl. No.: 10/616,046

(22) Filed: Jul. 8, 2003

(65) Prior Publication Data

US 2004/0077612 A1    Apr. 22, 2004

Related U.S. Application Data

(60) Provisional application No. 60/395,190, filed on Jul. 8, 2002.

(51) Int. Cl.
*A61K 31/70* (2006.01)
*C07H 17/08* (2006.01)

(52) U.S. Cl. .......................... 514/29; 514/8; 530/322; 536/7.4

(58) Field of Classification Search ................ 536/7.2, 536/7.3, 7.4; 530/322; 514/8, 29
See application file for complete search history.

(56) References Cited

U.S. PATENT DOCUMENTS

| | | | |
|---|---|---|---|
| 4,474,768 A | 10/1984 | Bright | |
| 4,710,495 A | 12/1987 | Bodor | |
| 5,004,731 A | 4/1991 | Philippe et al. | |
| 5,747,467 A | 5/1998 | Agouridas et al. | |
| 6,127,355 A | 10/2000 | Greenwald et al. | |
| 6,228,346 B1 | 5/2001 | Zhang et al. | |
| 6,273,086 B1 | 8/2001 | Ohki et al. | |
| 6,297,260 B1 | 10/2001 | Bandarage et al. | |
| 6,402,733 B1 | 6/2002 | Daugherty | |
| 6,566,509 B1 * | 5/2003 | Griffin et al. | 536/7.4 |
| 2001/0006962 A1 | 7/2001 | Myhren et al. | |
| 2004/0005641 A1 | 1/2004 | Burnet et al. | |
| 2004/0033969 A1 | 2/2004 | Burnet et al. | |
| 2004/0087517 A1 | 5/2004 | Burnet et al. | |
| 2004/0186063 A1 | 9/2004 | Gutke et al. | |

FOREIGN PATENT DOCUMENTS

| | | |
|---|---|---|
| EP | 0283055 | 8/1990 |
| EP | 0771564 | 5/1997 |
| EP | 0775489 | 5/1997 |
| EP | 0 283 055 | 9/1998 |
| EP | 00680967 | 10/1998 |
| EP | 0 895 999 | 2/1999 |
| EP | 0984019 | 3/2000 |
| EP | 0984019 A1 | 3/2000 |
| EP | 1 046 394 | 10/2000 |
| GB | 2 327 084 | 1/1999 |
| WO | WO 94/13690 | 6/1992 |
| WO | WO 92/13872 | 8/1992 |
| WO | WO 92/13873 | 8/1992 |
| WO | WO 94/14834 | 7/1994 |
| WO | WO 97/41255 | 11/1997 |
| WO | WO-97/41255 | 11/1997 |
| WO | WO 98/56801 | 12/1998 |
| WO | WO-99/28308 | 6/1999 |
| WO | WO 99/51616 | 10/1999 |
| WO | WO-99/64040 | 12/1999 |
| WO | WO 00/42055 | 7/2000 |
| WO | WO-00/64882 | 11/2000 |
| WO | WO-02/15700 | 2/2002 |
| WO | WO-02/055531 | 7/2002 |
| WO | WO-03/070173 A2 | 8/2003 |
| WO | WO-03/070174 A2 | 8/2003 |
| WO | WO-03/070254 | 8/2003 |

OTHER PUBLICATIONS

Burnet et al., "Conjugates of biologically active compounds, methods for their preparation and use, formulation, and pharmaceutical applications thereof," U.S. Appl. No. 60/357,789, filed Feb. 15, 2002.

Brandt-Rauf et al., "Fluorescent Assay For Estimating the Binding of Erythromycin Derivatives to Ribosomes," Antimicrobial Agents and Chemotherapy, American Society for Microbiology, Washington, D.C., 14(1):88-94. (1978).

(Continued)

*Primary Examiner*—Elli Peselev
(74) *Attorney, Agent, or Firm*—Darby & Darby

(57) ABSTRACT

The present invention relates (a) to new compounds represented by Formula I:

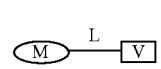

wherein M represents a macrolide subunit (macrolide moiety) derived from macrolide possessing the property of accumulation in inflammatory cells, V represents an anti-inflammatory steroid or nonsteroid subunit, or an antineoplastic or antiviral subunit and L represents a linking group covalently linking M and V; (b) to their pharmacologically acceptable salts, prodrugs and solvates, (c) to processes and intermediates for their preparation, and (d) to their use in the treatment of inflammatory/neoplastic/viral diseases and conditions in humans and animals.

64 Claims, No Drawings

OTHER PUBLICATIONS

Gladue R. P. et al.,"In Vitro and In Vivo Uptake of Azithromycin (CP-62,993) by Phagocytic Cells: Possible Mechanism of Delivery and Release at Sites of Infection," *Antimicrob. Agents and Chemother.*, 33. 1989, 277-282.

Olsen K. M. et al., "Intrapulmonary Pharmacokinetics of Zithromycin in Healthy Volunteers Given Five Oral Doses," *Antimicrob. Agents and Chemother.*,40, 1996, 2582-2585.

Mikasa, K. et al., "The anti-inflammatory effect of erythromycin in zymosan-induced peritonitis of mice,"*J. Antimicrob. Chemother.*, 30, 1992, 339-348.

"Discussion, Genomic organization of axolotl 1g genes," *J. Immunol.*, 159, 1997, 3395-4005.

Takizawa, H. et al., "Erythromycin Modulates IL-8 Expression in Normal and Inflamed Human Bronchial Epithelial Cells," *Am. J. Respir. Crit. Care Med.*, 156, 1997, 266-271.

Labro, M.T., "Anti-inflammatory activity of macrolides: a new therapeutic potential?" *J. Antimicrob. Chemother.* 41, 1998, 37-46.

Cazzola, M., et al., "Potential role of macrolides in the treatment of asthma," *Mondaldi Arch. Chest Dis.*, 55, 2000, 231-236.

Avila, P.C. et al., "Macrolides, asthma, inflammation, and infection," *Ann. Allergy Asthma Immunol*, 84, 2000, 565-568.

Amayasu, H. et al., "Clarithromycin suppresses bronchial hyperresponsiveness associated with eosinophilic inflammation in patients with asthma," *Ann. Allergy, Asthma & Immunol*, 84, 2000, 594-598.

Shoji, T. et al., "Anti-inflammatory effect of roxithromycin in patients with aspirin-intolerant asthma," *Clin. Exp. Allergy*, 29, 999, 950-956.

Griffith, E.C., et al., "Yeast Three-Hybrid System for Detecting Ligand-Receptor Interactions," *Methods in Enzymology*, 328m 2000, 89-110.

Denis A. et al., "Synthesis and Antibacterial Activity of HMR 36K47 , A New Ketolide Highly Potent Against Erythromycin-Resistant and Susceptible Pathogens," *Bioorg. & Med. Chem. Lett*, 9, 1999, 3075-3080.

Agouridas C. et al., "Synthesis and Antibacterial Activity of Ketolides (6-O-Methyl-3-oxoerythromycin Derivatives): A New Class of Antibacterials Highly Potent against Macrolide-Resistant and -Susceptible Respiratory Pathogens," *J. Med. Chem.*, 41, 1998, 4080-4100.

Sun, Or Y. et al. *J. Med. Chem.* 2000, 43, 1045-1049.

McFarland, J. W. et al., "Repromicin Derivatives with Potent Antibacterial Activity against *Pasteurella multocida*," *J. Med. Chem.*, 50, 1997, 1041-1045.

Denis A. et al., Synthesis of 6-O-Methyl-Azithromycin and Its Ketolide Analogue via Beckmann Rearrangement of 9(E)-6-O-Methyl-Erythromycin Oxime, *Bioorg.& Med. Chem. Lett.*, 8, 1998, 2427-2432.

Lartey et al., "Synthesis of 4"-Deoxy Motilides: Identification of a Potent and Orally Active Prokinetic Drug Candidate, *J. Med. Chem.*, 38, 1998, 1793-1798.

Kirst, H.A. et al., "34. Metabolism of macrolides," Bryskier, A. J. et al., Ed. *Macrolides, Chemistry, Pharmacology and Clinical Use*; Bryskier, Amette Blackwell: Paris, 1993; pp. 485-491.

Ma, Z. et al., "Discovery and Development of Ketolides as a New Generation of Macrolide Antimicrobial Agents," *Current Medicinal Chemistry—Anti-Infective Agents*, 1, 2002, 15-34.

Pascual A. et al., "Uptake and intracellular activity of ketolide HMR 3647 in human phagocytic and non-phagocytic cells,"*Clin. Microbiol. Infect.*, 7, 2001, 65-69.

Hand, W. L. et al., "Characteristics and mechanisms of azithromycin accumulation and efflux in human polymorphonuclear leukocytes," *Int. J. Antimicrob. Agents*, 18, 2001, 419-425.

Amsden, G. W., "Advanced-generation macrolides: tissue-directed antibiotics," *Int. J. Antimicrob. Agents*, 18, 2001, 11-15.

Johnson, J. D. et al., "Antibiotic uptake by alveolar macrophages,"*J. Lab. Clin. Med.*, 95, 1980, 429-439.

Wildfeuer, A. et al., "Uptake of Azithromycin by Various Cells and Its Intracellular Activity under in Vivo Conditions," *Antimicrob. Agents Chemother.*, 40, 1996, 75-79.

Scorneaux, B. et al., "Intracellular Accumulation, Subcellular Distribution, and Efflux of Tilmicosin in Chicken Phagocytes," *Poult. Sci.*, 77, 1998, 1510-1521.

Mtairag, E. M. et al., "Investigation of dirithromycin and erythromyclamine uptake by human neutrophils *in vitro*," *J. Antimicrob. Chemother.* 33, 1994, 523-536.

Anderson R. et al., "An in-vitro evaluation of the cellular uptake and intraphagocytic bioactivity of clarithromycin (A-56268, TE-031), a new macrolide antimicrobial agent," *J. Antimicrob. Chemother.*, 22, 1988, 923-933.

Tasaka, Y. et al., "Rokitamycin Uptake by Alveolar Macrophages," *Jpn. J. Antibiot.* 41, 1988, 836-840.

Harf, R. et al., "Spiramycin uptake by alveolar macrophages," *J. Antimicrob. Chemother.*, 22, 1988, 135-140.

Suzuki, T. et al., "General and facile method for determination of configuration of steroid-17-yl-methyl glycolates at C-20 based on kinetic examination," *Chem. Soc.*, Perkin Trans. 1, 1998, 3831-3836.

McLean, H.M. et al., "Novel Fluorinated Antiinflammatory Steroid with Reduced Side Effects: Methyl 9α-Fluoroprednisolone-16-carboxylate," *J. Pharm. Sci.* 1994, 83, 476-480.

Little, R.J. et al., "Soft Drugs Based on Hydrocortisone: The Inactive Metabolite Approach and Its Application to Steroidal Antiinflammatory Agents," *Pharm. Res.*, 16, 1999, 961-967.

Kertesz, D.J. et al., "Thiol Esters from Steroid 17β-Carboxylic Acids: Carboxylate Activation and Internal Participation by 17α-Acylates," *J. Org. Chem.*, 51, 1986, 2315-2328.

Phillipps, G. et al., "Synthesis and Structure—Activity Relationships in a Series of Antiinflammatory Corticosteroid Analogues, Halomethyl Androstane-17β-carbothioates and 17β-carboselenoates," *J. Med. Chem.* 37, 1994, 3717-3729.

Bright, G.M. et al., "Synthesis, In Vitro and In Vivo Activity of Novel 9-Deoxo-9a-AZA-9a-Homoerythromycin A Derivatives; A new Class of Macrolide Antibiotics, the Azalides" *J. Antibiot.*, 41, 1998, 1029-1047.

Costa, A.M. et al., "Hybrids of macrolides and nucleobases or nucleosides," *Tetrahedron Letters*, 41, 2000, 3371-3375.

Newman, S.P. et al., "Evaluation of jet nebulisers for use with gentamicin solution," *Thorax*, 40, 1985, 671-676.

Berenberg, M.J. et al., "Comparison of Metered-Dose Inhaler Attached to an Aerochamber with an Updraft Nebulizer for the Administration of Metaproterenol in Hospitalized Patients," *J. Asthma USA*, 22, 1985, 87-92.

Warner, Timothy D. et al., "Nonsteroid drug selectivities for cyclo-oxygenase-1 rather than cyclo-oxygenase-2 are associated with human gastrointestinal toxicity: A full in vitro analysis," *Proc. Natl. Acad. Sci. USA* 96. Jun. 1999, 7563-7568.

Luong, Brigitte T. et al., "Treatment Options for Rheumatoic Arthirtis: Celecoxib, Leflunomide, Etanercept, and Infliximab," *The Annals of Pharmacotherapy* 34, 2000, 743-760.

Taketo, Makoto M., "Cyclooxygenase-2 Inhibitors in Tumorigenesis (Part 11)," *Journal of the National Cancer Institute* 90, 21, 1998, 1609-1620.

Fournier, David B. et al., "COX-2 and Colon Cancer: Potential Targets for Chemoprevention," *Journal of Cellular Biochemistry Supplement* 34, 2000, 34-97.

Carswell, E.A. et al., "An endotoxin-induced serum factor that causes necrosis of tumors," *Proc. Nat. Acad. Sci. USA* 72, 9, 1975, 3666-3670.

Elliott, Michael J. et al., "Randomised double-blind comparison of chimeric monoclonal antibody to tumour necrosis factor α (cA2) versus placebo in rheumatoid arthritis," *The Lancet* 344, 1994, 1005-1110.

Mori, Lucia et al., "Attenuation of Collagen-Induced Arthritis in 55-kDa TNF Receptor Type 1 (TNFR1)-IgG1-Treated and TNFR1-Deficient Mice," *Journal of Immunology*, 1996, 3178-3182.

Pfeffer, Klaus et al., "Mice Deficient for the 55 kd Tumor Necrosis Factor Receptor Are Resistant to Endotoxic Shock, yet Succomb to L. monocytogenes Infection," *Cell* 73, 1993, 457-467.

Georgopoulos, Spiros et al., "Transmembrane TNF Is Sufficient To Induce Localized Tissue Toxicity and Chronic Inflammatory Arthritis in Transgenic Mice," *Journal of Inflammation* 46, 1996, 86-97.

Keffer, Jeanne et al., "Transgenic mice expressing human tumour necrosis factor: a predictive genetic model of arthritis," *The EMBO Journal* 10, 13, 1991, 4025-4031.

Van Assche, Gert et al., "Anti-TNF agents in Crohn's disease,"*Exp. Opin. Invest. Drugs,* 2000, 103-111.

Romo, Daniel et al., "Total Synthesis and Immunosuppresive Activity of (-)-Pateamine A and Related Compounds: Implementation of a β-Lactam-Based Macrocyclization," *J. Am. Chem. Soc.* 120, 1998, 12237-12254.

Huang, Chun-Ming et al., "Targeting delivery of paclitaxel into tumor cells via somatostatin receptor endocytosis," *Chemistry & Biology* 7, 9, 2000, 453-461.

Pandor, Mark W. et al., "Photochemical Control of the Infectivity of Adenoviral Vectors Using a Novel Photocleavable Biotinylation Reagent," *Chemistry & Biology* 9, 2002, 567-573.

Colliet, H.O.J. et al., "The Abdominal Constriction Response and Its Suppression by Analgesic Drugs in the Mous ," *Br. J. Pharmac. Themother.* 32, 1968, 295-310.

Fukawa, Kazunaga et al., "A Method for Evaluating Analgesic Agents in Rats," *Journal of Pharmacological Methods* 4, 1980, 251-259.

Schweizer, A. et al., "Combined automated writhing/motility test for testing analgesics," *Agents and Actions* 23, 1/2, 1988, 29-31.

\* cited by examiner

COMPOUNDS, COMPOSITIONS AS CARRIERS FOR STEROID/NONSTEROID ANTI-INFLAMMATORY; ANTIENOPLASTIC AND ANTIVIRAL ACTIVE MOLECULES

PRIORITY CLAIM

This application claims priority to U.S. Provisional Application 60/395,190 filed Jul. 8, 2002 herein incorporated by reference in its entirety.

SUMMARY OF THE INVENTION

The present invention relates (a) to new compounds represented by the structure I:

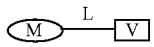

I wherein M represents a macrolide subunit possessing the property of accumulation in inflammatory cells, V represents an antiinflammatory compound, either steroid or non steroid subunit, or an antineoplastic agent subunit, or an antiviral compound subunit; and L represents a linking group covalently linking M and V, (b) to the pharmacologically acceptable salts, prodrugs and solvates, (c) to processes and intermediates for the preparation of such compounds, and (d) to their use in the treatment of inflammatory, neoplastic and viral diseases and conditions in humans and animals. Such compounds can act as prodrugs, transporting the compound into the target cell and releasing it inside such target cell in higher concentration than could be normally achieved by the compound alone or they can be active in their hybrid form, as administered. These compounds and their foregoing uses are therefore responsive to the technical problem of increasing the effectiveness and/or efficiency and/or decreasing side effects of one or more of the foregoing active ingredients by delivering them in hybrid form preferentially to target cells or to the vicinity of target cells.

BACKGROUND OF THE INVENTION

Anti-inflammatory medicaments could be classified into those of steroid and of nonsteroidal type. Steroid anti-inflammatory compounds are still the most effective ones in the treatment of inflammatory diseases and conditions such as: asthma, chronic obstructive pulmonary disease, inflammatory nasal diseases such as allergic rhinitis, nasal polyps, intestinal diseases such as Crohn's disease, colitis, ulcerative colitis, dermatological inflammations such as eczema, psoriasis, allergic dermatitis, neurodermatitis, pruritus, conjunctivitis, autoimmune diseases such as rheumatoid arthritis, and inhibition of transplantation immunity. Moreover, steroids are used as adjunct chemotherapeutic agents in treating various malignancies, including leukemias, lymphomas, myelomas, and other malignancies of the hematopoietic system. In addition to excellent potency and effectiveness, medicaments of this type also possess numerous unfavourable side-effects, e.g., on carbohydrate metabolism, calcium resorption, secretion of endogenous corticosteroids as well as on the physiological functions of the pituitary gland, adrenal cortex and thymus. Recently developed steroids are highly effective against inflammatory conditions and processes since they inhibit many inflammation mediators, whereas their systemic side-effects are diminished. Patent applications WO 94/13690, WO 94/14834, WO 92/13873 and WO 92/13872 describe the so-called "soft" steroids or hydrolysable corticosteroids designed for topical application on the inflammation site, whereas their systemic side-effects are diminished due to instability of "soft" steroids in the serum, wherein the active steroid very rapidly hydrolyses into the inactive form. An ideal steroid, however, without unfavourable effects in a long-term and continuous treatment as required for the control of diseases such as asthma or Crohn's disease has yet to be found. Thus there is an acute need for steroids with an improved therapeutic profile, and/or fewer or milder side effects.

Nonsteroid anti-inflammatory medicaments having different mechanisms of action act on particular inflammation mediators, thus providing a therapeutic effect. Due to differences not only in mechanisms of action but also in the particular inflammation mediators inhibited, the steroid and nonsteroid medicaments possess different profiles of anti-inflammation effects, hence certain medicaments may be more suitable than others for particular conditions. Moreover, most nonsteroid anti-inflammatory medicaments are not absolutely specific and their use is accompanied by unfavourable side-effects when used in greater dosages or over long periods of time. It is known that many nonsteroid anti-inflammatory medicaments act as inhibitors of endogenous COX-1 enzyme, which is very important in maintaining the integrity of the gastric mucosa. Thus, the use of these medicaments often causes injuries of the gastric mucosa and even bleeding. ( Warner T. D. *Proc. Natl. Acad. Sci. =1 U.S.A.* 1999, 96, 7563–7568.) Therefore, agents that selectively inhibit COX-2 but not COX-1 are preferable for treatment of inflammatory diseases Additionally, some anti-inflammatory compounds (such as theophylline) are known to have a very narrow therapeutic index, which limits their usage.

Recently, the nonsteroidal antiinflammatory drug celecoxib that specifically blocks COX-2 has been approved by the FDA for use in the treatment of rheumatoid arthritis (Luong et al. *Ann. Pharmacother.* 2000, 34, 743–760). COX-2 is also expressed in many cancers and precancerous lesions, and there is mounting evidence that selective COX-2 inhibitors may be useful for treating and preventing colorectal and other cancers (Taketo, M. M., *J. Natl. Cancer Inst.* 1998, 90, 1609–1620, Fournier et. al. *J. Cell Biochem. Suppl.* 2000, 34, 97–102).

In 1975, TNF-α was defined as an endotoxin-induced serum factor causing tumor necrosis in vitro and in vivo (Carswell E. A. et al. *Proc. Natl. Acad. Sci. U.S.A.* 1975, 72, 3666–3670). In addition to antitumor activity, TNF-α has several other biologic activities, which are important in homeostasis as well as in pathophysiological conditions. The main sources of TNF-α are monocytes-macrophages, T-lymphocytes and mast cells.

The finding that anti-TNF-α antibodies (cA2) are effective in the treatment of patients suffering from rheumatoid arthritis (RA) (Elliot M. et al. *Lancet* 1994, 344, 1105–1110) intensified the interest to find new TNF-α inhibitors as possible potent medicaments for RA. Rheumatoid arthritis is an autoimmune chronic inflammatory disease characterized by irreversible pathological changes of the joints. In addition to RA, TNF-α antagonists are also applicable to several other pathological conditions and diseases such as spondylitis, osteoarthritis, gout and other arthritic conditions, sepsis, septic shock, toxic shock syndrome, atopic dermatitis, contact dermatitis, psoriasis, glomerulonephritis, lupus erhythematosus, scleroderma, asthma, cachexia, chronic obstructive lung disease, congestive heart failure, insulin resistance, lung fibrosis, multiple sclerosis, Crohn's disease, ulcerative colitis, viral infections and AIDS.

Two distinct retroviruses, human immunodeficiency virus (HIV) type-1 (HIV1) or type-2 (HIV-2), have been etiologically linked to the immunosuppressive disease, acquired immunodeficiency syndrome (AIDS). HIV seropositive individuals are initially asymptomatic but typically develop AIDS related complex (ARC) followed by AIDS. Affected individuals exhibit severe immunosuppression which predisposes them to debilitating and ultimately fatal opportunistic infections.

The disease AIDS is the consequence of HIV-1 or HIV-2 virus following its complex viral life cycle. The virion life cycle involves the virion attaching itself to the host human T-4 lymphocyte immune cell through the binding of a glycoprotein on the surface of the virion's protective coat with the CD4 glycoprotein on the lymphocyte cell. Once attached, the virion sheds its glycoprotein coat, penetrates into the membrane of the host cell, and uncoats its RNA. The virion enzyme, reverse transcriptase, directs the process of transcribing the RNA into single-stranded DNA. The viral RNA is degraded and a second DNA strand is created. The now double-stranded DNA is integrated into the human cell's genes and those genes are used for virus reproduction. RNA polymerase transcribes the integrated viral DNA into viral mRNA. The viral RNA is translated into the precursor gag-pol fusion polyprotein. The polyprotein is then cleaved by the HIV protease enzyme to yield the mature viral proteins. Thus, HIV protease is. responsible for regulating a cascade of cleavage events that lead to the virus particle's maturing into a virus that is capable of full infectivity.

The typical human immune system response, killing the invading virion, is taxed because the virus infects and kills the immune system's T cells. In addition, viral reverse transcriptase, the enzyme used in making a new. virion particle, is not very specific, and causes transcription mistakes that result in continually changed glycoproteins on the surface of the viral protective coat. This lack of specificity decreases the immune system's effectiveness because antibodies specifically produced against one glycoprotein may be useless against another, hence reducing the number of antibodies available to fight the virus. The virus continues to reproduce while the immune response system continues to weaken. In most cases, without therapeutic intervention, HIV causes the host's immune system to be debilitated, allowing opportunistic infections to set in. Without the administration of antiviral agents, immunomodulators, or both, death may result.

Hepatitis is an inflammation of the liver primarily caused by a virus and, less commonly, by certain medications or toxins (e.g. alcohol). The viral infection is often acquired through exposure to contaminated blood. Those most likely to contract the virus are intravenous drug users who share contaminated needles, although sexual contact with a person who has a form of Hepatitis can also spread the disease. In some instances, healthcare workers exposed to contaminated blood and persons who need repeated transfusions of blood have acquired a form of Hepatitis.

Three main types of viral Hepatitis have been identified, namely Hepatitis A, Hepatitis B and Hepatitis C, though at least four other viruses can cause hepatis. Hepatitis A is a highly infectious form of hepatitis and is the most common form of the disease. Hepatitis A is usually transmitted by contaminated food or water. The symptoms of hepatitis A often are similar to those of intestinal flu and a vast majority of persons with Hepatitis A recover completely.

Acute hepatitis B is potentially a more serious form of viral liver infection. Its symptoms are much the same as those of hepatitis A, but the symptoms are more severe and last longer. The primary initial symptoms of hepatitis A and hepatitis B include poor appetite, nausea, vomiting and fever. In later stages of hepatitis, the urine may become dark and persistent or recurring jaundice develops. In approximately 20% of cases of hepatitis cirrhosis (scarring of the liver) eventually develops. Cirrhosis as a result of hepatitis can be diagnosed through a blood test to evaluate liver function. Eventually, a liver affected by cirrhosis becomes tender as well. Hepatitis C, recognized as the major causative agent of non-A and non-B hepatitis, share common symptoms with hepatitis A and B. and patients develop chronic infections which can ultimately lead to liver cirrhosis.

Neoplastic diseases are a common cause of death, caused by autonomous, non-controlled division of cells. This division can be triggered by:

1. gene mutations caused by carcinogens
2. viruses
3. external signals which activate mitosis of certain cell type Neoplastic diseases are treated with various inhibitors of mitosis and cellular metabolism. However, specificity has been the major problem with anticancer agents. In the case of anticancer agents, the drug needs to distinguish between host cells that are cancerous and host cells that are not cancerous. The vast bulk of anticancer drugs are indiscriminate at this level. Typically anticancer agents have negative hematological effects (e.g., cessation of mitosis and disintegration of formed elements in marrow and lymphoid tissues), and immunosuppressive action (e.g., depressed cell counts), as well as a severe impact on epithelial tissues (e.g., intestinal mucosa), reproductive tissues (e.g., impairment of spermatogenesis), and the nervous system. P. Calabresi and B. A. Chabner, In: Goodman and Gilman The Pharmacological Basis of Therapeutics (Pergamon Press, 8th Edition) (pp. 1209–1216). Success with chemotherapeutics as anticancer agents has also been hampered by the phenomenon of multiple drug resistance, resistance to a wide range of structurally unrelated cytotoxic anticancer compounds. J. H. Gerlach et al., Cancer Surveys, 5:25–46 (1986). The underlying cause of progressive drug resistance may be due to a small population of drug-resistant cells within the tumor (e.g., mutant cells) at the time of diagnosis. J. H. Goldie and Andrew J. Coldman, Cancer Research, 44:3643–3653 (1984). Treating such a tumor with a single drug first results in a remission, where the tumor shrinks in size as a result of the killing of the predominant drug-sensitive cells. With the drug-sensitive cells gone, the remaining drug-resistant cells continue to multiply and eventually dominate the cell population of the tumor. Finally, the treatment of cancer has been hampered by the fact that there is considerable heterogeneity even within one type of cancer. Some cancers, for example, have the ability to invade tissues and display an aggressive course of growth characterized by metastases. These tumors generally are associated with a poor outcome for the patient. And yet, without a means of identifying such tumors and distinguishing such tumors from non-invasive cancer, the physician is at a loss to change and/or optimize therapy. What is needed is a specific anticancer approach that is reliable for a wide variety of tumor types, and particularly suitable for invasive tumors. Importantly, the treatment must be effective with minimal host toxicity. Thus it is necessary to overcame the potential of cells to decrease the intracellular amount of the active drug, to improve cellular targeting and/or to improve pharmacokinetic of antineoplastic drug.

Macrolides such as macrolide antibiotics accumulate within different cells of subjects administered such molecules, especially within phagocyte cells such as mononuclear peripheral blood cells, polymorphonuclear cells, peritoneal and alveolar macrophages as well as in the liquid surrounding the bronchoalveolar epithelium (Glaude R. P. et al., *Antimicrob. Agents Chemother.*, 33 1989, 277–282; Olsen K. M. et al., *Antimicrob. Agents Chemother.*, 40 1996, 2582–2585). Moreover, relatively weak inflammatory effects of some macrolides have been described. For example, the anti-inflammatory effect of erythromycin derivatives (*J. Antimicrob. Chemother.*, 41 1998 37–46; WO 00/42055) and azithromycin derivatives has recently been described (EP 0283055). Anti-inflammatory effects of some macrolides are also known from in vitro and in vivo studies in experimental animal models such as zimosane-induced peritonitis in mice (*J. Antimicrob. Chemother.*, 30 1992 339–348) and endotoxin-induced neutrophil accumulation in rat trachea (J. Immunol. 159 1997 3395–4005). The modulating effect of macrolides upon cytokines such as interleukin 8 (IL-8) (*Am. J. Respir. Crit. Care Med.* 156 1997 266–271) or interleukin 5 (IL-5) (EP 0775489 and EP 0771564) is known as well. Additionally, the favorable pharmacokinetic profile of macrolides could elevate tissue concentration of a compound e.g. in the liver, or increase white blood cells/plasma ratio (Girard A. E. et al., *Antimicrob. Agents Chemother.* 31 1987 1948–54; Widlfeuer A. et al, *Antimicrob. Agents Chemother.* 40 1996, 75–79).

In order to obtain compounds with improved/novel activity profile towards diseases where selective activity is needed several different active substances have been connected to macrolides with different types of linkers. A few examples of hybrids/conjugates/chimeras of erythromycin A derivatives and nucleobases (uracil and thymine) or thymidine-derived nucleosides have been reported. (Costa A. M. at al. *Tetrahedron Lett.* 41, 2000, 3371–3375). However, such constructs did not show activity/selectivity toward a desired target. Moreover, macrolide constructs where the linker would be of the peptide type not been reported.

The peptide linker introduced in our hybrid molecules as the linker enables them to act as prodrugs, releasing the V moiety by specific lysosomal cleavage within the target cell. Similar linkers have been described for other small molecules (in our case represented by hybrids of an anti-inflammatory, antineoplastic and antiviral compound) and a macromolecule or polymer (Duncan R. et al. in Robinson J. R. and Lee V. H. (eds.) *Controlled Drug Delivery:Fundamentals and Applications*, 2$^{nd}$ edition, 1987 581–607, Subr V. et al, *J. Controlled Rel.* 18 1992 123–132)

DETAILED DESCRIPTION OF THE INVENTION

Compounds represented by the Formula I differ from prior art compounds in that their structure permits them to accumulate in the organs targeted by and in cells effecting the inflammatory immune response or tumor or infection that requires treatment. It can also elevate the intracellular concentration of inhibitory compound within a tumor cell which makes them susceptible to irradication. Such action of the compounds of Formula I arises from the macrolide moiety M which has the pharmacokinetic property of accumulating in immune system cells, notably phagocytes. This enables the compounds of the Formula I to act predominantly if not exclusively at the inflammation or tumor or infection site, by "riding" the macrolide within the very inflammation cells recruited to the locus of inflammation, or infection or malignancy wherein the active ingredient can exert its activity. In such a manner, the systemic side-effects of steroid or nonsteroidal anti-inflammatory substances or anti-neoplastic agents or anti-viral compounds are significantly decreased or even eliminated. (It should be noted that steroids are used as adjunct therapy in the treatment of malignancy and the present invention also contemplates steroids for antineoplastic use.) After topical or systemic application, the hybrid molecules of the invention (and/or, if releasable, their constituent parts) rapidly accumulate at the inflammation site or in the tumor or infected cells or the vicinity thereof.

We have recently found that certain compounds within Formula I:

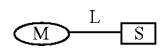

I exert an improved therapeutic effect in the treatment of inflammation diseases, disorders and conditions. The symbol M in the above structure represents a macrolide subunit possessing the property of accumulation in inflammatory cells, S represents an anti-inflammatory steroid subunit and L represents a linker covalently linking M and S. Our co-pending commonly owned International Patent application PCT/HR02/00001 (incorporated herein by reference in its entirety, describes compounds with the steroid subunit S linked via the chain L to position N/9a of 9-dihydro-9-deoxo-9a-aza-9a-homoerythromycin or to position C/3 of a des-cladinosyl azithromycin derivative or to position C/2' of the desozaminesugar. However, hybrid compounds with the steroid subunit being linked with the peptide linker in the position N/9a of 9-dihydro-9-deoxo-9a-aza-9a-homoerythromycin, which also possess the above mentioned therapeutic action, have not so far been described. Nor have hybrid compounds been described with the nonsteroidal/antineoplastic/antiviral subunits linked with the peptide linker in, the position N/9a. Nor have hybrid compounds been described with the macrolide being linked with an antiviral or anti-neoplastic subunit. All such compounds are the subject of the present application.

The present invention is directed to
(a) new "hybrid" compounds represented by Formula I:

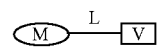

I wherein M represents a macrolide subunit possessing the property of accumulation in inflammatory cells, V represents an anti-inflammatory steroid or non-steroid subunit, or an antineoplastic or antiviral subunit, as defined below, and L represents a linking group covalently linking M and V;
(b) compositions containing one or more of the foregoing compounds in an amount effective to combat inflammation or malignant tumor or virus and thereby to treat disorders and conditions involving inflammation, malignancy or viral infection in mammals, including humans; and
(c) methods for using these compounds to treat such disorders and conditions.

The present compounds advantageously provide an improved therapeutic effect and/or an improved side effect profile.

Suitable macrolide subunits for the hybrid compounds of the present invention can be selected without limitation from multi-member lactonic ring molecules, wherein "member" refers to the carbon atoms or heteroatoms in the ring, and "multi" is a number greater than about 10, preferably from 10 to about 50, more preferably 12-, 14-, 15-, 16-, 17- and 18-member lactonic ring macrolides. 14- and 15-member ring macrolide subunits are particularly preferred, with azithromycin and its derivatives and erythromycin and its derivatives being most preferred.

More specific nonlimiting examples of molecules from which the macrolide subunit can be selected are the following:

(i) Macrolide antibiotics, including azalides, for example erythromycin, dirithromycin, azithromycin, 9-dihydro-9-deoxo-9a-aza-9a-homoerythromycin, HMR 3004, HMR 3647, HMR 3787, josamycin, erythromycylamine, ABT 773 flurithromycin, clarithromycin, tylosin, tilmicosin, oleandomycin, desmycosin, CP-163505, roxithromycin, miocamycin and rokitamycin and derivatives thereof, such as ketolides (e.g., 3-ketone), lactams (e.g., 8a- or 9a-lactams) and derivatives lacking one or more sugar moieties.
(ii) Macrolide immunosuppressants, such as FK 506, cyclosporin, amphotericin and rapamycin;
(iii) Macrolide antifungals with host cell inhibitory properties, such as bafilomycins, concanamycin, nystatin, natamycin, candicidin, filipin, etruscomycin, trichomycin.

Methodologies for the synthesis of the above macrolides not commercially available and synthetic manipulation of macrolides in general are known to those of ordinary skill in the art, or may be found in: Denis A. et al. Bioorg. & Med. Chem. Lett 1999, 9, 3075–3080; Agouridas C. et al. J. Med. Chem. 1998, 41, 4080–4100; and EP-00680967 (1998); Sun Or Y. et al. J. Med. Chem. 2000, 43, 1045–1049; U.S. Pat. No. 0,5747,467 (1998); McFarland J. W. et al. J. Med. Chem. 1997, 40, 1041–1045; Denis A. at al. Bioorg.& Med. Chem. Lett. 1998, 8, 2427–2432; WO-09951616 (1999); Lartey et al. J Med Chem. 1995, 38, 1793–1798; EP 0984019; WO 98/56801, herein incorporated by reference in their entirety.

Additional suitable macrolides are known, some being disclosed in Bryskier, A. J. et al. *Macrolides, Chemistry, Pharmacology and Clinical Use*; Arnette Blackwell: Paris, 1993, pp 485–491, 14(R)-hydroxyclarithromycin, erythromycin-11,12-carbonate, tri-O-acetyloleandomycin, spiramycin, leucomycin, midecamycin, rasaramycinin incorporated by reference in its entirety; in Ma, Z. et al. *Current Medicinal Chemisty-Anti-Infective Agents*, 2002, 1,15–34; also incorporated by reference in its entirety pikromycin, narbomycin, HMR-3562, CP-654743, CP-605006, TE-802, TE-935, TE-943, TE-806, 6,11-bridged ketolides, CP-544372, FMA-199, A-179461; See, in particular the structures and derivatives for 14- and 16-member ring macrolides at pp 487–491 of Bryskier, et al., and the various ketolide derivatives and syntheses in Ma et al., notably in all the structure tables and all the reaction schemes. All these macrolides after being conjugated to V are within the scope of the present invention. The foregoing specifically named or referenced macrolide compounds are commercially available or methods for their syntheses are known.

It is important that the macrolide subunit derive from a macrolide having the property of accumulating within immune system cells recruited to the site of inflammation, especially phagocytic cells. Most of the lactonic compounds defined above are known to have this property. For example, 14-membered macrolides such as erythromycin and its derivatives; 15-membered macrolides such as azithromycin and its derivatives, as well as 8a- and 9a-lactams and their derivatives; 16-membered macrolides such as tilmicosin and desmycosin; and spiramycin.

Additional examples of macrolides accumulating within specific classes of cells may be found in: Pascual A. et al. Clin. Microbiol. Infect. 2001, 7, 65–69. (Uptake and intracellular activity of ketolide HMR 3647 in human phagocytic and non-phagocytic cells); Hand W. L. et al. Int. J. Antimicrob. Agents, 2001, 18, 419–425. (Characteristics and mechanisms of azithromycin accumulation and efflux in human polymorphonuclear leukocytes); Amsden G. W. Int. J. Antimicrob. Agents, 2001, 18, 11–15. (Advanced-generation macrolides: tissue-directed antibiotics); Johnson J. D. et al. J. Lab. Clin. Med. 1980, 95, 429–439. (Antibiotic uptake by alveolar macrophages); Wildfeuer A. et al. Antimicrob. Agents Chemother. 1996, 40, 75–79. (Uptake of azithromycin by various cells and its intracellular activity under in vivo conditions); Scorneaux B. et al. Poult. Sci. 1998, 77, 1510–1521. (Intracellular accumulation, subcellular distribution, and efflux of tilmicosin in chicken phagocytes); Mtairag E. M. et al. J. Antimicrob. Chemother. 1994, 33, 523–536. (Investigation of dirithromycin and erythromycylamine uptake by human neutrophils in vitro); Anderson R. et al. J. Antimicrob. Chemother. 1988, 22, 923–933. ( An in-vitro evaluation of the cellular uptake and intraphagocytic bioactivity of clarithromycin (A-56268, TE-031), a new macrolide antimicrobial agent); Tasaka Y. et al. Jpn. J. Antibiot. 1988, 41, 836–840. ( Rokitamycin uptake by alveolar macrophages); Harf R. et al. J. Antimicrob. Chetnother. 1988, 22, 135–140. (Spiramycin uptake by alveolar macrophages), herein incorporated by reference in their entirety. U.S. Provisional applications 60/394,671 and 60/394,670 both filed Jul. 8, 2002 herein incorporated by reference in their entireties describe various macrolide linker complexes that can also be used in the context of the present invention.

Moreover, the presence of accumulating property within immune system cells recruited to the site of inflammation, especially phagocytic cells can be easily ascertained by a person of ordinary skill in the field of the invention, using one of the well-known assays for this purpose. For example, the procedure detailed by Olsen, K. M. et al. *Anitmicrob. Agents & Chemother.* 1996, 40, 2582–2585 can be used. Briefly, the cells to be tested, e.g., polymorphonuclear leukocytes can be obtained from venous blood of healthy volunteers by Ficoll-Hypaque centrifugation followed by 2% dextran sedimentation. Erythrocytes are removed. by osmotic lysis, and PMN are evaluated by Trypan blue exclusion. Alternatively, other cell fractions can be separated and similarly tested. Tritiated macrolide compounds (e.g., 10 μM) are incubated with $2.5 \times 10^6$ cells for 120 minutes (37° C., 5% $CO_2$, 90% relative humidity) and the cells are subsequently removed from compound-containing supernatant by centrifugation e.g., through a silicon oil-paraffin layer (86 vol %:14 vol %). The amount of compound is determined, e.g., by scintillation counting, and a score significantly elevated above background indicates accumulation of the macrolide in the cells being tested. See Bryskier et al. *Macrolides, Chemistry, Pharmacology and Clinical Use*; Arnette Blackwell: Paris, 1993 pp 375–386, at page 381, column 2, line 3. Alternatively, the compound is not radiolabeled but the amount of compound can be determined by HPLC.

Other assay methods that can be used are disclosed in Bryskier, A. J. et al. *Macrolides, Chemistry, Pharmacology and Clinical Use*; Arnette Blackwell: Paris, 1993 pp 375–386, incorporated by reference. See, in particular phagocytic uptake determination at pp 380–381 and the particular descriptions as to uptake and localization of macrolides at pp 381, 383 and 385 and the tables at 382 and 383.

In some preferred embodiments, this invention relates to compounds, their. salts and solvates represented by the Formula I, wherein M specifically represents a 14- or 15-member lactonic ring macrolide subunit most preferably represented by the Formula II:

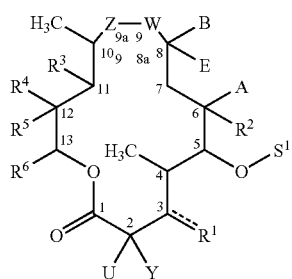

II wherein
(i) Z and W independently are

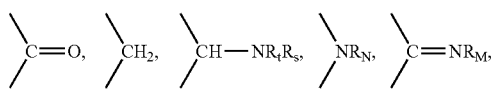

or a bond, wherein $R_t$ and $R_s$ independently are H or alkyl (preferably methyl or H)

$R_M$ is OH, $OR^P$, alkoxy or substituted alkoxy (in either Syn or Anti configuration or mixtures thereof)

$R_N$ is H, $R^P$, alkyl, alkenyl, alkynyl, alkoxy, alkoxyalkyl, or
—C(=X)—$NR_tR_s$;
X is O or S;

provided that Z and W cannot both simultaneously be

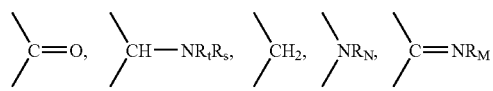

or a bond, (ii) U and Y are independently H, halogen, alkyl, or hydroxyalkyl (preferably H, methyl or hydroxymethyl);
(iii) $R^1$ is hydroxy, $OR^P$, —O—$S^2$, or =O;
(iv) $S^1$ is a sugar moiety at position C/5 of the aglycone ring (e.g., a desozamine group) of the formula:

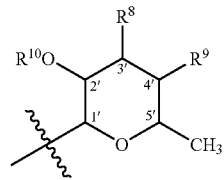

wherein
$R^8$ and $R^9$ are both hydrogen or together form a bond, or $R^9$ is hydrogen and $R^8$ is —$N(CH_3)R^y$, wherein
$R^y$ may be $R^p$, $R^z$ or —C(O)$R^z$, wherein $R^z$ is hydrogen or cycloalkyl (preferably cyclohexyl) or alkyl (preferably a $C_1$–$C_7$ alkyl) or alkenyl (preferably $C_2$–$C_7$-alkenyl) or alkynyl (preferably $C_2$–$C_7$-alkynyl) aryl or heteroaryl or can be alkyl substituted with $C_1$–$C_7$ alkyl or $C_2$–$C_7$ alkenyl or $C_2$–$C_7$ alkynyl or aryl or heteroaryl. ($R^y$ is preferably hydrogen, methyl, or ethyl);
$R^{10}$ is hydrogen or $R^p$;
(v) $S^2$ is a sugar moiety at position C/3 of the aglycone ring (e.g., a cladinosyl group) of the formula

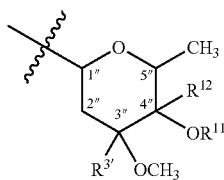

wherein $R^{3'}$ can be H or methyl and $R^{11}$ and $R^{12}$ are independently hydrogen, $R^{11}$ may be an $R^p$ or $R^{11}$ and $R^{12}$ together form a bond
(vi) $R^2$ is H, hydroxy, $OR^P$ group, alkoxy (preferably $C_1$–$C_4$ alkoxy, most preferably methoxy), substituted alkoxy;
(vii) A is H or methyl;
(viii) B is methyl or epoxy;
(ix) E is H or halogen (preferably fluorine);
(x) $R^3$ is hydroxy, $OR^P$ group or alkoxy (preferably $C_1$–$C_4$ alkoxy, most preferably methoxy), substituted alkoxy or $R^3$ is a group that can combine with $R^5$ to form a "bridge" (e.g., a cyclic carbonate or carbamate) or if W or Z is

$R^3$ is a group that can combine with W or Z to form a "bridge" (e.g., a cyclic carbamate);
(xi) $R^4$ is $C_1$–$C_4$ alkyl (preferably methyl);
(xii) $R^5$ is H, hydroxy, $OR^P$ group, $C_1$–$C_4$ alkoxy, substituted alkoxy or a group that may combine with $R^3$ to form a bridge (e.g., a cyclic carbonate or carbamate);
(xiii) $R^6$ is H or $C_1$–$C_4$ alkyl (preferably methyl or ethyl);
wherein the subunit M has a linkage site through which it is linked to the subunit D via the linking group L, the linkage site being at one or more of the following:
a. any reactive hydroxy, N, or epoxy group located on $S^1$, $S^2$, or an aglycone oxygen if $S^2$ is (or if both $S^2$ and $S^1$ are ) cleaved off;

b. a reactive >N—$R_N$, —$NR_rR_s$ or =O group located on Z or W;
c. a reactive hydroxy group located at any one of $R^1$, $R^2$, $R^3$, and $R^5$;
d. any other group that can be first derivatized to a hydroxy or —$NR_rR_5$ group and then linked to all or part of L (e.g., OH—→=O→epoxy→

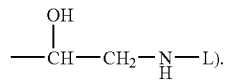

One or more $R^p$ groups may be independently present in the macrolide subunit of Formula II, wherein $R^p$ represents a protective group which may be selected from alkyl (preferably methyl), alkanoyl (preferably acetyl), alkoxycarbonyl (preferably methoxycarbonyl or tert-butoxycarbonyl), arylmethoxycarbonyl (preferably, benzyloxycarbonyl), aroyl (preferably benzoyl), arylalkyl (preferably benzyl), alkylsilyl (preferably trimethylsilyl) or alkylsilylalkoxyalkyl (preferably trimethylsilylethoxymethyl) group. The amino protecting groups may be removed by conventional techniques. Thus, for example acyl groups like alkanoyl, alkoxycarbonyl or aroyl may be removed by solvolysis, e.g. by hydrolysis under acidic or basic conditions. An arylmethoxycarbonyl group (benzyloxycarbonyl) may be cleaved by hydrogenolysis in the presence of a catalyst such as palladium-on-charcoal.

L can be selected to be a linking group represented by the Formula IV:

$$X^1—(CH_2)_m—Q—(CH_2)_n—X^2 \quad\quad IV$$

Wherein
$X^1$ is selected from: —$CH_2$—, —OC(=O)—, —C(=O), =NO—, —OC(=O)NH— or —C(=O)NH—;
$X^2$ is selected from: —NH—, —$CH_2$—, —NHC(=O)—, —OC(=O)—, —C(=O) or, —O;
Q is —NH— or —$CH_2$— or absent;
wherein each —$CH_2$— or —NH— group may be optionally substituted by
$C_1$–$C_7$-alkyl, $C_2$–$C_7$-alkenyl, $C_2$–$C_7$-alkynyl, C(O)$R^x$, C(O)O$R^x$, C(O)NH$R^x$ wherein $R^x$ may be $C_1$–$C_7$-alkyl, aryl or heteroaryl;
the symbols m and n independently are a whole number from 0 to 4.
with the proviso that if Q=NH; n cannot be zero.
L represents a polypeptide linker, of about 2 to about 50 amino acids joined together, preferably tripeptide or tetrapeptide, such as:
Gly-Phe-Leu, Gly-Gly-Phe, Gly-Phe-Phe, Gly-Phe-Gly, Gly-Leu-Gly, Gly-Val-Ala, Gly-Phe-Ala, Gly-Leu-Phe, Gly-Leu-Ala, Ala-Val-Ala, Gly-Gly-Phe-Leu, Gly-PheLeu-Gly, Gly-Phe-Ala-Leu, Ala-Leu-Ala-Leu, Gly-Phe-Phe-Leu, Gly-Leu-Leu-Gly,
Gly-Phe-Tyr-Ala, Gly-Phe-Gly-Phe, Ala-Gly-Val-Phe, Gly-Phe-Phe-Gly, without limitation.
Preferred L is represented by the formula Gly-(W)$_p$-Gly, where p is a whole number from 0 to 3 and W is any amino acid or combination of any amino acids.
In the case when V is a steroid or a non-steroidal antiinflammatory subunit
L is exclusively peptide linker.
V can represent an anti-inflammatory steroid or non-steroid compound subunit, or an antineoplastic or antiviral compound subunit.

When V is a steroid subunit, it is preferably of Formula X:

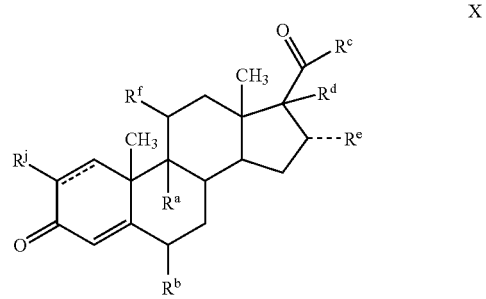

(ii) wherein
$R^a$ and $R^b$ are, independently of each other, hydrogen or halogen;
$R^c$ is hydroxy, alkoxy (preferably methoxy), alkyl, thiocarbamoyl, carbamoyl or a valence-bond;
$R^d$ and $R^e$ are, independently of each other, hydrogen, OH, $CH_3$ or $C_1$–$C_4$ alkoxy (preferably methoxy or n-propoxy) or each are a group that forms a 1,3-dioxolane ring with the other (optionally alkyl or alkenyl mono-or di-substituted) (preferably a 2,2-dimethyl or 2-monopropyl or trans-propenyl ring) or a valence bond;
$R^f$ is hydrogen, hydroxy, chloro, or =O forming a keto group with the carbon atom it is attached to;
$R^j$ is hydrogen or chloro
and their pharmacologically acceptable salts and solvates.
Alternatively, within the present invention are steroid subunits disclosed in WO 94/14834, wherein instead of the group >CH—C(O)—$R^c$ they have the group >CH—S(O)$^n$—$R^c$ wherein n is an integer of 0 to 2. See WO 94/14834 incorporated in its entirety by reference, especially pp 2–3.
More generally, steroids useful as a source of steroid subunits include, but are not limited to, corticosteroids (such as glucocorticoids and mineralocorticoids) and androgens. Non-limiting examples of corticosteroids include cortisol, cortisone, clobetasol, hydrocortisone, fludrocortisone, fludroxycortide, flumetasone, flunisolide, fluocinolone, fluocinonide, fluocortolone, fluorometholone, prednisone, prednisolone, 6-alpha-methylprednisolone, triamcinolone, alclometasone, beclometasone, betamethasone, budesonide, dexamethasone, amcinonide, cortivazol, desonide, desoximethasone diflucortolone, difluprednate, fluclorolone and dichlorisone, fluperinidene, fluticasone, halcinonide, meprednisone, methylprednisolone, pararnethasone, prednazoline, prednylidene, tixocortol, triamcinolone, and acid derivatives thereof, e.g., acetate, propionate, dipropionate, valerate, phosphate, isonicotinate, metasulfobenzoate, tebutate, and hemisuccinate.
V can be a non-steroid anti-inflammatory subunit i.e., a moiety of a nonsteroidal antiinflammatory drug (NSAID) including, those which inhibit cyclooxygenase, the enzyme responsible for the biosyntheses of prostaglandins and certain autocoid inhibitors, including inhibitors of the various isoenzymes, of cyclooxygenase (including, but not limited to, cyclooxygenase-1 and -2), and as inhibitors of both cyclooxygenase and lipoxygenase relates to nonsteroidal antiinflammatory drug (NSAID), such as the commercially available NSAIDs aceclofenac, acemetacin, acetaminophen, acetaminosalol, acetyl-salicylic acid, acetylsalicylic-2-amino-4-picoline-acid, 5-aminoacetylsalicylic acid, aldlofenac, aminoprofen, amfenac, ampyrone, ampiroxicam, anileridine, bendazac, benoxaprofen, bermoprofen, α-bisabolol, bromfenac, 5-bromosalicylic acid acetate, bromosaligenin, bucloxic acid, butibufen, carprofen, celecoxib, chromoglycate, cinmetacin, clindanac, clopirac, sodium diclofenac, diflunisal, ditazol, droxicam, enfenamic acid, etodolac, etofenamate, felbinac, fenbufen, fenclozic acid, fendosal, fenoprofen, fentiazac, fepradinol, flufenac, flufenamic acid, flunixin, flunoxaprofen, flurbiprofen, glutametacin, glycol salicylate, ibufenac, ibuprofen, ibuproxaam, indomethacin, indoprofen, isofezolac, isoxepac, isoxicam;, ketoprofen, ketorolac, lornoxicam, loxoprofen, meclofenamic acid, mefenamic acid, meloxicam, mesalamine, metiazinic acid, mofezolac, montelukast, nabumetone, naproxen, niflumic acid, nimesulide, olsalazine, oxaceprol, oxaprozin, oxyphenbutazone, paracetamol, parsalmide, perisoxal, phenyl-acetyl-salicylate, phenylbutazone, phenylsalicylate, pyrazolac, piroxicam, pirprofen, pranoprofen, protizinic acid, reserveratol, salacetamide, salicylamide, salicylaamide-O-acetyl acid, salicylsulphuric acid, salicin, salicylamide, salsalate, sulindac, suprofen, suxibutazone, tamoxifen, tenoxicam, tiaprofenic acid, tiaramide, ticlopridine, tinoridine, tolfenamic acid, tolmetin, tropesin, xenbucin, ximoprofen, zaltoprofen, zomepirac, tomoxiprol, zafirlukast and cyclosporine. Additional NSAID genera and particular NSAED compounds are disclosed in U.S. Pat. No. 6,297,260, incorporated entirely by reference (especially in the generic formulas of its claim 1 and the specific list of NSAID's contained therein and in claim 3, and thiazulidene NSAIDs disclosed in International Patent Application WO 01/87890, incorporated herein by reference in its entirety).

Preferred NSAIDs are acetyl salicylic acid, indomethacin, naproxen, ibuprofen, flurbiprofen, ketoprofen, sulindac, etodolac, ketorolac, suprofen, flunixin, sodium diclofenac, and tolmetin.

V. can represent anti-viral compounds including acyclovir, famciclovir, ganciclovir, cidofovir, lamivudine, ritonavir, indinavir, nevirapine, zidovudine, didanosine, stavudine, abacavir zalcitabine, amprenavir, ribavirin and adamantane without limitation. Preferred anti-viral compounds are zidovudine, didanosine and stavudine.V can represent antineoplastic agents including bicaluatnide, camptothecin, estramustine phosphate, flutamide, mechlorethamine, thiotepa, ifosfamide, hydroxyurea, bleomycin, paclitaxel, lomustine, irinotecan, methotrexate, vinorelbine, anastrazole, floxuridine, melphalan, vincristine, vinblastine, mitomycin, nandrolone, goserelin, leuprolide, triptorelin, aminogluthetemide, mitotane, cisplatine, chlorambucil, pentostatin, cladribine, busulfan, etoposide, mitoxantrone, idarubicin, cyclophosphamide, mercaptopurine, thioguanine, cytarbine, cyclophosphamide, doxorubicin, daunoribicin, teniposide and tamoxifen without limitation. Preferred antineoplastic agents are methotrexate, paclitaxel, camptothecin doxorubicin taxotere and topotecan.

Bold-faced bonds in formulas contained herein denote bonds raised above the paper level; dash-drawn bonds denote bonds below the paper level, whereas broken lines represent a bond that may be either below or above the paper level. Parallel full and broken lines represent either a single or a double bond. Unless explicitly stated elsewhere herein, the following terms have the meanings ascribed to them below:

"Alkyl" means a linear or branched saturated monovalent hydrocarbon radical of one to ten carbon atoms, more preferably one to six carbon atoms The preferred straight-chain or branched-chain alkyls include methyl, ethyl, propyl, iso-propyl, butyl, sec-butyl and tert-butyl. Methyl is most preferred. Alkyl groups may be substituted with one up to five substituents including halogen (preferably fluorine or chlorine), hydroxy, alkoxy (preferably methoxy or ethoxy), acyl, acylamino cyano, amino, N-(C1–C4)alkylamino (preferably N-methylamino or N-ethylamino), N,N-di(C1–C4-alkyl)amino (preferably dimethylamino or diethylamino), aryl (preferably phenyl) or heteroaryl, thiocarbonylamino, acyloxy, amino, amidino, alkyl amidino, thioamidino, aminoacyl, aminocarbonylamino, aminothiocarbonylamino, aminocarbonyloxy, aryl, heteroaryl, aryloxy, aryloxyaryl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl; cycloalkoxy, heteroaryloxy, heterocyclyloxy, and oxycarbonylamino. Such substituted alkyl groups are within the present definition of "alkyl." The present definition of alkyl carries over to other groups wherein alkyl is a constituent, such as alkoxy.

"Alkenyl" means a linear or branched monovalent hydrocarbon radical of two to ten and preferably two to six carbon atoms which has at least one double carbon-carbon bond. Alkenyl groups may be substituted with the same groups as alkyl and such optionally substituted alkenyl groups are encompassed within the term "alkenyl." Ethenyl, propenyl, butenyl and cyclohexenyl are preferred.

"Alkynyl" means a linear or branched monovalent hydrocarbon radical, having a straight-chain or a branched-chain of two to ten, and preferably two to six carbon atoms and containing at least one and preferably no more than three triple carbon-carbon bonds. Alkynyl groups can be substituted with the same groups as alkyl, and the substituted groups are within the present definition of alkynyl. Ethynyl, propynyl and butynyl groups are preferred.

"Cycloalkyl" means a cyclic group having 3–8 carbon atoms having a single ring optionally fused to an aryl or heteroaryl group. The cycloalkyl groups can be substituted as specified for "aryl" below, and the substituted cycloalkyl groups are within the present definition of "cycloalkyl". Preferred cycloalkyls are cyclopentyl and cyclohexyl.

"Aryl" means an unsaturated aromatic carbocyclic group having 6–14 carbon atoms having a single ring such as phenyl or multiple fused rings such as naphthyl. Aryl may optionally be further fused to an aliphatic or aryl group or can be substituted with one or more substituents such as halogen (fluorine, chlorine and/or bromine), hydroxy, $C_1$–$C_7$ alkyl, $C_1$–$C_7$ alkoxy or aryloxy, $C_1$–$C_7$ alkylthio or arylthio, alkylsulfonyl, cyano or primary or nonprimary amino.

"Heteroaryl" means a monocyclic or a bicyclic aromatic hydrocarbon ring having from 2 to 10 carbon atoms and from 1 to 4 heteroatoms, such as O, S or N. The heteroaryl ring may optionally be fused to another heteroaryl, aryl or aliphatic cyclic group. Examples of this type are furan, thiophene, pyrrole, imidazole, indole, pyridine, oxazole, thiazole, pyrrole, pyrazole, tetrazole, pyrimidine, pyrazine and triazine, with furan, pyrrole, pyridine and indole being preferred. The term includes groups that are substituted with the same substituents as specified for aryl above.

"Heterocyclic" means a saturated or unsaturated group having a single or multiple rings and from 1 to 10 carbon atoms and from 1–4 heteroatoms selected from nitrogen, sulphur or oxygen, wherein in a fused ring system the other ring or rings can be aryl or heteroaryl. Heterocyclic groups can be substituted as specified for alkyl groups and the thus substituted heterocyclic groups are within the present definition.

"Amino acid" refers to any compound containing both an amino group and a carboxylic acid group. The amino group may occur at the position adjacent to the carboxy function, such as in the α-amino acids, or at any location within the molecule. The amino acid may also contain additional functional groups, such as amino, thio, carboxyl, carboxamide, imidazole, etc. The amino acid may be synthetic or naturally occurring, or a modified naturally occurring amino acid, such as norvaline or norleucine.

The symbol K is sometimes used to refer to the part of the L group, linked to M, or to V asthe context requires.

In the, preparation of the compounds represented by the structure I, of the specified pharmacological activity, certain new compounds were prepared as intermediates in the preparation of pharmacologically active compounds. The present invention also relates to such intermediates.

The present invention also encompasses pharmaceutically acceptable salts of the present compounds. Pharmaceutically suitable salts of the compounds of the present invention include salts with inorganic acids (e.g. hydrochloric, hydrobromic, phosphoric, metaphosphoric, nitric or sulfuric acid) or organic acids (e tartaric, acetic, methane-sulfonic, trifluoroacetic, citric, maleic, lactic, fumaric, benzoic, succinic, methanesulfonic, oxalic and p-toluenesulfonic acids).

The present invention also encompasses prodrugs of the Formula I compounds, i.e., compounds which release an active parent drug according to Formula (I) in vivo when administered to a mammalian subject. Prodrugs of a compound of Formula I are prepared by modifying functional groups present in the compound of Formula I in such a way that the modifications may be cleaved in vivo to release the parent compound. Prodrugs include compounds of Formula I wherein a hydroxy, amino, or carboxy group of a Formula I compound is bonded to any group that may be cleaved in vivo to regenerate the free hydroxyl, amino or carboxy group, respectively. Examples of prodrugs include, but are not limited to esters (e.g., acetate, formate, and benzoate derivatives) of compounds of Formula I, or any other derivative which upon being brought to the physiological pH or through enzyme action is converted to the active parent drug. In the context of the present paragraph, "prodrug" does riot refer to hybrid according to the present invention which releases the V moiety, as mentioned elsewhere on the present specification, but it refers to a derivative of the V moiety (which may be released or stay connected with the macrolide). The V moiety derivative in its connected or released state will then convert to the parent active drug which will either be free or connected to the macrolide.

The present invention also encompasses solvates (preferably hydrates) of the compounds of Formula I or their salts.

The compounds of the Formula I have one or more chirality centers and, depending on the nature of individual substituents, they can also have geometrical isomers. Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has a chiral center, a pair of enantiomers is possible. An enantiomer can be characterized by the absolute configuration of its asymmetric center and is described by the R—and S—sequencing rules of Cahn and Prelog, or by the manner in which the molecule rotates the plane of polarized light and designated as dextrorotatory or levorotatory (i.e., as (+) or (−)-isomer respectively). A chiral compound can exist as either an individual enantiomer or as a mixture of enantiomers. A mixture containing equal proportions of the enantiomers is called a "racemic mixture". The present invention encompasses all individual isomers of compounds of Formula I. The description or naming of a particular compound in the specification and claims is intended to include both individual enantiomers and mixtures, racemic or otherwise, thereof. Methods for the determination of stereochemistry and the resolution of stereoisomers are well-known in the art.

The present invention also encompasses stereoisomers of the syn-anti type, encountered when an oxime or similar group is present. The group of highest Cahn Ingold Prelog priority attached to one of the terminal doubly bonded atoms of the oxiie, is compared with hydroxyl group of the oxime. The stereoisomer is designated as Z (zusammen=together) or Syn if the oxime hydroxyl lies on the same side of a reference plane passing through the C=N double bond as the group of highest priority; the other stereolsomer is designated as E (entgegen=opposite) or Anti.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use or for a human pharmaceutical use. A "pharmaceutically acceptable excipient" as used in the present application includes both one and more than one such excipient.

"Treating" or "treatment" of a state, disorder or condition includes:

(1) preventing or delaying the appearance of at least one clinical symptom of the state, disorder or condition developing in a mammal that may be afflicted with or predisposed to the state, disorder or condition but does not yet experience or display clinical or subclinical symptoms of the state, disorder or condition, (2) inhibiting the state, disorder or condition, i.e., arresting or reducing the development of the disease or at least one clinical or subclinical symptom thereof, or (3) relieving the disease, i.e., causing regression of the state, disorder or condition or at least one of its clinical or subclinical symptoms.

The benefit to a subject to be treated is either statically significant or at least perceptible to the patient or to the physician.

A "therapeutically effective amount" means the amount of a compound that, when administered to a mammal for treating a state, disorder or condition, is sufficient to effect such treatment (as the word is defined above). The "therapeutically effective amount" will vary depending on the compound, the disease and its severity and the age, weight, physical condition and responsiveness of the mammal to be treated.

The classic symptoms of acute inflammation are redness, elevated temperature, swelling, pain in the affected area, and loss of function of the affected organ.

Symptoms and signs of inflammation associated with specific conditions include:

rheumatoid arthritis-pain, swelling, warmth and tenderness of the involved joints; generalized and morning stiffness;

insulin-dependent diabetes mellitus-insulitis; this condition can lead to a variety of complications with an inflammatory component, including: retinopathy, neuropathy, nephropathy; coronary artery disease, peripheral vascular disease, and cerebrovascular disease;

autoimmune thyroiditis-weakness, constipation, shortness of breath, puffiness of the face, hands and feet, peripheral edema, bradycardia;

multiple sclerosis-spasticity, blurry vision, vertigo, limb weakness, paresthesias;

uveoretinitis-decreased night vision, loss of peripheral vision;

lupus erythematosus-joint pain, rash, photosensitivity, fever, muscle pain, puffiness of the hands and feet, abnormal urinalysis (hematuria, cylinduria, proteinuria), glomerulonephritis, cognitive dysfunction, vessel thrombosis, pericarditis;

sclerodermna-Raynaud's disease; swelling of the hands, arms, legs and face; skin thickening; pain, swelling and stiffness of the fingers and knees, gastrointestinal dysfunction, restrictive lung disease; pericarditis; renal failure;

other arthritic conditions having an inflammatory component such as rheumatoid spondylitis, osteoarthritis, septic arthritis and polyarthritis-fever, pain, swelling, tenderness;

other inflammatory brain disorders; such as meningitis, Alzheimer's disease, AIDS dementia encephalitis-photophobia, cognitive dysfunction, memory loss;

other inflammatory eye inflammations, such as retinitis-decreased visual acuity;

inflammatory skin disorders, such as , eczema, other dermatites (e.g., atopic, contact), psoriasis, burns induced by UV radiation (sun rays and similar UV sources)-erythema, pain, scaling, swelling, tenderness;

inflammatory bowel disease, such as Crohn's disease, ulcerative colitis- pain, diarrhea, constipation, rectal bleeding, fever, arthritis;

asthma-shortness of breath, wheezing;

other allergy disorders, such as allergic rhinitis-sneezing, itching, runny nose conditions associated with acute trauma such as cerebral injury following stroke-sensory loss, motor loss, cognitive loss;

heart tissue injury due to myocardial ischemia-pain, shortness of breath;

lung injury such as that which occurs in adult respiratory distress syndrome-shortness of breath, hyperventilation, decreased oxygenation, pulmonary infiltrates;

inflammation accompanying infection, such as sepsis, septic shock, toxic shock syndrome-fever, respiratory failure, tachycardia, hypotension, leukocytosis;

other inflammatory conditions associated with particular organs or tissues,
such as nephritis (e.g., glomerulonephritis)-oliguria, abnormal urinalysis;
inflamed appendix-fever, pain, tenderness, leukocytosis;
gout-pain, tenderness, swelling and erythema of the involved joint, elevated serum and/or urinary uric acid;
inflamed gall bladder-abdominal pain and tenderness, fever, nausea, leukocytosis;
chronic obstructive pulmonary disease-shortness of breath, wheezing;
congestive heart failure-shortness of breath, rales, peripheral edema;
Type II diabetes-end organ complications including cardiovascular, ocular, renal, and peripheral vascular disease
lung fibrosis-hyperventilation, shortness of breath, decreased oxygenation;
vascular disease, such as atherosclerosis and restenosis-pain, loss of sensation, diminished pulses, loss of function.
and alloimmunity leading to transplant rejection-pain, tenderness, fever.

Subclinical symptoms include without limitation diagnostic markers for inflammation the appearance of which may precede the manifestation of clinical symptoms. One class of subclinical symptoms is immunological symptoms, such as the invasion or accumulation in an organ or tissue of proinflammatory lymphoid cells or the presence locally or peripherally of activated pro-inflammatory lymphoid cells recognizing a pathogen or an antigen specific to the organ or tissue. Activation of lymphoid cells can be measured by techniques known in the art.

"Delivering" a therapeutically effective amount of an active ingredient to a particular location within a host means causing a therapeutically effective blood concentration of the active ingredient at the particular location. This can be accomplished, e.g., by local or by systemic administration of the active ingredient to the host. The specific viral diseases include viral hepatitis (A, B, C, E), influenza, viral pneumonia, viral bronchitis, herpetic infections (simplex virus, EB virus (infectious mononucleosis), herpes zoster), poliomyelitis, AIDS (HIV infection), adult T-cell leukemia (ATL), papilloma, measles, rubella, exanthema subitum, erythema infectiosum, viral encephalitis, viral myelitis, cytomegalovirus infection, mumps, varicella, rabies, viral enteritis, viral myocarditis, viral pericarditis and so on.

Symptoms and signs of viral infection associated with specific conditions include: viral load, viral replication, viral activity, viremia, virus-specific antigens, viral RNA or DNA, reverse transcriptase activity, antiviral CTL activity in the host, T-cell or CD4+ cell count (for HIV). Cancers include, but are not limited to, the following: Non-small cell lung cancer. Small cell lung cancer, Colon cancer, Breast cancer, Ovarian cancer, Leukemia, Fibroblast, Renal cancer, Melanoma, Prostate cancer, CNS cancer, Bone/muscle, Lymphoma, and blood cancers.

Symptoms and signs of neoplasia associated with specific conditions include: tumor burden, tumor size, afflicted organ weight, tumor recurrence, subject survival time, length and extent of remission, growth of the cancer cells, cancer cell survival, apoptosis index, metastasis extent or rate, biological markers associated with a particular type of neoplasia, proliferation markers, activation of relevant oncogenes, dysregulation of tumor-associated receptor function, tumor-specific antigens, and tumor-associated angioqgenesis.

Subclinical symptoms of viral infection or neoplasia the presence locally or peripherally of activated pro-inflammatory lymphoid cells recognizing a pathogen or an antigen specific to the organ or tissue. Activation of lymphoid cells can be measured by techniques known in the art. Other subclinical symptoms include the presence and/or quantity of various surrogate markers (such as those enumerated above in each category) before any clinical signs of disease appear. In addition, both infection and neoplasia are often accompanied by increased immune system activity at the site of the tumor, so the signs of inflammation are also applicable here.

Preferably, in the compounds represented by the Formula II,

Z and W together are —N($R_N$)C(O)—, —C(O)N($R_N$)—, >C—NR$_s$R$_t$, —C(O)—, >C=N—R$_M$ —CH$_2$NR$_N$— or —NR$_N$CH$_2$—, most preferably, —NCH$_3$CH$_2$—, —NHCH$_2$—, —CH$_2$NH—,
—C(O)NH, —NHCO—,
R$_s$, R$_t$ is methyl or H;
R$_M$ is OH or methoxy;
X is O;
R$_N$ is H, methyl, or —C(=X)—NR$_t$R$_s$;
A is H or methyl U, Y are H, F, methyl or hydroxymethyl;
$R^1$ is hydroxy, —O—$S^2$, or =O
$R^2$ is H, hydroxy or methoxy;
$R^3$ is OH, methoxy or a group that forms a cyclic carbamate bridge with W or Z;
$R^4$ is methyl;
$R^5$ is H, OH, methoxy or a group that forms a cyclic carbonate or carbamate bridge with $R^3$;

The linkage is through the nitrogen of Z at N/9a or N/8a positions or through the carbon of $R^{12}$ or through the oxygen of $R^{11}$ both at C/4" position of $S^2$ sugar.
$R^6$ is H, methyl or ethyl;
$R^8$ is H or; or $N(CH_3)_2$, $NH(CH_3)$ or $N(CH_3)CH_2CH_3$,
$R^9$ is H The linkage site is preferably at position C/3; or through the amino group at position C/3' of $S^1$ sugar or at position C/11 or at W or Z, or through position C/4" of $S^2$ sugar.

Also preferred are compounds within Formula I wherein M is of Formula II and (i) Z is $NCH_3$, W is $CH_2$, $R^2$ is hydroxy; or (ii) Z is NH, W is =CO, and $R^2$ is methoxy. (The compounds described in this paragraph may or may not satisfy the remaining foregoing preferences in the immediately preceding section, but preferably they do.)

A further aspect of the present invention relates to processes for the preparation of compounds represented by Formula I. Generally, the compounds of Formula I may be obtained in the following way: one end of the chain is first linked to the macrolide, and then the other end of the chain is linked to the V; or, one end of the chain is first linked to the V and then the other end of the chain to the macrolide, or finally, one moiety of the chain is linked to the macrolide, whereas the other moiety of the chain is linked to the. V, with the ends of the chain parts being then chemically linked to form the chain L.

It will be appreciated by those skilled in the art that it may be desirable to use protected derivatives of intermediates used in the preparation of the compounds of Formula I. Protection and deprotection of functional groups may be performed by methods known in the art. Hydroxyl or amino groups may be protected with any hydroxyl or amino protecting group, for example, as described in Green, T. W.; Wuts, P. G. M., *Protective Groups in Organic Synthesis*: John Wiley and Sons, New York, 1999. See also the discussion of protective groups in connection with Formula I above. The amino protecting groups may be removed by conventional techniques. For example, acyl groups, such as alkanoyl, alkoxycarbonyl and aroyl groups, may be removed by solvolysis, e.g., by hydrolysis under acidic or basic conditions. Arylmethoxycarbonyl groups (e.g., benzyloxycarbonyl) may be cleaved by hydrogenolysis in the presence of a catalyst such as palladium-on-charcoal.

More specifically, compounds within Formula I can be prepared by the following processes:

a) Compounds of Formula I, where $X^2$ is —NHC(O)—, can be formed by reacting a compound of Formula VI:

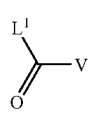

VI wherein $L^1$ represents a leaving group (such as hydroxy), and a free amino group of a macrolide represented by Formula VIIa:

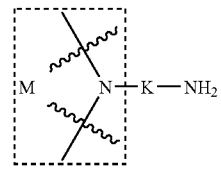

VIIa wherein K is the portion of the linking molecule L attached to the macrolide subunit.

The reaction is generally performed with acid derivatives which have the ability to activate the carboxylic acid group such as halogenides, mixed anhydrides and especially carbodiimides such as (3-dimethylaminopropyl)-3-ethyl-carbodiimide (EDC) and benzotriazoles. The reaction proceeds in the presence of a base, such as an organic base (e.g., triethylamine), at room temperature under an inert atmosphere, such as argon or nitrogen. The reaction may require several hours to several days to come to completion.

For example, when L is —K—$NH_2$ the compound of Formula I can be formed by derivatizing an >NH group on the macrolide ring to an >N—K—$NH_2$ group and reacting the derivatized macrolide with a compound of Formula VI as shown below.

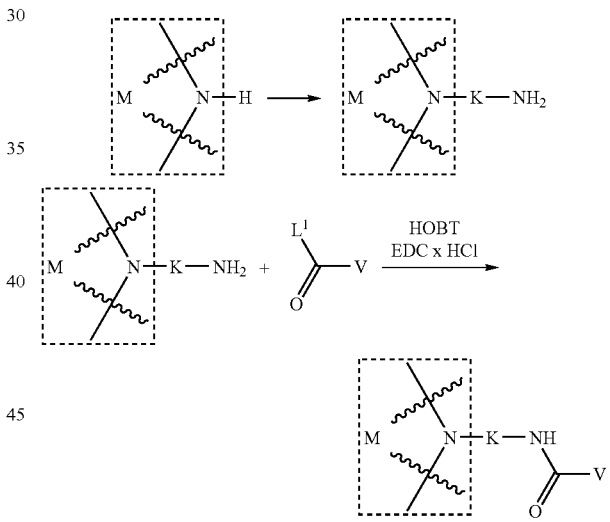

For example this process may be performed when the >NH group in the macrolide subunit of Formula II is attached at the C/3' or N/9a position.

Compound represented by Formula VI are commercially available or they can be derived from the subunit V by methods known in the art to include one.

Preparation of the starting macrolide of Formula VIIa has been described in PCT HR 02/0001, incorporated by reference in its entirety. See also U.S. Pat. No. 4,474,768 and Bright, G. M. et al, *J. Antibiot.* 1988, 41, 1029–1047, each incorporated by reference in its entirety.

b) Compounds represented by Formula I, where $X^2$ is —OC(O)—, can be formed by reacting a compound of Formula VI:

and the free hydroxyl group of a macrolide represented by Formula VIIb:

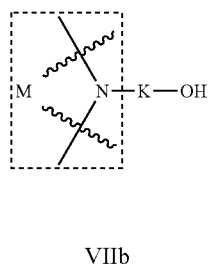

VIIb

The reaction is generally performed with acid derivatives which have the ability to activate the carboxylic acid group, such as halogenides (suh as ethylene dichloride-EDC), mixed anhydrides, especially carbodiimides. The reaction is typically performed at room temperature under an inert atmosphere, such as argon or nitrogen. The reaction may require several hours to several days to come to completion.

For example, when linkage L is —K—O—, the compound of Formula I can be formed by (1) derivatizing an >NH group on a macrolide to an >N—K—OH group and (2) reacting the derivatized macrolide with a compound represented by Formula VI as shown below.

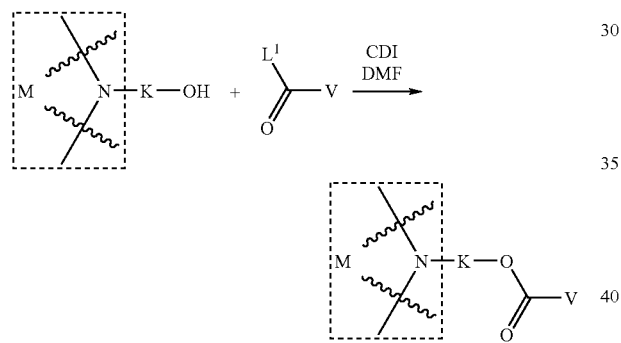

The linkage group —K—OH can be attached to the secondary nitrogen atom of the macrolide as follows. The macrolide is reacted with an alkenoyl derivative, such as $CH_2$=$CH(CH_2)_{m-2}$—C(O)O-alkyl (e.g., methylacrylate). The ester group (i.e., —C(O)O-alkyl) is then reduced, such as with a metal hydride (e.g., $LiAlH_4$) in an anhydrous organic solvent, to yield the macrolide having the linkage group —K—OH (i.e., M—K—OH). The reduction is typically performed at a low temperature and preferably at 0° C. or lower.

For example this process can also be performed when the >NH group is attached at the C/3' or N/9a position of the macrolide subunits represented by Formula II.

The starting macrolide of Formula VIIb are known compounds or may be obtained according to the procedures described for analogous compounds, such as those described in Costa, A. M. et al. *Tetrahedron Letters* 2000, 41, 3371–3375, which is hereby incorporated by reference.

c) Compounds represented by Formula I, wherein $X^1$ is —OC(O)—, Q is —NH— and $X^2$ is —NHC(O)—, can be prepared by reacting a macrolide represented by Formula VIIc:

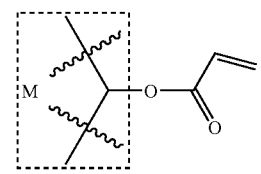

and a compound represented by Formula VIb:

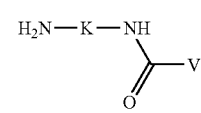

to yield

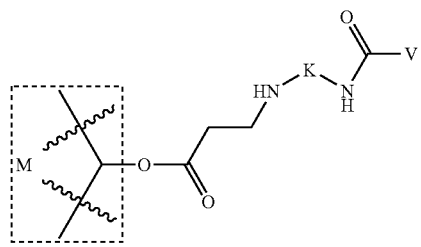

For example this process can be performed when OH group is attached at the C/6 or C/4" position of the macrolide subunit represented by Formula II.

The macrolide represented by Formula VIIc can be formed by the reaction of the corresponding halogenalkanoyl chloride on the free OH group of the macrolide.

The compound represented by Formula VIb may be formed by reacting an appropriate amine (having the linkage group —K—$NH_2$) with compound of Formula VI.

d) Compounds of Formula I, where $X^1$ is —OC(O)NH— and $X^2$ is —NHC(O)—, can be prepared by reacting a macrolide represented by Formula VIId and a compound of Formula VIb as shown below.

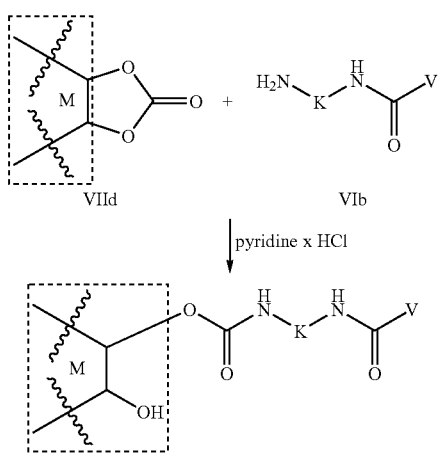

This process can be performed when the two free OH group are attached, for example, at the C/11 and C/12 position of the macrolide subunit represented by Formula II.

The reactant macrolide represented by Formula VIId can be formed by the reaction of the ethylcarbonate on the macrolide subunit having the two vicinal hydroxy substituents;

e) Compounds represented by Formula I, where $X^1$ is —$CH^2$—, Q is —NH— and $X^2$ is —NHC(O)—, can be prepared by reacting a macrolide represented by Formula VIIe and a compound of Formula VIa as shown below.

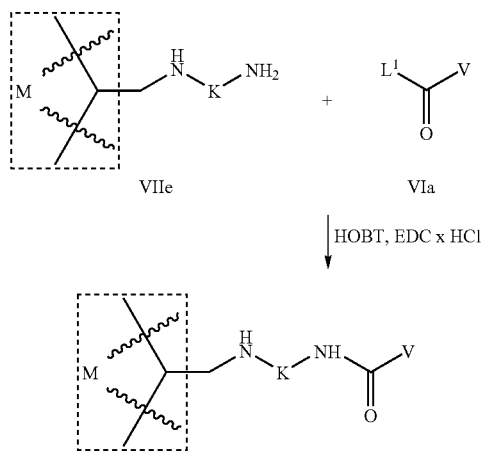

VIIe    VIa

| HOBT, EDC x HCl

For example this process can be performed when the OH group is atached at the C/4" position of the macrolide subunit represented by Formula II.

The reactant macrolide represented by Formula VIIe can be formed by oxidizing the corresponding macrolide having a hydroxy group to obtain a substituent,

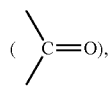

converting to an epoxy group

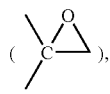

and cleaving the epoxy group with an appropriate reactant (e.g., ethylenediamine).

f) Compounds of Formula I can be prepared by reacting a macrolide represented by Formula VIIf having a leaving group $L^2$ (such as Br), and a subunit V represented by Formula VIc as shown below.

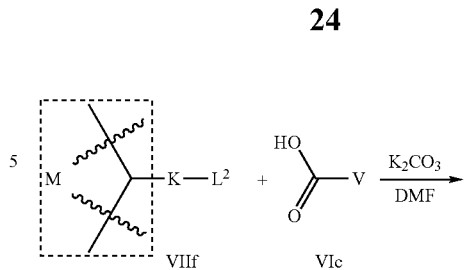

The starting macrolide of Formula VIIf can be prepared, for example, by cleaving the sugar group. attached at the C/3-position of the macrolide subunit represented by Formula II and then reacting the macrolide with a reagent of Formula $L^3$—K—$L^2$, where $L^2$ and $L^3$ are leaving groups.

g) Compounds of Formula I can be prepared by reacting a macrolide represented by Formula VIIg having a leaving group $L^2$ (such as Br), and a subunit V of Formula VIc as shown below.

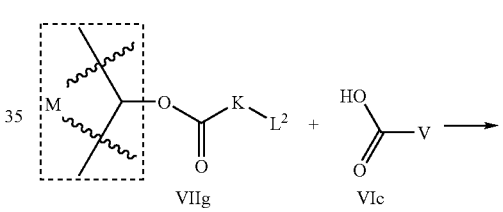

The starting macrolide of Formula VIIg can be prepared by a reaction of an macrolide having a free OH group, for example, at C/2' position of the macrolid subunit represented by Formula II, with a reagent of Formula $L^3$—C(O)—K—$L^2$, where $L^2$ and $L^3$ are leaving groups.

h) Compounds represented by Formula I can be also prepared by reacting a macrolide represented by Formula VIIh having a leaving group $L^2$ (such as Br) and a subunit V of Formula VIc as shown below.

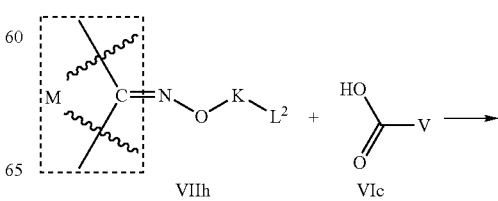

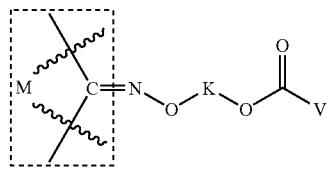

i) Compounds represented by Formula I can be also prepared by reacting a subunit V represented by Formula VIIIa prepared from subunit V with free hydroxyl group (Huang C. M. et al. Chem.&Biol. 2000, 7, 453–461; Hess S. et al. Bioorg.&Med. Chem. 2001, 9, 1279–1291) and macrolide represented by Formula VIIa as shown below.

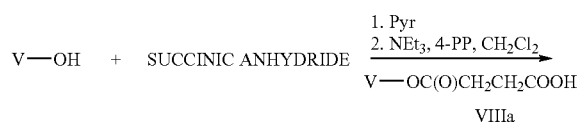

j) Compounds represented by Formula I can be also prepared by reacting a subunit V represented by Formula VIIIb (Pandori M. W. et al. Chem.&Biol. 2002, 9, 567–573) or VIIc prepared from subunit V with free amino group (Hess S. et al. Bioorg.&Med. Chem. 2001, 9, 1279–1291) and macrolide represented by Formula VIIa as shown below.

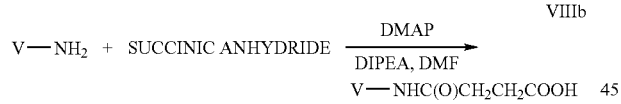

or

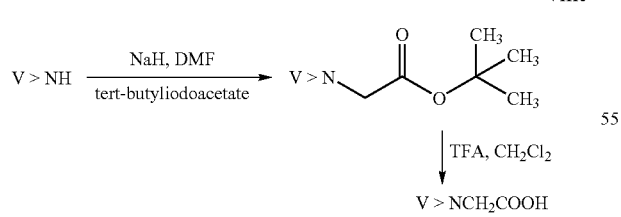

The following examples illustrate preparation of the compound of formula I and do not limit the invention in any way. Paclitaxel succinate can be prepared according to the procedure of Huang C. M. et al. Chemistry&Biology, 7, 2000, 453–461 (Scheme 1).

γ-Methyl-N'-[4-[N-[(2,4-diamino-6-pteridinyl)methyl]-N-methylamino]benzoyl]-L-glutamate (2) can be prepared according to the procedure Kralovec J. et al. J. Med. Chem. 32, 1989, 2426–2431 (Scheme 2).

Camptothecin-20-O-hemisuccinate can be prepared according to the patent application U.S. Pat. No. 4,943,579 (Scheme 3).

5'-O-Succinylzidovudine (m=1) can be prepared according to the procedure of Giammona G. et al. J. Control. Release, 54, 1998, 321–331 (Scheme 4).

Scheme 1: Synthesis of Paclitaxel-macrolide hybridScheme 2: Synthesis of Methotrexate-macrolide hybrid {scheme 2}

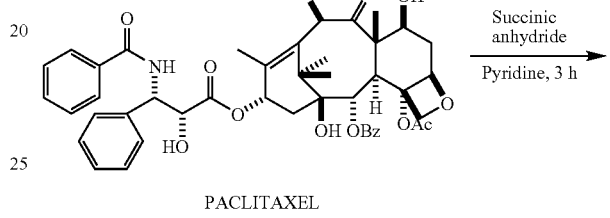

PACLITAXEL

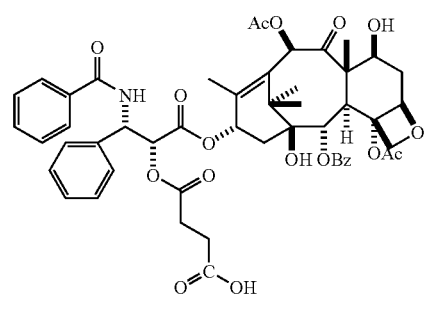

PACLITAXEL SUCCINATE

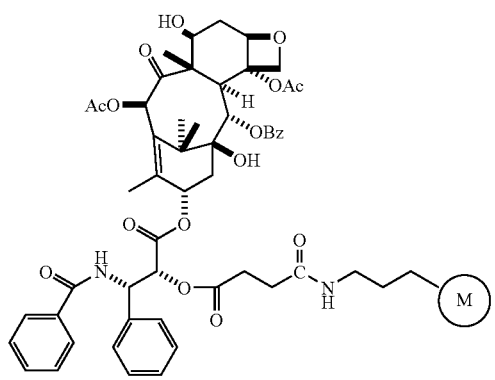

Scheme 2: Synthesis of Methotrexate-macrolide hybrid {scheme 2}.
Scheme 3:
Synthesis of Camptothecin-macrolide hybrid
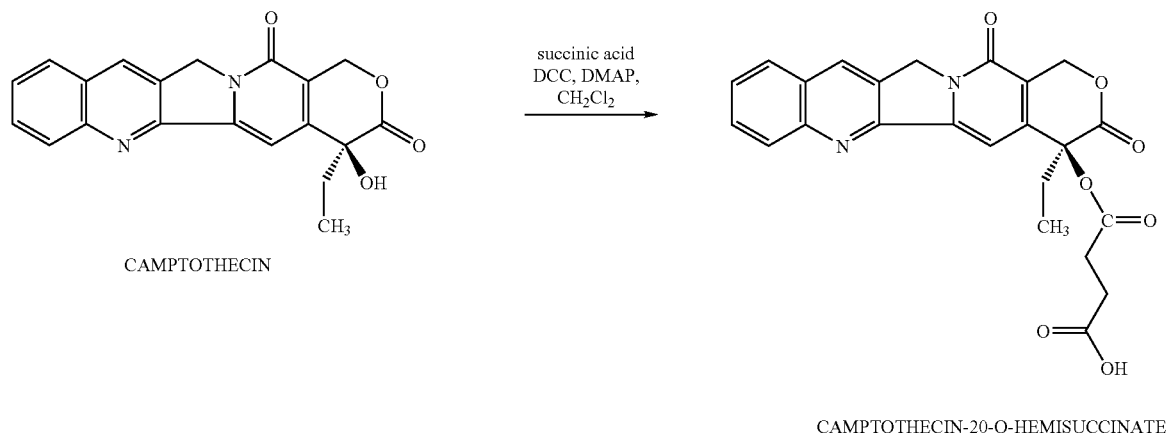
CAMPTOTHECIN-20-O-HEMISUCCINATE
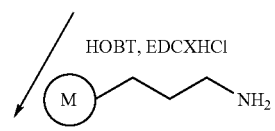
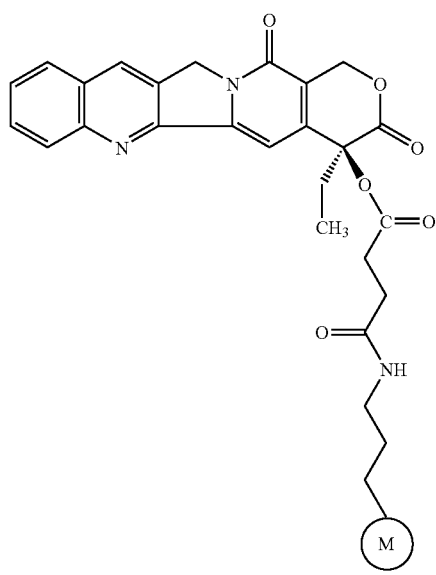

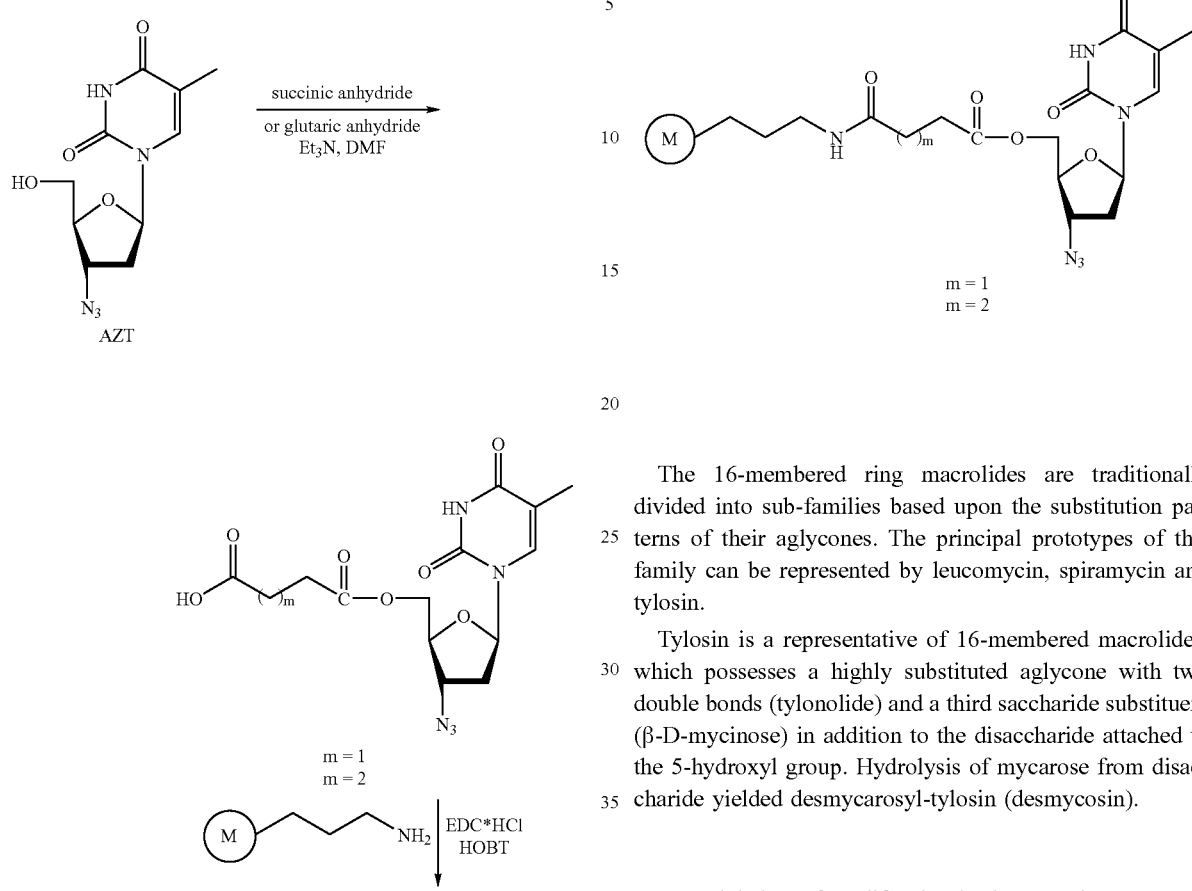

Scheme 4:
Synthesis of Zidovudine(AZT)-macrolide hybrid

-continued

The 16-membered ring macrolides are traditionally divided into sub-families based upon the substitution patterns of their aglycones. The principal prototypes of this family can be represented by leucomycin, spiramycin and tylosin.

Tylosin is a representative of 16-membered macrolides, which possesses a highly substituted aglycone with two double bonds (tylonolide) and a third saccharide substituent (β-D-mycinose) in addition to the disaccharide attached to the 5-hydroxyl group. Hydrolysis of mycarose from disaccharide yielded desmycarosyl-tylosin (desmycosin).

Potential sites of modification in desmycosin:

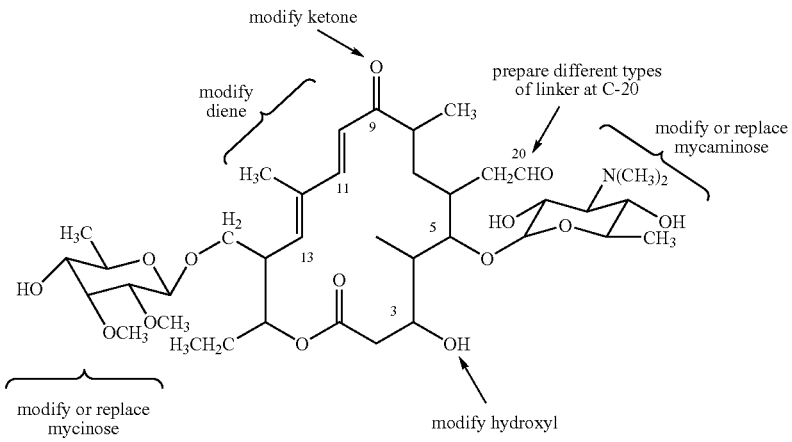

For example, a 16-membered ring macrolide hybrid could be prepared by reductive amination of the C-20 aldehyde group.

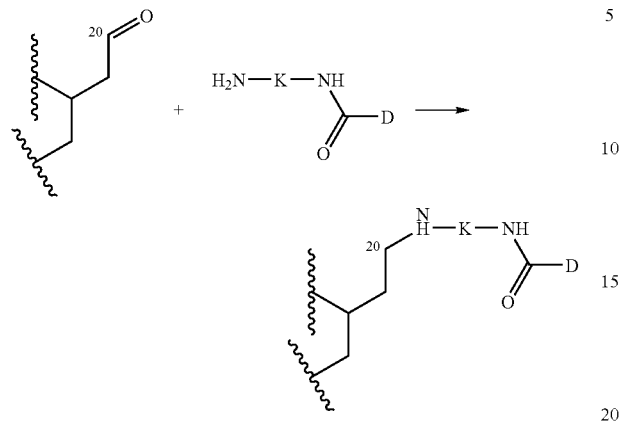

This reaction could be used also for 17-membered azalides like 8a-aza-homodesmycosins and its derivatives (such as di- and tetrahydro derivatives).

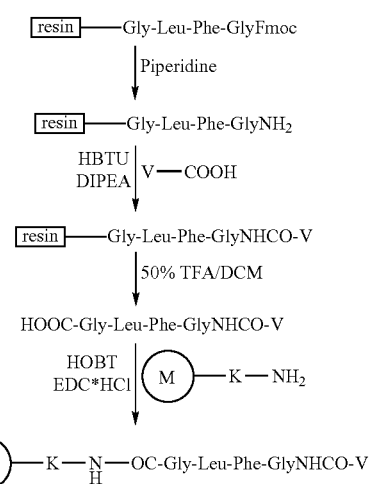

$R^{14}$ is hydrogen or hydroxy

Alternatively 16-membered ring macrolide derivatisation ca proceed by transformations of double bonds (e.g., epoxidation), and cleaving the epoxy group with an appropriate reactant (such as diamine) to yield the macrolide (M—O—NH—K—NH$_2$).

Also the ketone in position C/9 can be modified by hydroxylamine hydrochloride to yield oxime and then reduced to amine.

A synthesis route of compound formula I (V is steroid, nonsteroidal antiinflammatory, antiviral and antineoplastic subunit with free amino group) when L is peptide linker is illustrated by next example:

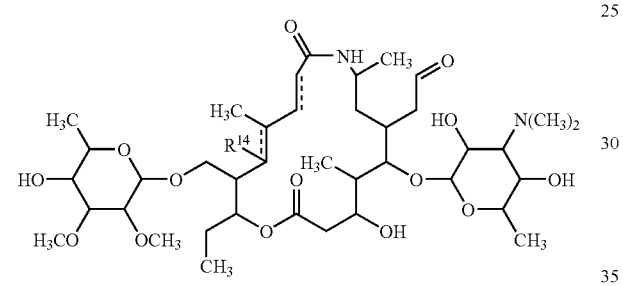

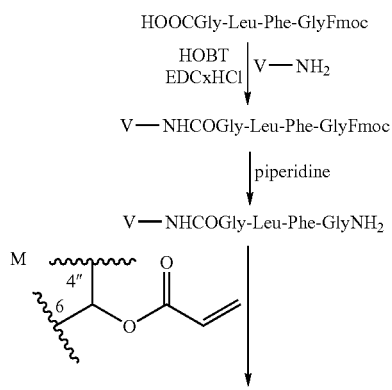

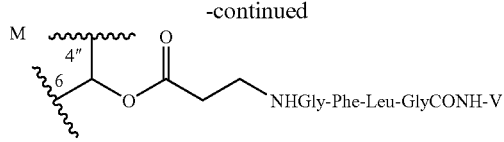

A synthesis route for compound of formula I (V is steroid, nonsteroidal anti-inflammatory, antiviral and antineoplastic subunit with free carboxyl group) when L is peptide linker is illustrated by next example:

resin—Gly-Leu-Phe-GlyFmoc
    ↓ Piperidine
resin—Gly-Leu-Phe-GlyNH$_2$
    ↓ HBTU / DIPEA    V—COOH
resin—Gly-Leu-Phe-GlyNHCO-V
    ↓ 50% TFA/DCM
HOOC-Gly-Leu-Phe-GlyNHCO-V
    ↓ HOBT / EDC*HCl    M—K—NH$_2$
M—K—N(H)—OC-Gly-Leu-Phe-GlyNHCO-V The salts of the compounds represented by Formula I may be prepared by applying generally known procedures such as, e.g., a reaction of the compounds of Formula I with a corresponding base or acid in a suitable solvent or mixture of solvents e.g., ethers (diethyl ether) or alcohols (ethanol, propanol or iso-propanol).

A further aspect of the present invention relates to the use of compounds of Formula I in the treatment of inflammatory diseases, disorders and conditions characterized by or associated with an undesirable inflammatory immune response, especially of all diseases and conditions induced by or associated with an excessive secretion of TNF-α and IL-1. (anticancer, antiviral)

A therapeutically effective amount of the compound of the present invention can be determined by methods known in the art. Since the compound of the present invention is more efficiently delivered to the desired site than the corresponding drug alone, a lesser amount of the compound on a molar basis than of the anti-inflammatory, antineoplastic and antiviral drug can be administered while still achieving the same therapeutic effect. Furthermore, since after being internalized by the target, the active ingredient of the present invention will no longer be in contact with other tissues, it is anticipated that its administration will result in fewer side-effects, which will permit the maximum tolerable anti-inflammatory, antineoplastic and antiviral amount to be increased. Thus, the table below serves only as a guide. A threshold therapeutically effective amount of the compound, a pharmaceutically acceptable salt thereof, a solvate thereof, or a prodrug thereof is generally equal to or less than a therapeutically effective amount of the anti-inflammatory, antineoplastic or antiviral drug on a molar basis. Broad and preferred effective amounts of the compound, a pharmaceutically salt thereof, a solvate thereof, or a prodrug thereof are shown in the table below.

| | Amount of Compound, Pharmaceutically Salt Thereof, Solvate Thereof, or Prodrug Thereof | |
|---|---|---|
| | mg/kg body weight/day of the drug (had it been administered alone | μmol/kg body weight/day of the hybrid or the drug |
| Broad | from about 0.001 to about 1000 | from about 0.004 to about 4000 |
| Preferred | from about 0.01 to about 100 | from about 0.04 to about 400 |
| More Preferred | from about 1 to about 100 | from about 4 to about 400 |
| Most Preferred | from about 3 to about 30 | from about 12 to about 120 |

Thus, for example, the preferred dosage range for indomethacin is 50–200 mg/day, which corresponds to the range of 140 to 560 μmol per day. The same mole-based range, 140–560 mol of a hybrid compound of the invention, will be the starting point for determining the preferred dosage range. Refinements of this approach are well within the skill of the art.

Further, the present invention relates to pharmaceutical compositions containing an effective dose of compounds of the present invention as well as pharmaceutically acceptable excipients, such as carriers or diluents.

The preparation of the pharmaceutical compositions of the invention can include mixing, granulating, tabletting and dissolving the ingredients. Chemical carriers can be in solid or liquid form. Solid carriers can be lactose, sucrose, talc, gelatine, agar, pectin, magnesium stearate, fatty acids without limitation. Liquid carriers can be syrups, oils such as olive, sunflower seed or soybean oils, water, or physiologic saline without limitation. Similarly, carriers may also contain a component for a sustained release of the active component such as glyceryl monostearate or glyceryl distearate. Several forms of pharmaceutical compositions can be prepared. If a solid carrier is used, these forms can include tablets, caplets, solid gelatinous capsules, powders or granules without limitation that can be administered orally. The amount of the solid carrier can vary but mainly it is in the range from 25 mg to 1 g. If a liquid carrier is used, the formulation can be in the form of a syrup, emulsion, soft gelatinous capsules, or sterile injectable liquids, or nonaqueous liquid suspensions.

The compounds of the present invention can be administered topically or systemically, e.g., orally, parenterally, percutaneously, mucosally, e.g., buccally, intranasally, intrarectally and intravaginally. "Parenterally" means by intravenous, intramuscular or subcutaneous route. The corresponding preparations of the compounds of the present invention can be used in the prophylaxis as well as in the therapeutic treatment (prevention, delay, inhibition or relief) of several disorders (diseases and other pathological inflammatory conditions) caused by or associated with an abnormal or undesirable (excessive, nonregulated, or dysregulated) inflammatory immune response involving the production of inflammatory cytokines or other inflammation mediators, including without limitation TNF-α and IL-1β. They include autoimmune diseases such as rheumatoid arthritis, insulin-dependent diabetes mellitus, autoimmune thyroiditis, multiple sclerosis, uveoretinitis, lupus erythematosus, scleroderma; other arthritic conditions having an inflammatory component such as rheumatoid spondylitis, osteoarthritis, septic arthritis and polyarthritis; other inflammatory brain disorders, such as meningitis, Alzheimer's disease, AIDS dementia encephalitis, other inflammatory eye inflammations, such as retinitis; inflammatory skin disorders, such as eczema, other dermatites (e.g., atopic, contact), psoriasis, burns induced by UV radiation (sun rays and similar UV sources); inflammatory bowel disease, such as Crohn's disease, ulcerative colitis; asthma; other allergy disorders, such as allergic rhinitis; conditions associated with acute trauma such as cerebral injury following stroke, heart tissue injury due to myocardial ischemia, lung injury such as that which occurs in adult respiratory distress syndrome; inflammation accompanying infection, such as sepsis, septic shock, toxic shock syndrome, other inflammatory conditions associated with particular organs or tissues, such as nephritis (e.g., glomerulonephritis), inflamed appendix, gout, inflamed gall bladder, chronic obstructive pulmonary disease, congestive heart failure, Type II diabetes, lung fibrosis, vascular disease, such as atherosclerosis and restenosis; and alloimmunity leading to transplant rejection.

The biological activity of the compounds of the present invention was determined in the following in vitro and in vivo experiments:

2. Assay of Binding to Human Glucocorticoid Receptor

The gene for the alpha isoform of human glucocorticoid receptor (EMBL Acc. No. M10901) is cloned by reverse. polymerase chain reaction. The total RNA is isolated from human peripheral blood lymphocytes according to the instructions of the manufacturer (Qiagen), transcripted into eDNA with AMV reverse transcriptase (Roche) on 50 C for 45 minutes and the gene is multiplied by specific primers 1)    5'ATATGGATCCCTGATGGACTCCAAA-GAATCATTAACTCC3' and 2)    5'ATATCTCGAGGGCAGTCACTTTTGAT-GAAACAGAAG3'.

and pfx polymerase (Invitrogen). PCR conditions are: 94 C denaturation for 30 seconds, 55 C annealing for 30 seconds, 68 C for 3minutes, with total 36 cycles; final extension step on 68 C for 7 minutes. The reaction product obtained is cloned into the the dideoxy fluorescent method with M13 and M13rev primers (Microsynth) and then it is cloned into the XhoI/BamHI site of pcDNA3.1 hygro(+) plasmid (Invitrogen Life Technologies). $1\times10^5$ COS-1 cells are seeded onto a 12-well plate (Falcon) in DMEM medium (Invitrogen Life Technologies) with 10% FBS (Biowhitaker) and cultivated to a 70% confluence at 37° C. in an atmosphere with 5% $CO_2$. The medium is removed and 1 μg of DNA, 7 μl of PLUS reagent and 2 μl of Lipofectamine (Life Technologies) in 500 μl DMEM are added per well. The cells are incubated at 37° C. in an atmosphere with 5% $CO_2$ and after 5 hours the same volume of 20% FBS/DMEM is added. After 24 hours, the medium is completely changed. 48 hours after transfection, the test compounds in different concentrations and 24 nM [$^3$H]dexamethasone. (Pharmacia) in DMEM medium are added. The cells are incubated for 90 minutes at 37° C. in an atmosphere with 5% $CO_2$, washed three times with PBS buffer (Sigma) cooled to 4° C. (pH=7.4) and then lysed in Tris buffer (pH=8.0) (Sigma) with 0.2% SDS (Sigma). After the addition of UltimaGold XR (Packard) scintillation liquid, the residual radioactivity is read in a Tricarb (Packard) β-scintillation counter.

3. Assay of Inhibition of Mouse T-cell Hybridoma 13 Proliferation as a Result of Apoptosis Induction In a 96-well plate, triplicates of test steroid dilution in RPMI medium (Instituted of Immunology, Zagreb) with 10% FBS are performed. To the solutions of compounds, 20000 cells per well are added and incubated overnight at 37° C. in an atmosphere with 5% $CO_2$, then 1 µCi of [$^3$H]thymidine (Pharmacia) is added and the mixture was incubated for additional 3 hours. The cells are harvested by applying a vacuum over GF/C filter (Packard). Onto each well, 30 µl of Microscynt O scintillation liquid (Packard) is added and the incorporated radioactivityis measured on a β-scintillation counter (Packard). The specificity of apoptosis induction by glucocorticoids is proven by antagonising the proliferation inhibition with mifepristone (Sigma).

Model of Lung Eosinophilia in Mice

Male Balb/C mice with a body weight of 20–25 g are randomly divided into groups, and sensitized by an i.p. injection of ovalbumin (OVA, Sigma) on day zero and day fourteen. On the twentieth day, the mice are subjected to a challenge test by i.n. (intranasal) application of OVA (positive control or test groups) or PBS (negative control). 48 hours after i.n. application of OVA, the animals are anaesthetized and the lungs are rinsed with 1 mL of PBS. The cells are separated on Cytospin 3 cytocentrifuge (Shandon). The cells are stained in Diff-Quick (Dade) and the percentage of eosinophils is determined by differential counting of at least 100 cells.

Fluticasone and beclomethasone are used as standard anti-inflammatory substances.

The compounds are administered daily i.n. or i.p. in different doses 2 days before the provocative test and up to the completion of the test. Compounds are administered as suspension either in carboxymethyl cellulose or in lactose solution.

Model of Corticosterone Suppression and Thymus Size Reduction in Rats

Male Wistar rats with a body weight between 200 and 250 g are randomly divided. Tested compounds and standard glucocorticoids are applied by s.c. route once a day for three days. On day three, rats are subjected to cold stress (4° C., for one hour), anesthesized with Thiopenetal (Pliva Inc.) and blood is taken on heparin. The complete thymus is removed from each animal, and weighed immediately. Plasma is stored at −70° C. until assayed. Corticosterone is extracted with chloroform (5 mL) from 1 mL plasma, or from corticosterone standard dilutions in PBS, intereferent compounds were washed with 0.1 M NaOH, and sulfuric acid:$H_2O$: $C_2H_5OH$=8:2:1 is added. Fluorescence is measured 60 minutes later, excitation/emission wavelength is 470/530.

b) Determination of TNF-α and IL-1β Secretion in Mononuclear Cells of Human Peripheral Blood in vitro Peripheral blood mononuclear cells (PMWC) are prepared from heparinized whole blood after separation of PMBC on Ficoll-Hypaque (Amersham-Pharmacia). For the determination of TNF-α level, $3.5–5 \times 10^4$ cells are cultured in a total volume of 200 µl within a period of 18 to 24 hours on microtiter flat bottom plates (96 wells, Falcon) in RPMI 1640 medium supplemented with 10% of heat-inactivated human AB serum (Croatian Centre For Transfusion Medicine, Zagreb), 100 units/mL of penicillin, 100 mg/mL of streptomycin and 20 mM HEPES (Invitrogen Life Technologies). The cells are incubated at 37° C. in an atmosphere with 5% $CO_2$ and 90% moisture. The cells in a negative control are cultured only in the medium (NC), while the secretion of TNF-α in a positive control was stimulated by the addition of 1 µg/mL lipopolysaccharide (LPS, *E. coli* serotype 0111:B4, SIGMA) (PC) and the effect of the tested substances on TNF-α secretion is tested after their addition to cell cultures stimulated with LPS (TS). The TNF-α level in the cell supernatant is determined by ELISA according to the manufacturer's (R&D Systems) suggestions. The test sensitivity was <3 pg/mL TNF-α. The determination of IL-1β level is performed as described for TNF-α determination, only that $1 \times 10^5$ cells/well and 0.1 ng/mL of LPS are used. IL-1β level is determined by ELISA (R&D Systems). The percentage inhibition of TNF-α or IL-1β production is calculated by the following equation:

% inhibition=[1−(TS−NC)/(PC−NC)]×100

IC-50 value is defined as the concentration of the substance at which 50% of TNF-α production is inhibited. The compounds demonstrating IC-50 in concentrations of 20 µM or lower are considered active. IC-50 is calculated using Graph Pad Prism Software.

c) Determination of TNF-α Secretion by RAW 264.7 Cells

The cells are grown in 10% fetal bovine serum (FBS) in DMEM medium (Invitrogen Life Technologies) at 37° C. in an atmosphere with 5% $CO_2$ and 90% moisture. 20 000 cells/well are plated in 96 well plate (Falcon). The cells in a negative control are cultured only in the medium (NC), while the secretion of TNF-α in a positive control is stimulated by the addition of 500 pg/mL lipopolysaccharide (LPS, *E. coli* serotype 0111B:4, SIGMA) (PC) and the effect of the tested substances on TNF-α secretion is tested after their addition to cell cultures stimulated with LPS (TS). The TNF-α level in the cell supernatant is determined by ELISA according to manufacturer s (R&D Systems, Biosource) suggestions. The percentage inhibition of TNF-α production is calculated by the following equation:

% inhibition=[1−(TS−NC)/(PC−NC)]×100

IC-50 value is defined as the concentration of the substance at which 50% of TNF-α production is inhibited. The compounds demonstrating IC-50 in concentrations of 10 µM or lower are considered active.

Human Prostaglandin-H Synthase-1 (hPGH-1) and Human Prostaglandin-H Synthase-2 (hPGH-2) Inhibition Assay Genes coding hPGH-1 and hPGH-2 are amplified with PCR using Platinum pfx DNA polymerase (Invitrogen Life Technologies) from human placenta cDNA library (Stratagene). Primer sequences used for hPGH-1 are: 5'ATATAAGCTTGCGCCATGAGCCGGAGTCTTC 3' and 5'ATATGGATCCTCAGAGCTCTGTGGATGGTCGC 3'; for hPGH-2 5'ATATAAGCTTGCTGCGATGCTCGC-CCGC 3' and 5'ATATGGATCCCTACAGTTCAGT-TCAGTCGAACGTTC 3'. PCR products are cloned into HindIII and BamHI restriction sites of pcDNA3.1 Hygro(+) plasmid (Invitrogen Life Technologies), sequences are confirmed by sequencing.

Transfection is performed on COS-7 cells (ATCC), cells are grown in 10% foetal bovine serum (FBS) in DMEM medium (Invitrogen Life Tecnologies), 37° C. in an atmosphere with 5% $CO_2$ and 90% moisture, to full confluency in 24 well plate (Falcon). 1 µg plasmid DNA (pcDNA Hygro 3.1 (+) containing PGH-1 or PGH-2 gene, or pcDNA Hygro 3.1 (+) for negative control samples) is combined with 1.5 µl Lipofectamine 2000 (Invitrogen Life Technologies), following manufacturer's recommendations. 24–48 hours post transfection, tested compounds in DMEM are added to cells without medium removal, and after 40 minutes, arachidonic acid (Sigma) is added to final 20 µM concentration. After 30 minutes supernatants are removed and PGE-2 is measured with PGE-2 assay kit (Cayman) following manufacturer's instructions. No production of PGE-2 is detected in negative control.

% inhibition is calculated by the following equation:

% inhibition=(1−sample PGE-2 concentration/positive control PGE-2 concentration)*100 d) In vivo Model of LPS-induced Exccessive Secretion of TNF-α in Mice

TNF-α secretion in mice is induced according to the previously described method (Badger A. M. Et al., *J. of Pharmac. and Env. Therap.* 279 1996 1453–1461). In the test, male BALB/c mice at an age of 8 to 12 weeks in groups of 6 to 10 animals are used. Animals are treated p.o. either only with the solvent (in a negative and a positive control) or with solutions of the substance 30 minutes prior to the i.p. treatment with LPS (*E. coli* serotype 0111:B4, Sigma) in a dose of 25 μg/animal. Two hours later the animals are euthanized by means of i.p. injection of Roumpun (Bayer) and Ketanest (Park-Davis). A blood sample from each animal is collected in a "vacutaner" tube (Becton Dickinson) and the plasma is separated according to the manufacturer's suggestions. The TNF-α level in the plasma is determined by ELISA (Biosource, R&D Systems) according to the process prescribed by the manufacturer. The test sensitivity was <3 pg/mL TNF-α. The percentage inhibition of TNF-α production is calculated by the following equation:

% inhibition=[1−(*TS-NC*)/(*PC-NC*)]*100

The compounds demonstrating a 30% or higher inhibition of TNF-α production at a dose of 10 mg/kg are considered active.

e) Writhing Test for Analgesic Activity

In this test, pain is induced with an injection of an irritant, usually acetic acid, into the peritoneal cavity of mice. The animals respond by the characteristic writhings, which gave the name of the test (Collier H. O. J. et al. *Pharmac. Chemother.* 1968, 32, 295–310; Fukawa K. et al. *J. Pharmacol. Meth.*, 1980, 4, 251–259; Schweizer A. et al. *Agents Actions*, 1988, 23, 29–31). This test is suitable for the determination of analgetic activity of compounds. Process: male BALB-/c mice (Charles River, Italy) at an age of 8 to 12 weeks are used. Methyl cellulose is administered p.o. to a control group, 30 minutes prior to i.p. administration of acetic acid in a concentration of 0.6%, whereas to the test groups a standard (acetyl salicylic acid) or test substances in methylcellulose are administered p.o. 30 minutes prior to i.p. administration of 0.6% acetic acid (volume 0.1 mL/10 g). Mice are individually placed under glass funnels and the number of writhings of each animal is recorded during a period of 20 minutes. The percentage inhibition of writhings is calculated according to the equation:

% inhibition=(mean value of number of writhings in the control group—number of writhings in the test group)/number of writhings in the control group×100.

The compounds demonstrating the same or better analgesic activity than acetyl salicylic acid are considered active.

In vivo Model of LPS-induced Shock in Mice

Male BALB/c mice at an age of 8 to 12 weeks (Charles River, Italy) are used. LPS isolated from Serratie marcessans (Sigma, L6136) is diluted in sterile saline. The first LPS injection is administered intradermally in a dose of 4 μg/mouse. 18 to 24 hours later LPS is administered i.v. in a dose of 200 μg/mouse. To a control group, two LPS injections are administered in the above described manner. The test groups are administered the substances p.o. half an hour prior to each LPS administration. The survival after 24 hours is observed.

The compounds resulting in a 40% or better survival at a dose of 30 mg/kg are considered active.

Compounds are considered active if they demonstrated a statistically significant (by Student's t-test, $p<0.05$) result in at least two of the foregoing tests. The molar amounts of compound used are below the threshold amount of macrolide (above 30 μm) for exerting a mild anti-inflammatory effect as reported in the literature.

(ii), In Vitro Assay for Screening Inhibitory Effect on HIV Replication

An HIV-1 transformed T4-cell line. MT-4, is previously shown (Koyanagi et al., Int. J. Cancer, 36, 445–451, 1985) to be highly susceptible for HIV infection, served as the target cell line. Inhibition of the HIV-induced cytopathic effect is used as the end point. The viability of both HIV- and mock-infected cells is assessed spectrophotometrically via the in situ reduction of MTT. The 50% cytotoxic concentration is defined as the concentration of compound that reduced the absorbance of the mock-infected control sample by 50%. The percent protection achieved by the compound in HIV-infected cells is calculated as the optical density measured with a given concentration of the test compound in HIV-infected cells. Ratio between cytotoxic and protective effect is measured.

(iii) In Vitro Assay for Screening Inhibitory Effect on HCV Replication

The activity of new compounds is determined using an adaptation of the method reported by Lohmann et al [V. Lohmann et al., Science, 1999,285, 110–113].

The HCV replicon-containing cell line is used to demonstrate the ability of new compounds to inhibit the replication of HCV replicon RNA in cells. The inhibition of the HCV replicon RNA replication will lead to a decrease of the replicon RNA in the cell, which can be measured using a method that specifically quantifies this RNA.

The assay is based on the idea of using a reporter as a simple readout for intracellular HCV replicon RNA level. For this purpose the Renilla luciferase gene is introduced into the first open reading frame of a replicon construct NK5.1 (Krieger et al., J. Virol. 75:4614), immediately after the internal ribosome entry site (IRES) sequence, and fused with the neomycin phosphotransferase (NPTII) gene via a self-cleavage peptide 2A from foot and mouth disease virus (Ryan & Drew, EMBO Vol 13:928–933). After in vitro transcription the RNA was electroporated into human hepatoma Huh7 cells, and G418-resistant colonies are isolated and expanded. Stably selected cell lines is shown to contain replicative HCV subgenomic RNA, and the activity of Renilla luciferase expressed by the replicon reflects its RNA level in the cells.

For the assay procedure, Renilla Luciferase HCV replicon cells that cultured in Dulbecco's MEM Invitrogen cat no. 31966-021) with 5% fetal calf serum (FCS) (Invitrogen cat no. 10106-169) are plated onto a 96-well plate at 5000 cells per well, and incubated overnight. Twenty-four hours later, different dilutions of chemical compounds in the growth medium are added to the cells, which are then further incubated at 37° C. for three days. The assay is carried out in duplicate plates, one in opaque white and one in transparent, in order to measure the activity and cytotoxicity of a chemical compound in parallel ensuring the activity seen is not due to reduction on cell proliferation.

At the end of the incubation time, the cells in the white plate are harvested and luciferase activity is measured by using a Dual-Luciferase reporter assay system (Promega cat no. E1960). All the reagents described in the following paragraph are included in the manufacturer's kit, and the manufacturer's instructions are followed for preparations of the reagents. Briefly, the cells are washed twice with 200 μL PBS (phosphate buffered saline, pH 7.0) per well and lysed with 25 μL of 1× passive lysis buffer prior to incubation at room temperature for 20 min. One hundred microliter of LAR II reagent is added to each well. The plate is then inserted into the microplate luminometer (Packard), and 100 μL of Stop & Glo reagent is injected into each well and luminescence is measured. The IC50, the concentration of the drug required for reducing the replicon level by 50% in relation to the untreated cell control value, can be calculated from the plot of the percentage reduction of the luciferase activity vs. drug concentration.

In Vitro Assay for Antineoplastic Activity

EL-4 cell line is used to screen antineoplastic activity in vitro. Cell are grown in DMEM medium (Invitrogen) supplemented with 10% FBS (Invitrogen), at 37 C, 5% CO2 and 90% relative humidity. Assay is carried out in 96 well plates, with compound dilutions ranging from 10–5 to 10–10 M, and with 30000 cells per well. After 24 hour treatment, 3H labeled thymidine (Amersham) is added for 4 hours. Cells are harvested on cell harvester (Packard) using GF/C filters (Packard). Scintillation liquid (Microscint 20, Packard) is added, and scintillation is counted.

Inhibitory effect is calculated as: % inhibition=(1-CPMsample/CPMpositive control)*100.

L1210 i.p. Tumor Model 106 viable cells are administered to DBA2 mice (male 9–12 weeks, 20–30 g) i.p. on day 0. Animals are subsequently treated with either single or multiple i. p. doses on days 1, 2 and 3 with cisplatin or with the hybrid compounds. Animals are weighed daily and observed twice a day for signs of tumor progression and sacrificed if their body weight fell below 80% of the starting weight or if other severe toxicological problems are seen. At the end of the experiment changes in gross anatomy are noted.

B16 Melanoma i.p. Model

Male C57BL/6J mice are inoculated with 106 viable B16F10 cells intraperitoneally (i.p). The cells are injected on day 0 and free cisplatin or the hybrid compound is injected as single or multiple doses i.p. on subsequent days. Animals are monitored as described above.

B16 Melanoma s.c. Model

Male C57BL/6J mice are inoculated with 105 viable B16F10 cells subcutaneously (s.c.).The tumor is allowed to establish until the area was approximately 50–70 mm2, as measured by the product of two orthogonal diameters. Animals bearing s.c. tumors are treated by either i.p. or i.v. injection of free cisplatin or the hybrid compounds 19–21 at 2, 5, 10, 15 mg Pt/kg.

SYNTHETIC METHODS AND EXAMPLES

Preparation of Intermediates

Intermediate A

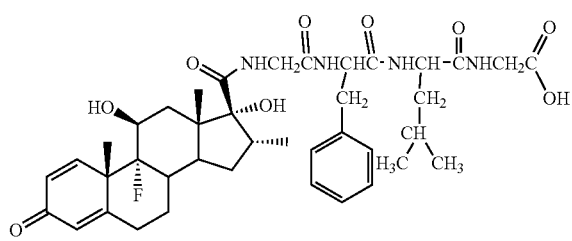

2-Chlorotritylchloride resin (1 eq=0.5 mmol, 600 mg) was placed in a glass column fitted with a coarse glass frit filter and swelled in DCM for 10 min. Then the resin was filtered and washed three times with DCM After washing with DMF the resin was loaded with N-R-Fmoc-glycine by addition of 2.0 mL of a 0.6 M solution of the amino acid in DMF and 0.630 ml of N,N-diisopropylethylamine (DIPEA) and mixed. After 5 min 0.315 ml of DIPEA was added. After mixing for 50 min amount of 0.5 ml of methanol was added. After 10 min the resin was filtered and washed ten times with DCM, DMF and methanol.

Deprotection

Different solutions of piperidine in DMF were prepared and poured over the beads as follows:

| | |
|---|---|
| 5% piperidine/DMF | 10 min (~10 ml) |
| 30% piperidine/DMF | 15 min (~10 ml) |
| 50% piperidine/DMF | 30 min (~10 ml) |

After deprotection the resin was washed with DMF.

The second aminoacid, Fmoc-Leucine(1060 mg, 3 mmol) and 2-(1H-Benzotriazole-1yl)-1,1,3,3-tetramethyluron hexafluorophosphate (HBTU) was dissolved in 3mL of DMF and with 0.216 mL ( 5 mmol) of DIPEA were added rapidly and simultaneously to the monomer/resin mixture in the reaction tube.

End Capping:

Solution of 10 eq ( 2.04 ml) of acetic anhydride and 10 eq ( 3.48 ml) of DIPEA in 5 ml of DMF was prepared. 2.5 ml of this solution was added to the reaction mixture for 5 min.

The second aminoacid was deprotected with a solution of piperidine in DMF as follows:

| | |
|---|---|
| 30% piperidine/DMF | 2 min (~10 ml) |
| 30% piperidine/DMF | 2 min (~10 ml) |
| 30% piperidine/DMF | 5 min (~10 ml) |
| 30% piperidine/DMF | 5 min (~10 ml) | and washed with a big amount of DMF.

The same procedure of coupling an deprotecting was repeated for the third amino acid

| | |
|---|---|
| Fmoc-phenylalanine, 1162 mg, 3 mmol | |
| HBTU, 1081 mg | /3 ml DMF |
| DIPEA, 0.87 ml | |
| and the fourth amino acid | |
| Fmoc-glycine, 892 mg, 3 mmol | |
| HBTU, 1081 mg | /3 ml DMF |
| DIPEA, 0.87 ml | | followed by filtration and washing with DMF.

To the tetrapeptide/resin mixture in the reaction tube the mixture of dexamethasone acid ( 567 mg, 3 eq), HBTU (540 mg, 3.8 eq) and 0.435 ml of DIPEA in 3 ml of DMF was added, mixed and stayed owernight.

End Capping:

Solution of 0.5 ml of acetic anhydride and 0.5 ml of DIPEA in 3 ml of DMF was added to the reaction mixture for 5 min, followed by washing with DCM, DMF and MeOH and drying under vacuum.

Cleavage from the Resin 10 ml of a solution of 50% trifluoroacetic acid in DCM was poured over the beads and mixed for 15 min. Reagents was removed by filtration and the beads were washed 2× with DCM. The same procedure was repeated with the next 10 ml of acid.

Collected solvent was evaporated removing the exces of TFA with adding amount of diethylether. 60.1 mg of intermediate A was isolated. MS (m/z): 753.3 [MH]$^+$

Example I

Compound 1
(Dexamethasone-Gly-Phe-Leu-Gly-Azithromycin)

Intermediate B

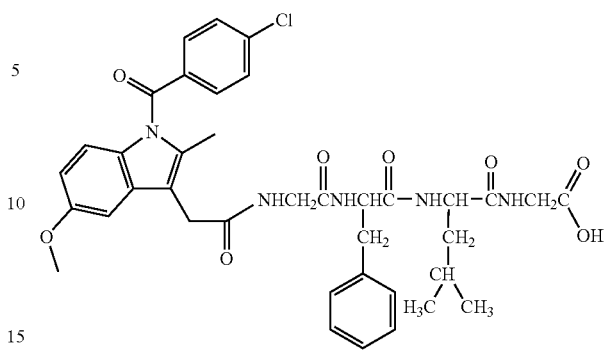

2-Chlorotritylchloride resin (1 eq=0.5 mmol, 600 mg) was placed in a glass column fitted with a coarse glass frit filter arid swelled in DCM for 10 min. Then the resin was filtered and washed three times with DCM. After washing with DMF the resin was loaded with N-R-Fmoc-glycine by addition of 2.0 mL of a 0.6 M solution of the amino acid in DMF and 0.630 ml of N,N-diisopropylethylamine (DIPEA) and mixed. After 5 min 0.315 ml of DIPEA was added. After mixing for 50 min amount of 0.5 ml of methanol was added.

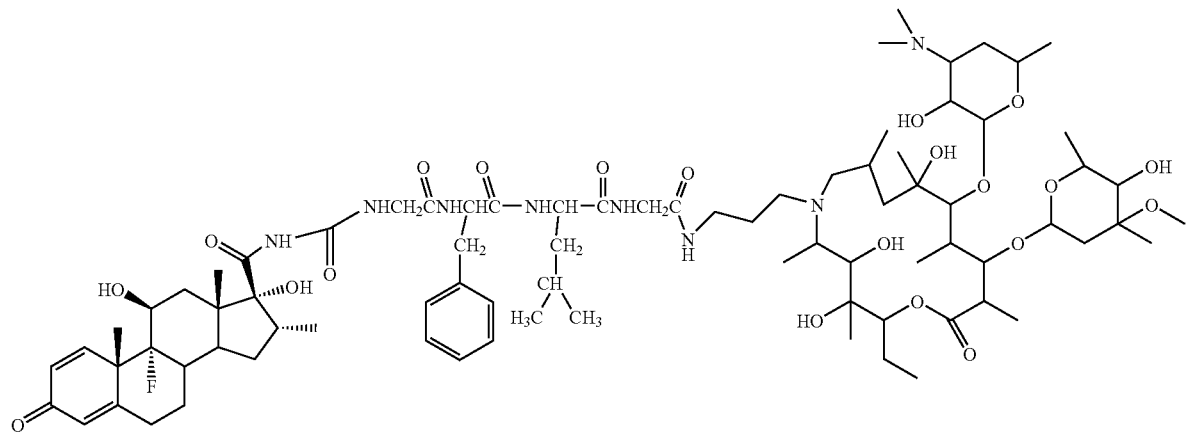

Intermediate A (57 mg; 0.076 mmole) was dissolved in dry CH$_2$Cl$_2$ (5 mL) in an inert atmosphere and cooled at 0° C. 0.115 mL of N,N-diisopropylethylamine and 20.5 mg of 1-hydroxybenzotriazole were added, followed by the addition of the compound 9-deoxo-9a-aza-9a-(γ-aminopropyl)-9a-homoerythromycin A (60 mg; 0.076 mmole) and 1-(3-dimethylaminopropyl)-3-ethyl-carbodiimide hydrochloride (57.6 mg, 0.30 mmol). The reaction mixture was stirred in a flow of argon at room temperature for 24 hours and then evaporated to a smaller volume under reduced pressure and purified on a silica gel column (eluent: CHCl$_3$:CH$_3$OH: NH$_4$OH=6:1:0.1). 14 mg of compound 1 was obtained; MS (m/z): 1527.3 [MH]$^+$. IR(cm$^{-1}$)/KBr: 3415, 2969, 2939, 2874, 1664, 1528, 1458, 1378, 1262, 1168, 1107, 1054, 1013, 959, 894, 803, 702.

After 10 min the resin was filtered and washed ten times with DCM, DMF and methanol.

Deprotection

Different solutions of piperidine in DMF were prepared and poured over the beads as follows:

| | |
|---|---|
| 5% piperidine/DMF | 10 min (~10 ml) |
| 30% piperidine/DMF | 15 min (~10 ml) |
| 50% piperidine/DMF | 30 min (~10 ml) |

After deprotection the resin was washed with DMF.

The second aminoacid, Fmoc-Leucine(1060 mg, 3 mmol) and 2-(1H-Benzotriazole-1yl)-1,1,3,3-tetramethyluron hexafluorophosphate (HBTU) was dissolved in 3 mL of DMF and with 0.216 mL ( 5 mmol) of DIPEA were added rapidly and simultaneously to the monomer/resin mixture in the reaction tube.

End Capping:

Solution of 10 eq ( 2.04 ml) of acetic anhydride and 10 eq (3.48 ml) of DIPEA in 5 ml of DMF was prepared. 2.5 ml of this solution was added to the reaction mixture for 5 min.

The second aminoacid was deprotected with a solution of piperidine in DMF as follows:

| | |
|---|---|
| 30% piperidine/DMF | 2 min (~10 ml) |
| 30% piperidine/DMF | 2 min (~10 ml) |
| 30% piperidine/DMF | 5 min (~10 ml) |
| 30% piperidine/DMF | 5 min (~10 ml) | and washed with a big amount of DMF.

The same procedure of coupling an deprotecting was repeated for the third amino acid:

| | |
|---|---|
| Fmoc-phenylalanine, 1162 mg, 3 mmol | |
| HBTU, 1081 mg | /3 ml DMF |
| DIPEA, 0.87 ml | |
| and the fourth amino acid: | |
| Fmoc-glycine, 892 mg, 3 mmol | |
| HBTU, 1081 mg | /3 ml DMF |
| DIPEA, 0.87 ml | | only after coupling of the fourth amino acid the Fmoc protecting group was not removed.

After filtration and washing with DMF product was removed from the resin:

10 ml of a solution of 50% trifluoroacetic acid in DCM was poured over the beads and mixed for 15 min. Reagents was removed by filtration and the beads were washed 2× with DCM. The same procedure was repeated with the next 10 ml of acid.

Collected solvent was evaporated removing the exces of TFA with adding amount of diethylether. 109.1 mg of intermediate B1 was isolated. MS (m/z): 715,6 [MH]$^+$ Intermediate B1

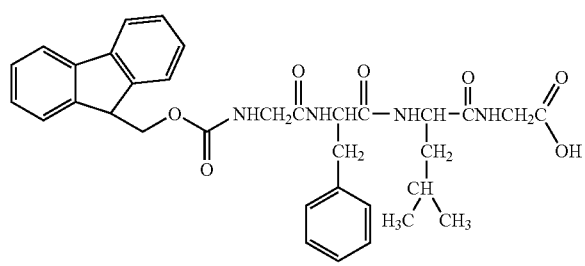

2-Chlorotritylchloride resin (1 eq=0.352 mmol, 326 mg) was placed in a glass column fitted with a coarse glass frit filter and swelled in DCM for 10 min. Then the resin was filtered and washed three times with DCM After washing with DMF the resin was loaded with a compound itermediate B1 by addition of 259 mg (0.422 mmol) disolved in 2 ml of DMF and 0.150 ml of N,N-diisopropylethylamine (DIPEA) and mixed. After 5 min 0.230 ml of DIPEA was added. After mixing for 50 min amount of 0.355 ml of methanol was added. After 10 min the resin was filtered and washed ten times with DCM, DMF and methanol.

Deprotection

Different solutions of piperidine in DMF were prepared and poured over the beads as follows:

| | |
|---|---|
| 5% piperidine/DMF | 10 min (~10 ml) |
| 30% piperidine/DMF | 15 min (~10 ml) |
| 50% piperidine/DMF | 30 min (~10 ml) |

After deprotection the resin was washed with DMF.

377 mg ( 1.055 mmol) of indomethacin, and 533 mg (1.41 mmol) of 2-(1-H-Benzotriazole-1yl)-1,1,3,3-tetramethyluronium hexafluorophosphate (HBTU) was dissolved in 3 mL of DMF and with 0.602 mL (3.52 mmol) of DIPEA were added rapidly and simultaneously to the polymer/resin mixture in the reaction tube.

End Capping:

Solution of 0.5 ml of acetic anhydride and 0.5 ml of DIPEA in 3 ml of DMF was added to the reaction mixture for 5 min, filtered and washed with DCM, DMF and MeOH.

Cleavage From the Resin 10 ml of a solution of 50% trifluoroacetic acid in DCM was poured over the beads and mixed for 15 min. Reagents was removed by filtration and the beads were washed 2× with DCM. The same procedure was repeated with the next 10 ml of acid.

Collected solvent was evaporated removing the exces of TFA with adding amount of diethylether. 210.8 mg of product intermediate B was isolated. MS (m/z): 732,66 [MH]$^+$

Example II

Compound 2
(Indomethacin-Gly-Phe-Leu-Gly-Azithromycin)

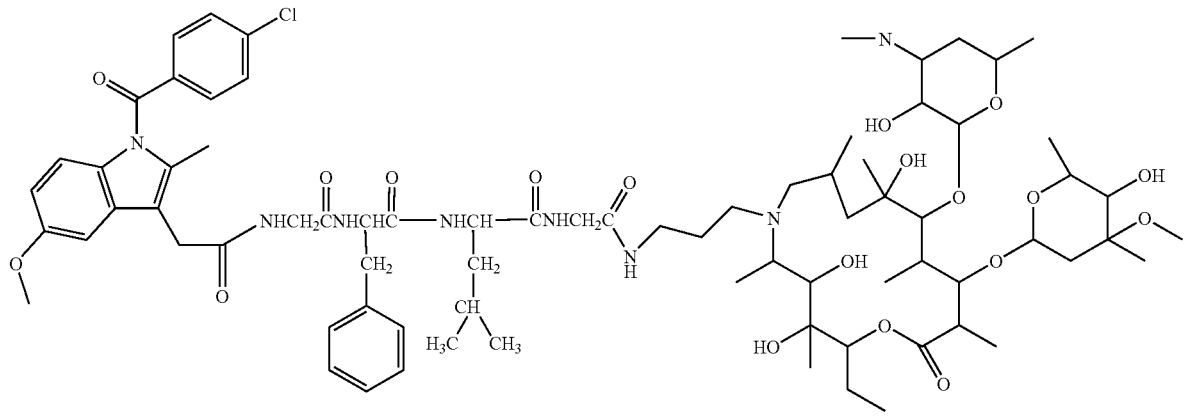

Intermediate B (200 mg; 0.27 mmol) was dissolved in dry CH$_2$Cl$_2$ (5 mL) in an inert atmosphere. 0.416 mL (2.14 mmol) of N,N-diisopropylethylamine and 74 mg (0.55 mmol) of 1-hydroxybenzotriazole were added, followed by the addition of the compound 9-deoxo-9a-aza-9a-(γ-aminopropyl)-9a-homoerythromycin A (216.6 mg; 0.27 mmole) and 1-(3-dimethylaminopropyl)-3-ethyl-carbodiimide hydrochloride (188 mg, 1.09 mmol). The reaction mixture was stirred in a flow of argon at room temperature for 24 hours and then evaporated to a smaller volume under reduced pressure and purified on a silica gel column (eluent: CHCl$_3$:CH$_3$OH:NH$_4$OH=6:1:0.1). 70 mg of compound 2 was obtained; MS (m/z): 1505.8 [MH]$^+$. IR(cm$^{-1}$)/KBr: 3654, 3633, 3425, 3084, 2970, 2936, 1720, 1652, 1637, 1545, 1439, 1368, 1309, 1230, 1179, 1111, 1089, 1055, 1013, 867, 803, 739, 700, 643.

Example III

Following the general procedure of example I and substituting therein the appropriate reactants affords the following compounds:

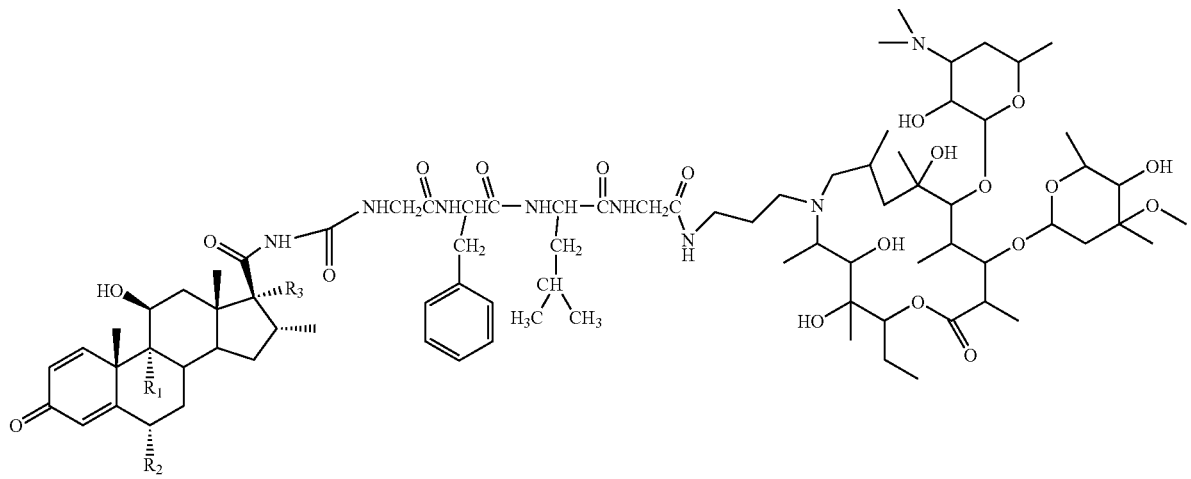

Compound 3: R$_1$=F; R$_2$=F; R$_3$=OH
Compound 4: R$_1$=F; R$_2$=H; R$_3$=H
Compound 5: R$_1$=F; R$_2$=F; R$_3$=H
Compound 6: R$_1$=H; R$_2$=F; R$_3$=OH

Example IV

Following the general procedure of example II and substituting therein the appropriate reactants affords the following compounds:

V-Gly-Phe-Leu-Gly-M

| Compound | V |
|---|---|
| 7 | [structure: ibuprofen] |
| 8 | [structure: flurbiprofen] |
| 9 | [structure: naproxen] |
| 10 | [structure: ketoprofen] |
| 11 | [structure: 2-acetylbenzoic acid] |
| 12 | [structure: sulindac] |
| 13 | [structure: etodolac] |
| 14 | [structure: ketorolac] |
| 15 | [structure: suprofen-like / tiaprofenic acid] |
| 16 | [structure: flunixin-like] |
| 17 | [structure: diclofenac sodium] |
| 18 | [structure: tolmetin sodium analog] |

Example V

Compound 19

To a solution of paclitaxel succinate (1 equivalent) in dry $CH_2Cl_2$ (5 ml) under argon, is added 9 equivalent of triethylamine, 2 equivalent of 1-hydroxybenzotriazole, 1 equivalent of 9-deoxo-9a-aza-9a-(γ-aminopropyl)-9a-homoerythromycin A and 4 equivalent of 1-(3-dimethylaminopropyl)-3-ethyl-carbodiimide hydrochloride. The reaction mixture is stirred for 24 hours at room temperature in a flow of argon, then is evaporated to a smaller volume under reduced pressure and purified on a silica gel column, using chloroform, methanol and ammonia as eluants. The chromatographed product is characterized by the structural formula:

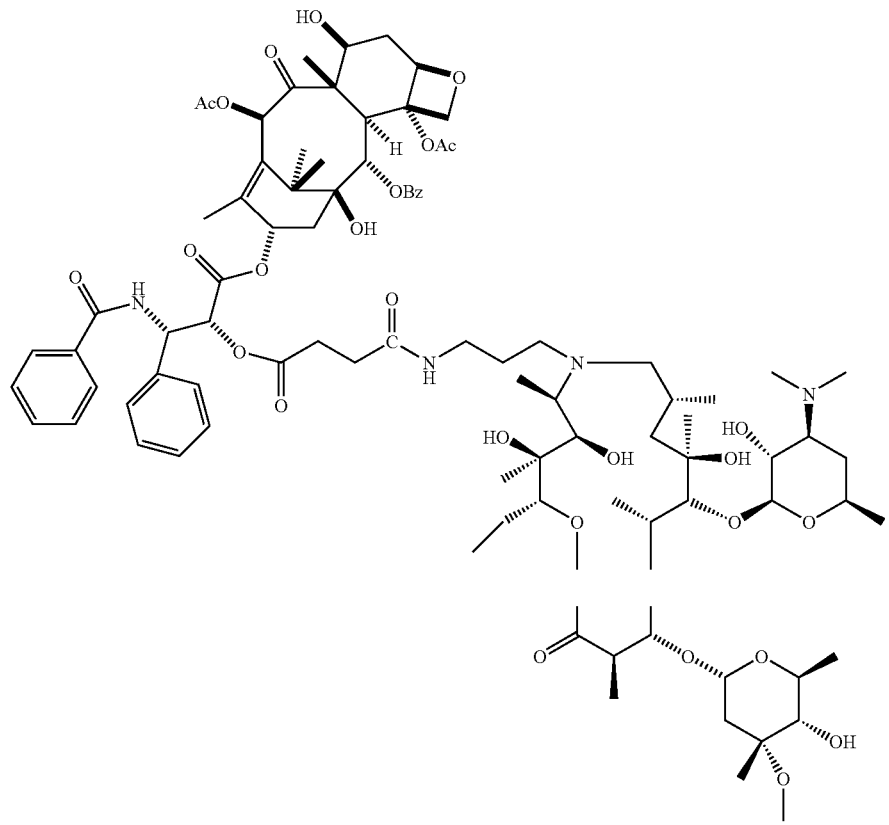

Example VI

Compound 20

To a solution of camptothecin succinate (1 equivalent) in dry $CH_2Cl_2$ (5 ml) under argon, is added 9 equivalent of triethylamine, 2 equivalent of 1-hydroxybenzotriazole, 1 equivalent of 9-deoxo-9a-aza-9a-(γ-aminopropyl)-9a-homo-erythromycin A and 4 equivalent of 1-(3-dimethylaminopropyl)-3-ethyl-carbodiimide hydrochloride. The reaction mixture is stirred for 24 hours at room temperature in a flow of argon, then is evaporated to a smaller volume under reduced pressure and purified on a silica gel column, using chloroform, methanol and ammonia as eluants. The chromatographed product is characterized by the structural formula:

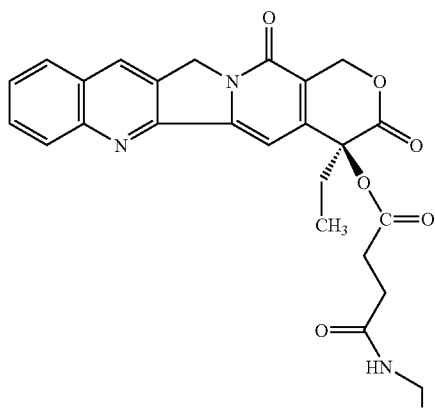

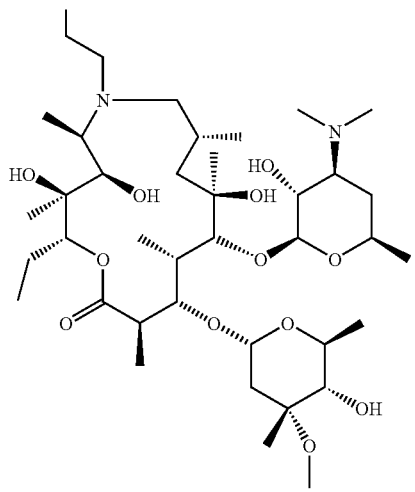

Example VII

Compound 21

To a solution of γ-methyl-N'-[4-[N-[(2,4-diamino-6-pteridinyl)methyl]-N-methylamino]benzoyl]-L-glutamate (1 equivalent) in dry DMF under argon is added 2 equivalent of 1,1-carbonyldiimidazole (in 5 ml of DMF). The reaction mixture is stirred for 24 hours at −5° C., then is added 1 equivalent of compound 9-deoxo-9a-aza9a-(γ-hydro A in dry DMF. The reaction mixture is heated 48 hours at 100° C., then is evaporated and purified on a silica gel column, using chloroform, methanol and ammonia as eluants. The chromatographed product is characterized by the structural formula:

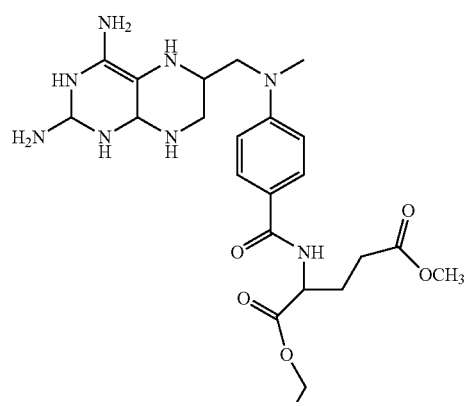

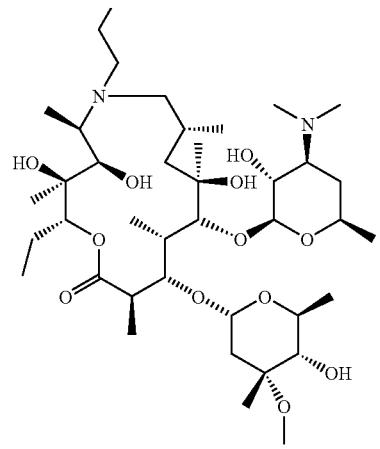

Example VIII

Compound 22

To a solution of 5'-O-succinylzidovudine (1 equivalent) in dry $CH_2Cl_2$ (5 ml) under argon, is added 9 equivalent of triethylamine, 2 equivalent of 1-hydroxybenzotriazole, 1 equivalent of 9-deoxo-9a-aza-9a-(γ-aminopropyl)-9a-homo-erythromycin A and 4 equivalent of 1-(3-dimethylaminopropyl)-3-ethyl-carbodiimide hydrochloride. The reaction mixture is stirred for 24 hours at room temperature in a flow of argon, then is evaporated to a smaller volume under reduced pressure and purified on a silica gel column, using chloroform, methanol and ammonia as eluants. The chromatographed product is characterized by the structural formula:

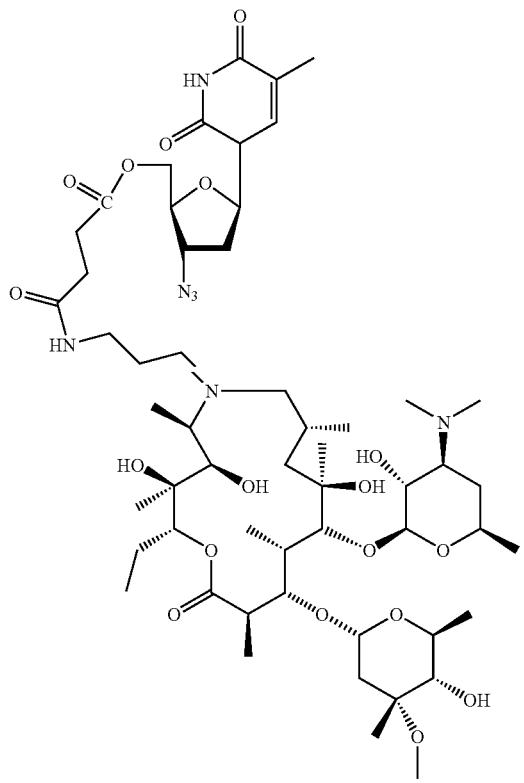

Abbreviations:
Pyr: pyridine
NEt₃: triethylamine
4-PP: 4-pyrrolopyridine
DMAP: 2,6-dimethylaminopyridine
DIPEA: N,N'-diisopropylethylamine
DMF: dimethylformamide
TFA: trifluoroacetic acid

The invention claimed is:

1. A compound of the formula I:

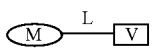

I wherein
M represents a group of Formula II:

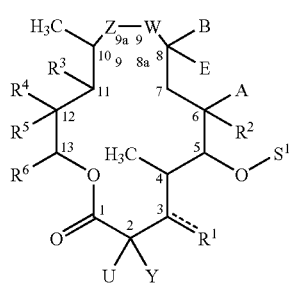

II wherein:

(i) Z and W independently are: $>C=O$, $>CH_2$, $>CH-NR_tR_s$, $>N-R_N$ or $>C=N-R_M$ or a bond wherein:
$R_t$ and $R_s$ independently are hydrogen or alkyl;
$R_M$ is hydroxy, alkoxy, substituted alkoxy or $OR^P$;
$R_N$ is hydrogen, $R^P$, alkyl, alkenyl, alkynyl, alkoxy, alkoxyalkyl, or $-C(X)-NR_tR_s$; wherein X is $=O$ or $=S$;
provided that Z and W cannot both simultaneously be, $>C=O$, $>CH_2$, $>CH-NR_tR_s$, $>N-R_N$ or $>C=N-R_M$ or a bond, (ii) U and Y independently are hydrogen, halogen, alkyl, or hydroxyalkyl;

(iii) $R^1$ is hydroxy, $OR^P$, $-O-S^2$ group or an $=O$;

(iv) $S^1$ is a sugar moiety of formula:

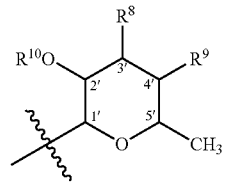

wherein
$R^8$ and $R^9$ are both hydrogen or together form a bond, or $R^9$ is hydrogen and $R^8$ is $-N(CH_3)R^y$, wherein $R^y$ is $R^P$, $R^z$ or $-C(O)R^z$ wherein $R^z$ is hydrogen or alkyl or alkenyl or alkynyl or cycloalkyl or aryl or heteroaryl or alkyl substituted with $C_2$-$C_7$-alkyl, $C_2$-$C_7$-alkenyl, $C_2$-$C_7$-alkynyl, aryl or heteroaryl
$R^{10}$ is hydrogen or $R^P$;

(v) $S^2$ is a sugar moiety of formula:

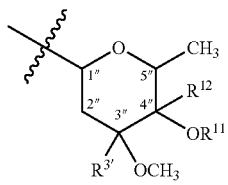

wherein:
$R^3$ is hydrogen or methyl;
$R^{11}$ is hydrogen, $R^P$ or $O-R^{11}$ is a group that with $R^{12}$ and with C/4" carbon atom forms a $>C=O$ or epoxy group;
$R^{12}$ is hydrogen or a group that with $O-R^{11}$ group and with C/4" carbon atom forms a $>C=O$ or epoxy group;

(vi) $R^2$ is hydrogen, hydroxy, $OR^P$ or alkoxy
(vii) A is hydrogen or methyl;
(viii) B is methyl or epoxy;
(ix) E is hydrogen or halogen;
(x) $R^3$ is hydroxy, $OR^P$, alkoxy or $R^3$ is a group that with $R^5$ and with C/11 and C/12 carbon atoms forms a cyclic carbonate or carbamate; or if W or Z is $>N-R_N$ $R^3$ is a group that with W or Z forms a cyclic carbamate;
(xi) $R^4$ is $C_1$-$C_4$ alkyl;
(xii) $R^5$ is hydrogen, hydroxy, $OR^P$, $C_1$-$C_4$-alkoxy, or a group that with $R^3$ and with C/11 and C/12 carbon atoms forms a cyclic carbonate or carbamate;
(xiii) $R^6$ is hydrogen or $C_1$-$C_4$-alkyl; and
$R^P$ is hydroxyl or amino protective group;

wherein M has a linkage site through which it is linked to V via linking group L; provided that the linkage site is at one or more of the following:
a) any reactive hydroxy, nitrogen, or epoxy group located on $S^1$, $S^2$, or an aglycone oxygen if $S^1$ or/and $S^2$ is cleaved off wherein if V is an antineoplastic subunit or an antiviral subunit, the linkage site is not on $S^1$;
b) a reactive >N—$R_N$ or —$NR_tR_s$ or =O group located on Z or W wherein if V is an antiviral subunit, Z or W is >C=O or >N—$R_N$;
c) a reactive hydroxy group located at any one of $R^1$, $R^2$, $R^3$, and $R^5$;
d)

V is chosen from the group consisting of (i) an anti-inflammatory steroid subunit of the Formula X:

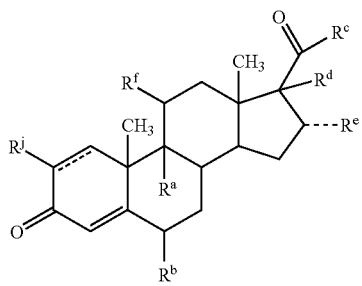

wherein
$R^a$ and $R^b$ independently represents, hydrogen or halogen;
$R^c$ is hydroxy, alkoxy, alkyl, thiocarbamoyl, carbamoyl or a valence-bond;
$R^d$ and $R^e$ independently represents: hydrogen, hydroxy, methyl or $C_1$–$C_4$-alkoxy or each are a group that forms a 1,3-dioxolane ring with the other or a valence bond;
$R^f$ is hydrogen, hydroxy, chloro, or forming a keto group with the carbon atom it is attached to;
$R^j$ is hydrogen or halogen;
(ii) a non-steroidal anti-inflammatory subunit derived from the NSAIDs selected from: aceclofenac, acemetacin, acetaminophen, acetaminosalol, acetyl-salicylic acid, acetyl-salicylic-2-amino-4-picoline-acid, 5-aminoacetylsalicylic acid, alclofenac, aminoprofen, amfenac, ampyrone, ampiroxicam, anileridine, bendazac, benoxaprofen, bermoprofen, α-bisabolol, bromfenac, 5-bromosalicylic acid acetate, bromosaligenin, bucloxic acid, butibufen, carprofen, celexocib, chromoglycate, cinmetacin, clindanac, clopirac, sodium diclofenac, diflunisal, ditazol, droxicam, enfenamic acid, etodolac, etofenamate, felbinac, fenbufen, fenclozic acid, fendosal, fenoprofen, fentiazac, fepradinol, flufenac, flufenamic acid, flunixin, flunoxaprofen, flurbiprofen, glutametacin, glycol salicylate, ibufenac, ibuprofen, ibuproxam, indomethacin, indoprofen, isofezolac, isoxepac, isoxicam, ketoprofen, ketorolac, lornoxicam, loxoprofen, meclofenamic acid, mefenamic acid, meloxicam, mesalamine, metiazinic acid, mofezolac, montelukast, nabumetone, naproxen, niflumic acid, nimesulide, olsalazine, oxaceprol, oxaprozin, oxyphenbutazone, paracetamol, parsalmide, perisoxal, phenyl-acetyl-salicylate, phenylbutazone, phenylsalicylate, pyrazolac, piroxicam, pirprofen, pranoprofen, protizinic acid, reserveratol, salacetamide, salicylamide, salicylamide-O-acetyl acid, salicylsulphuric acid, salicin, salicylamide, salsalate, sulindac, suprofen, suxibutazone, tamoxifen, tenoxicam, tiaprofenic acid, tiaramide, ticlopridine, tinoridine, tolfenamic acid, tolmetin, tropesin, xenbucin, ximoprofen, zaltoprofen, zomepirac, tomoxiprol, zafirlukast and cyclosporine;
(iii) an antineoplastic subunit derived from the antineoplastic compounds selected from bicaluatnide, camptothecin, estramustine phosphate, flutamide, mechlorethamine, thiotepa, ifosfamide, hydroxyurea, bleomycin, paclitaxel, lomustine, irinotecan, methotrexate, vinorelbine, anastrazole, floxuridine, melphalan, vincristine, vinblastine, mitomycin, nandrolone, goserelin, leuprolide, triptorelin, aminogluthetemide, mitotane, cisplatine, chlorambucil, pentostatin, cladribine, busulfan, etoposide, mitoxantrone, idarubicin, cyclophosphamide, mercaptopurine, thioguanine, cytarbine, cyclophosphamide, doxorubicin, daunoribicin, teniposide tamoxifen, taxotere and topotecan; and
(iv) an antiviral subunit derived from the anti-viral compounds selecting from aciclovir, famciclovir, ganciclovir, cidofovir, lamivudine, ritonavir, indinavir, nevirapine, zidovudine, didanosine, stavudine, abacavir, amprenavir, ribavirin and adamantane;
provided that when V is a steroid or non-steroidal anti-inflammatory subunit, L is a peptide; and
L is a linker molecule to which each of M and V are covalently linked; or a pharmaceutically acceptable salt or solvate thereof or an individual diastereoisomer thereof.

2. A compound of the formula I:

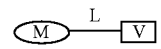

I wherein M represents a group of Formula II:

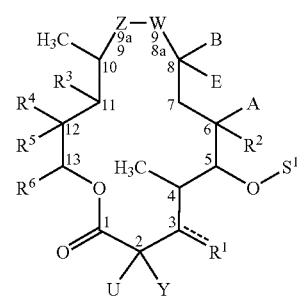

II wherein:
(i) Z and W independently are: >C=O, >$CH_2$, >CH—$NR_tR_s$, >N—$R_N$ or >C=N—$R_M$ or a bond wherein:
$R_t$ and $R_s$ independently are hydrogen or alkyl;
$R_M$ is hydroxy, alkoxy, substituted alkoxy or $OR^p$;
$R_N$ is hydrogen, $R^p$, alkyl, alkenyl, alkynyl, alkoxy, alkoxyalkyl, or —C(X)—$NR_tR_s$; wherein X is =O or =S;
provided that Z and W cannot both simultaneously be, >C=O, >$CH_2$, >CH—$NR_tR_s$, >N—$R_N$ or >C=N—$R_M$ or a bond,
(ii) U and Y independently are hydrogen, halogen, alkyl, or hydroxyalkyl;
(iii) $R^1$ is hydroxy, $OR^p$, —O—$S^2$ group or an =O;
(iv) $S^1$ is a sugar moiety of formula:

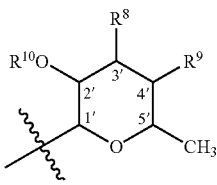

wherein
R⁸ and R⁹ are both hydrogen or together form a bond, or R⁹ is hydrogen and R⁸ is —N(CH₃)R^y, wherein R^y is R^p, R^z or —C(O)R^z wherein R^z is hydrogen or alkyl or alkenyl or alkynyl or cycloalkyl or aryl or heteroaryl or alkyl substituted with C₂–C₇-alkyl, C₂–C₇-alkenyl, C₂–C₇-alkynyl, aryl or heteroaryl R¹⁰ hydrogen or R^p;

(v) S² is a sugar moiety of formula:

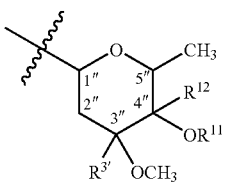

wherein:
R³ hydrogen or methyl;
R¹¹ is hydrogen, R^p or O—R¹¹ is a group that with R¹² and with C/4″ carbon atom forms a >C=O or epoxy group;
R² is hydrogen or a group that with O—R¹¹ group and with C/4″ carbon atom forms a >C=O or epoxy group;

(vi) R² is hydrogen, hydroxy, OR^p or alkoxy
(vii) A is hydrogen or methyl;
(viii) B is methyl or epoxy;
(ix) E is hydrogen or halogen;
(x) R³ is hydroxy, OR, alkoxy or R³ is a group that with R⁵ and with C/11 and C/12 carbon atoms forms a cyclic carbonate or carbamate; or if W or Z is >N—R_N R³ is a group that with W or Z forms a cyclic carbamate;
(xi) R⁴ is C₁–C₄ alkyl;
(xii) R⁵ is hydrogen, hydroxy, OR^p, C₁–C₄-alkoxy, or a group that with R³ and with C/11 and C/12 carbon atoms forms a cyclic carbonate or carbamate;
(xiii) R⁶ is hydrogen or C₁–C₄-alkyl; and
R^p is hydroxyl or amino protective group;
wherein M has a linkage site through which it is linked to V via linking group L; provided that the linkage site is at one or more of the following:
a) any reactive hydroxy, nitrogen, or epoxy group located on S¹, S², or an aglycone oxygen if S¹ or/and S² is cleaved off wherein if V is an antineoplastic subunit or an antiviral subunit, the linkage site is not on S¹;
b) a reactive >N—R_N or —NR_rR_s or =O group located on Z or W wherein if V is an antiviral subunit, Z or W is >C=O or >N—R_N;
c) a reactive hydroxy group located at any one of R¹, R², R³, and R⁵;
d)
wherein L is group of Formula IV:

$$X^1—(CH_2)_m—Q—(CH_2)_n—X^2 \qquad IV$$

wherein
X¹ is selected from: —CH₂—, —C(O)—, OC(O)—, N—O—, —OC(O)NH— or —C(O)NH—;
X² is —NH— or —NHC(O)—, —OC(O)—, —C(O)—, —O or —CH₂—;
Q is —NH— or —CH₂—, or absent;
wherein each —CH₂— or —NH— group is optionally substituted by C₁–C₇-alkyl, C₂–C₇-alkenyl, C₂–C₇-alkynyl, C(O)R^x, C(O)OR^x, C(O)NHR^x wherein R^x may be C₁–₇-alkyl, aryl or heteroaryl;
the symbols m and n independently are a whole number from 0 to 4, with the proviso that if Q is NH, n cannot be 0,
with proviso that if L is group of Formula IV, V is an antineoplastic subunit or an antiviral subunit; or
L represents a polypeptide of between about two and about 50 amino acids joined together;
wherein V is selected from the group consisting of (i) an antiinflammatory steroid subunit of the Formula X:

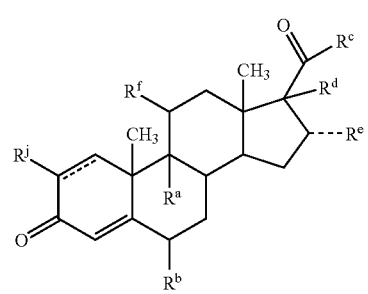

wherein
R^a and R^b independently represents, hydrogen or halogen;
R^c is hydroxy, alkoxy, alkyl, thiocarbamoyl, carbamoyl or a valence-bond;
R^d and R^e independently represents: hydrogen, hydroxy, methyl or C₁–C₄-alkoxy or each are a group that forms a 1,3-dioxolane ring with the other or a valence bond;
R^f is hydrogen, hydroxy, chloro, or forming a keto group with the carbon atom it is attached to;
R^j is hydrogen or halogen;
(ii) NSAID selected from the group consisting of: aceclofenac, acemetacin, acetaminophen, acetaminosalol, acetyl-salicylic acid, acetyl-salicylic-2-amino-4-picoline-acid, 5-aminoacetylsalicylic acid, alclofenac, aminoprofen, amfenac, ampyrone, ampiroxicam, anileridine, bendazac, benoxaprofen, bermoprofen, α-bisabolol, bromfenac, 5-bromosalicylic acid acetate, bromosaligenin, bucloxic acid, butibufen, carprofen, celexocib, chromoglycate, cinmetacin, clindanac, clopirac, sodium diclofenac, diflunisal, ditazol, droxicam, enfenamic acid, etodolac, etofenamate, felbinac, fenbufen, fenclozic acid, fendosal, fenoprofen, fentiazac, fepradinol, flufenac, flufenamic acid, flunixin, flunoxaprofen, flurbiprofen, glutametacin, glycol salicylate, ibufenac, ibuprofen, ibuproxam, indomethacin, indoprofen, isofezolac, isoxepac, isoxicam, ketoprofen, ketorolac, lornoxicam, loxoprofen, meclofenamic acid, mefenamic acid, meloxicam, mesalamine, metiazinic acid, mofezolac, montelukast, nabumetone, naproxen, niflumic acid, nimesulide, olsalazine, oxaceprol, oxaprozin, oxyphenbutazone, paracetamol, parsalmide, perisoxal, phenyl-acetyl-salicylate, phenylbutazone, phenylsalicylate, pyrazolac, piroxicam, pirprofen, pranoprofen, protizinic acid, reserveratol, salacetamide, salicylamide, salicylamide-O-acetyl acid, salicylsulphuric acid, salicin, salicylamide, salsalate, sulindac, suprofen, suxibutazone, tamoxifen, tenoxicam, tiaprofenic acid, tiaramide, ticlopridine, tinoridine, tolfenamic acid, tolmetin, tropesin, xenbucin, ximoprofen, zaltoprofen, zomepirac, tomoxiprol, zafirlukast and cyclosporine;

(iii) an antineoplastic compound selected from the group consisting of bicaluatnide, camptothecin, estramustine phosphate, flutamide, mechiorethamine, thiotepa, ifosfamide, hydroxyurea, bleomycin, paclitaxel, lomustine, irinotecan, methotrexate, vinorelbine, anastrazole, floxuridine, melphalan, vincristine, vinblastine, mitomycin, nandrolone, goserelin, leuprolide, triptorelin, aminogluthetemide, mitotane, cisplatine, chlorambucil, pentostatin, cladribine, busulfan, etoposide, mitoxantrone, idarubicin, cyclophosphamide, mercaptupurine, thioguanine, cytarbine, cyclophosphamide, doxorubicin, daunoribicin, teniposide tamoxifen, taxotere and topotecan; and (iv) an anti-viral compound selected from the group consisting of aciclovir, famciclovir, ganciclovir, cidofovir, lamivudine, ritonavir, indinavir, nevirapine, zidovudine, didanosine, stavudine, abacavir, amprenavir, ribavirin and adamantane;

or a pharmaceutically acceptable salt or solvate of any of the foregoing.

3. A compound according to claim 2 wherein Z and W together are: —N(CH$_3$)—CH$_2$—, —NH—CH$_2$—, —CH$_2$—NH—, —C(O)—NH— or —NH—C(O)—;

A and B are methyl;
B is hydrogen;
E is hydrogen;
R$^2$ is hydroxy or methoxy;
S$^1$ represents desosamine sugar wherein R$^8$ is selected from: hydrogen, methyl, amino, C$_1$–C$_6$ alkylamino or C$_1$–C$_6$ dialkylamino;

R$^9$ R$^{10}$ are hydrogen;
R$^1$ is hydroxy or the O—S$^2$ group wherein the S$^2$ represents a cladinose sugar wherein:
R$^{11}$ is hydrogen, or O—R$^{11}$ is a group that with R$^{12}$ and with C/4" carbon atom forms a >C=O or epoxy group;
R$^{12}$ is hydrogen or a group that with O—R$^{11}$ and with C/4" carbon atom forms a >C=O or or epoxy group;
R$^{13}$ is methyl;
U is hydrogen;
Y is methyl;
R$_6$ is hydroxy, methyl or ethyl;
R$^5$ is hydrogen, hydroxy, methoxy or a group that with R$^3$ and with C/11 and C/12 carbon atoms forms a cyclic carbonate or carbamate bridge;
R$^3$ is hydroxy or a group that forms a cyclic carbamate bridge with W or Z, or R$^3$ is a group that with R$^5$ and with C/11 and C/12 carbon atoms forms a cyclic carbonate or carbamate bridge;
R$^4$ methyl;
provided that the linkage is through the nitrogen of Z at N/9a position or through the carbon of R$^{12}$ or through the oxygen of R$^{11}$ both at C/4" position of the S$^2$ sugar.

4. A compound according to claim 2 wherein
X$^1$ is —CH$_2$— or —OC(O)—;
X is —NHC(O)—;
Q is —NH— or absent.

5. A compound according to claim 2 wherein: V is derived from a NSAID selecting from: S-(+)-ibuprofen, indomethacin, flurbiprofen, naproxen, ketoprofen, acetyl salicylic acid, sulindac, etodolac, ketorolac, suprofen, flunixin, diclofenac sodium and tolmetin sodium.

6. A compound according to claim 2 wherein:
V is derived from an antineoplastic compounds selecting from: methotrexate, paclitaxel, camptothecin and doxorubicin.

7. A compound according to claim 2 wherein
V is derived from the anti-viral compounds selected from: the group consising of: zidovudine, didanosine and stavudine.

8. A compound of the Formula:

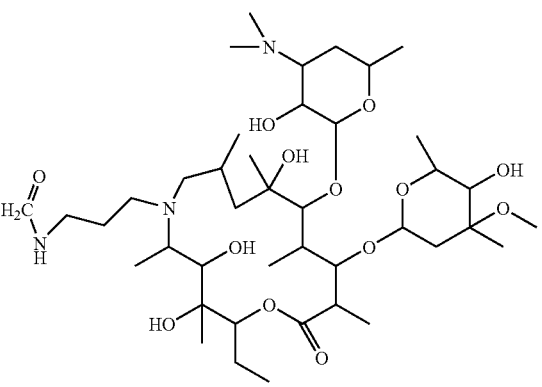
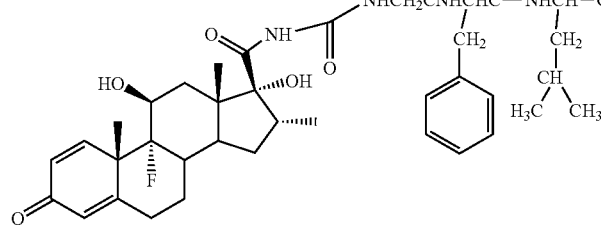

or a pharmaceutically acceptable salt or solvate thereof.

9. A compound of the Formula:
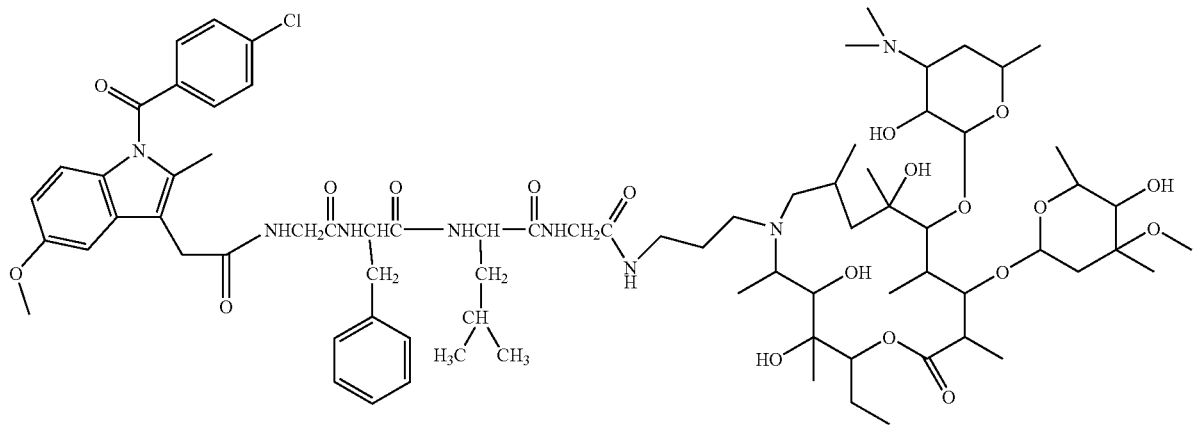
or a pharmaceutically acceptable salt or solvate thereof.
10. A compound of the Formula:
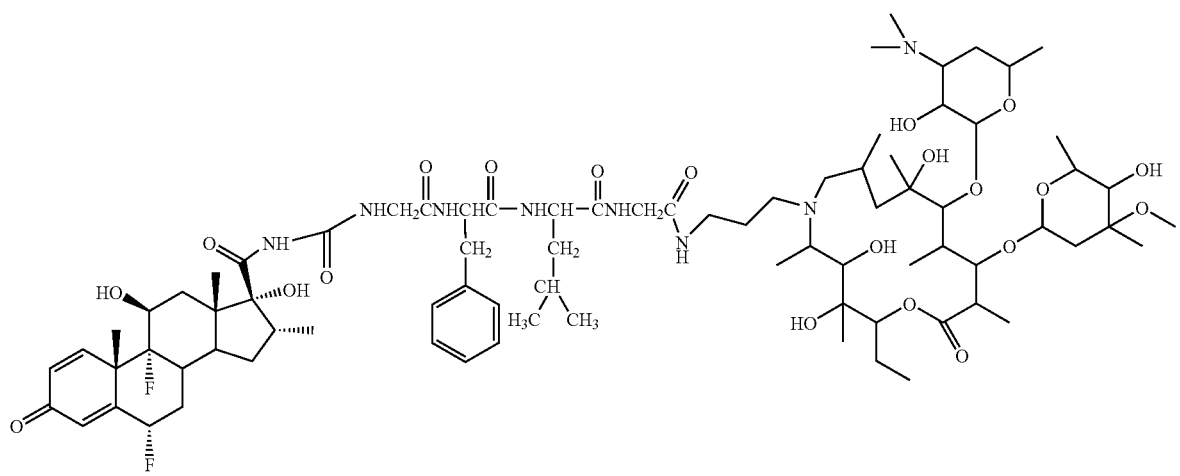
or a pharmaceutically acceptable salt or solvate thereof.
11. A compound of the Formula:
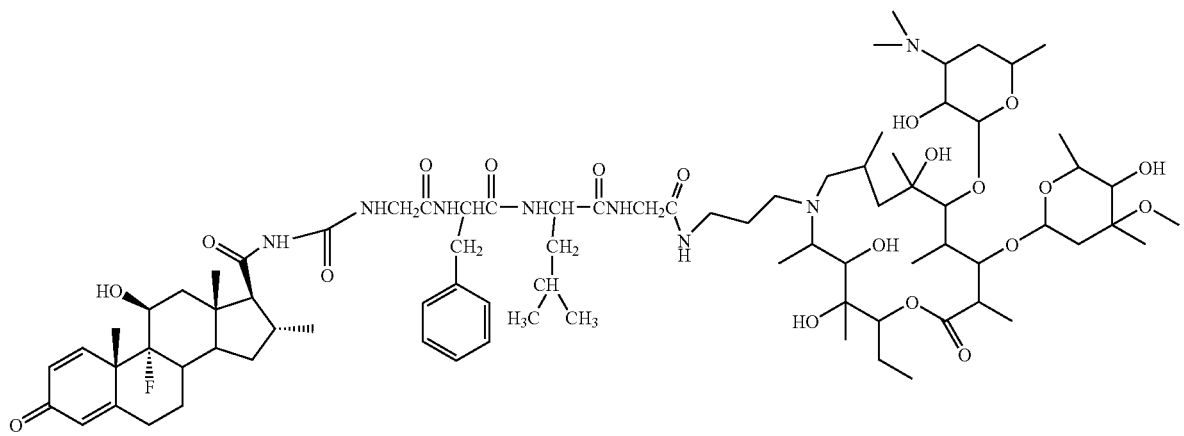
or a pharmaceutically acceptable salt or solvate thereof.

12. A compound of the Formula:
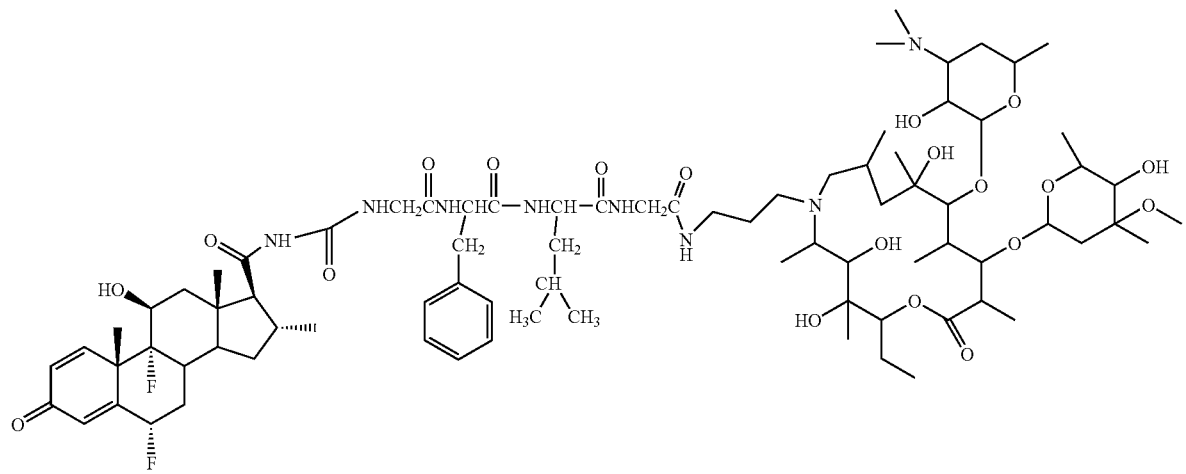
or a pharmaceutically acceptable salt or solvate thereof.
13. A compound of the Formula:
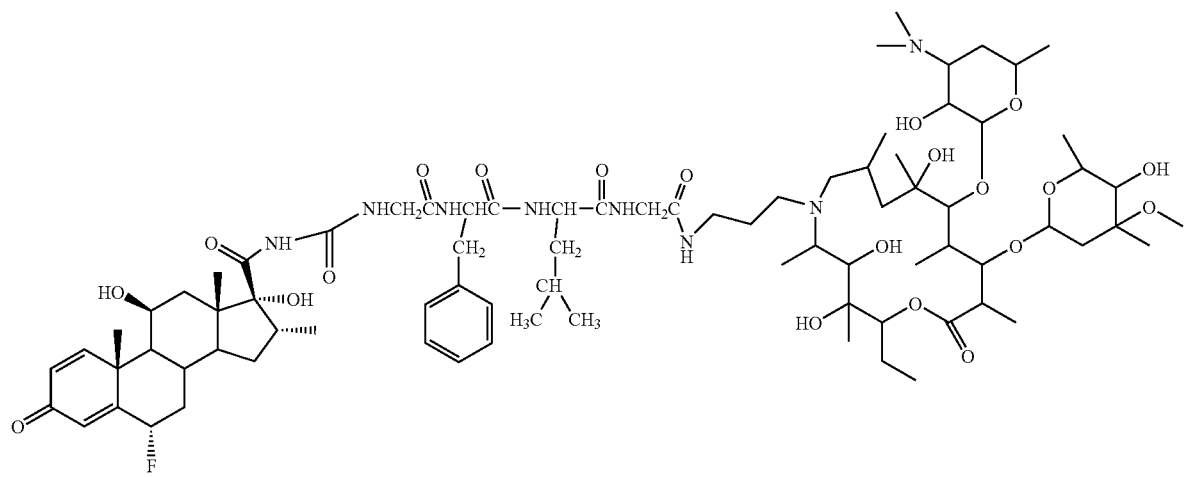
or a pharmaceutically acceptable salt or solvate thereof.
14. A compound of the Formula:
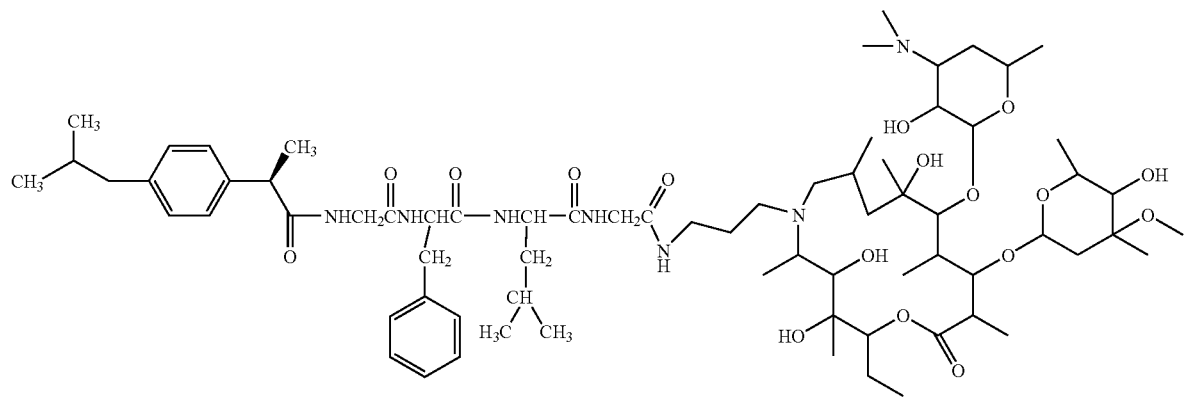
or a pharmaceutically acceptable salt or solvate thereof.

15. A compound of the Formula:
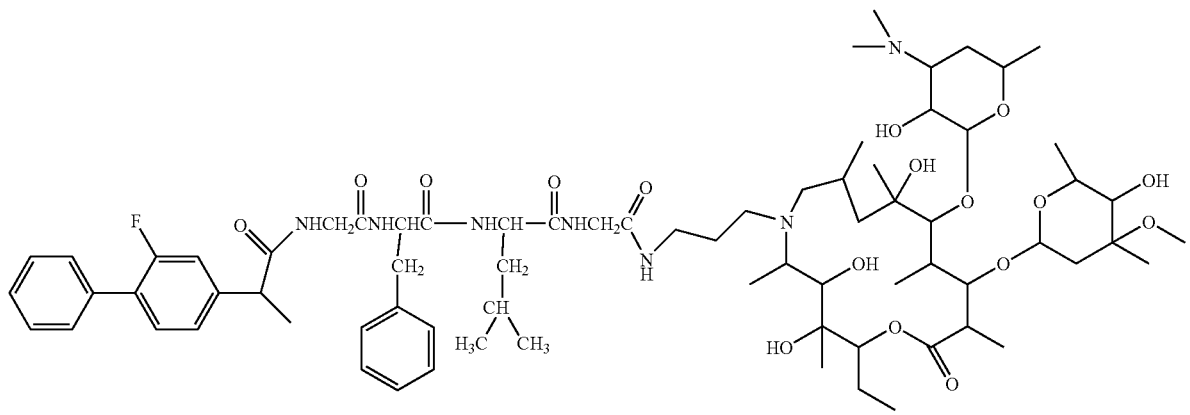
or a pharmaceutically acceptable salt or solvate thereof.
16. A compound of the Formula:
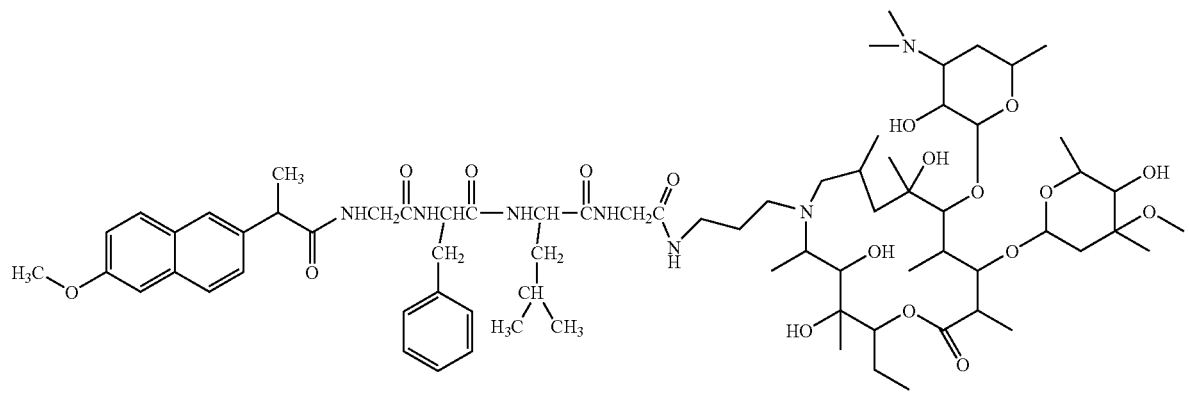
or a pharmaceutically acceptable salt or solvate thereof.
17. A compound of the Formula:
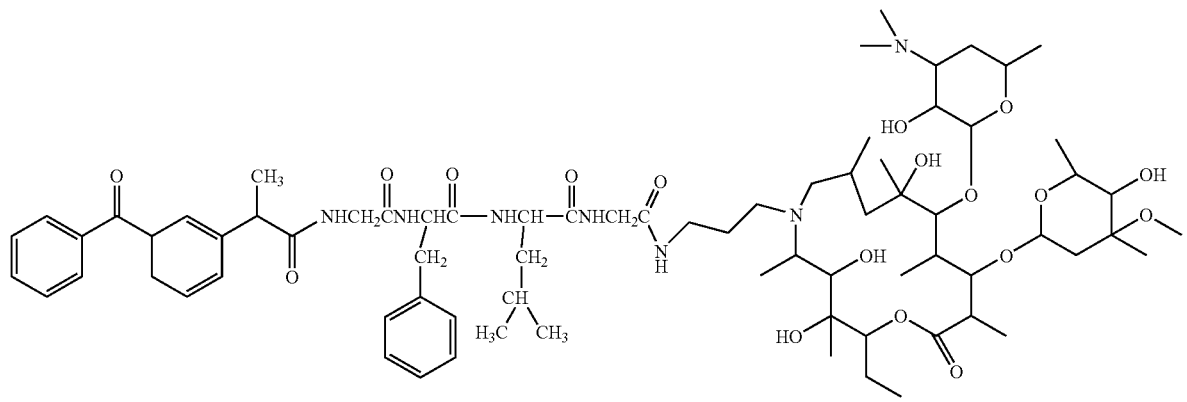
or a pharmaceutically acceptable salt or solvate thereof.

18. A compound of the Formula:
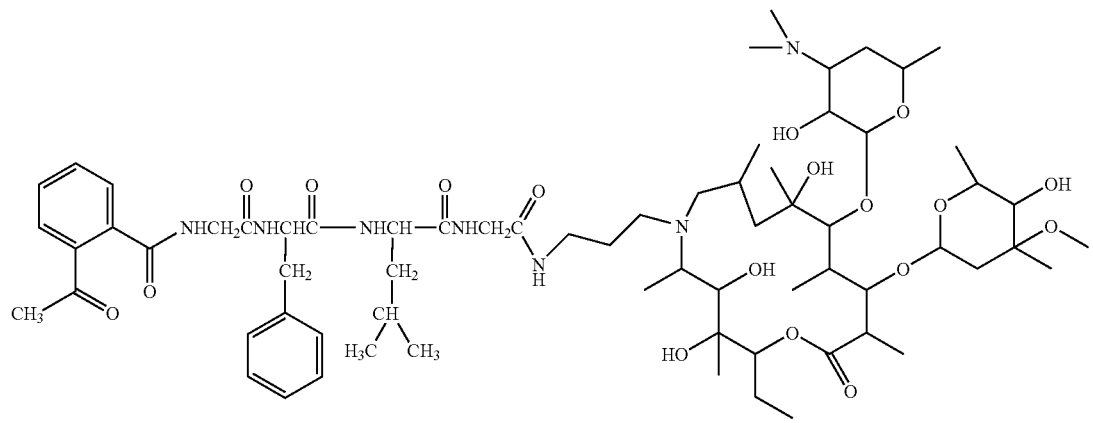
or a pharmaceutically acceptable salt or solvate thereof.
19. A compound of the Formula:
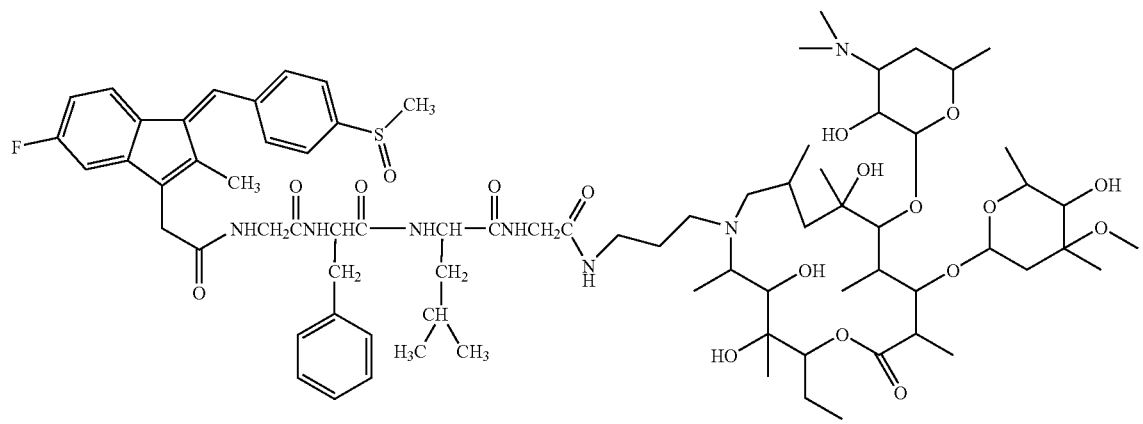
or a pharmaceutically acceptable salt or solvate thereof.
20. A compound of the Formula:
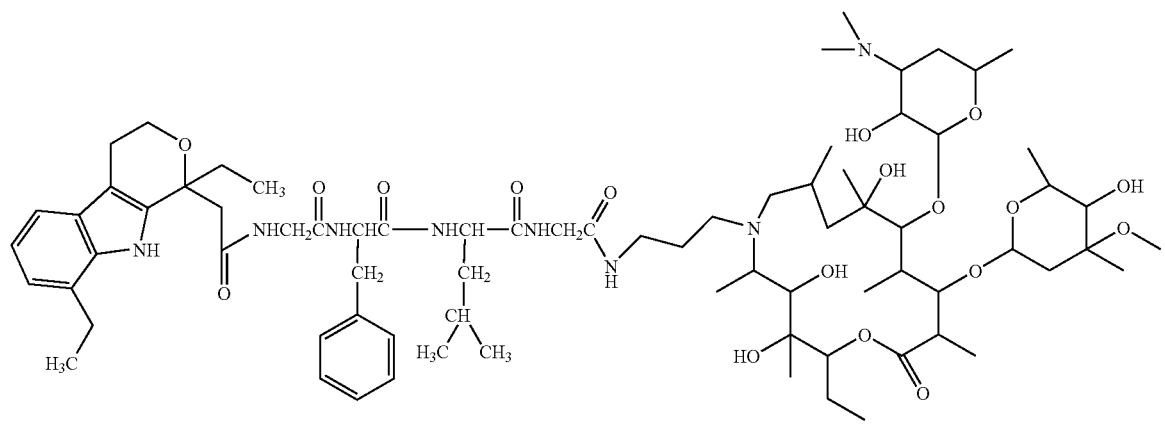
or a pharmaceutically acceptable salt or solvate thereof.

21. A compound of the Formula:
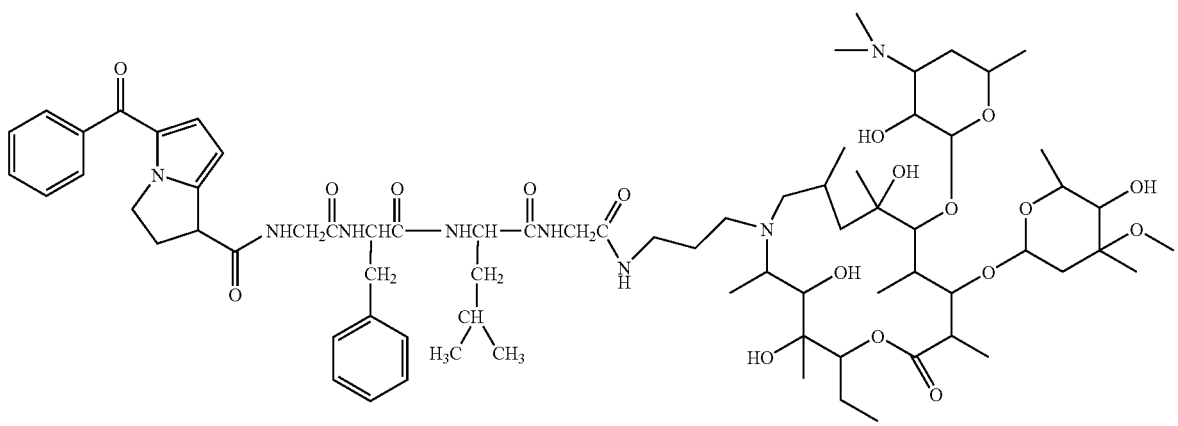
or a pharmaceutically acceptable salt or solvate thereof.
22. A compound of the Formula:
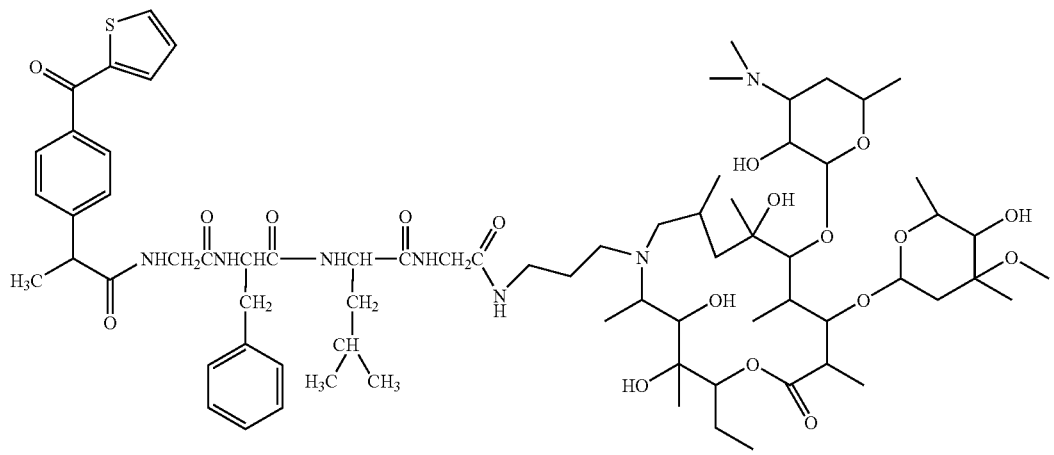
or a pharmaceutically acceptable salt or solvate thereof.
23. A compound of the Formula:
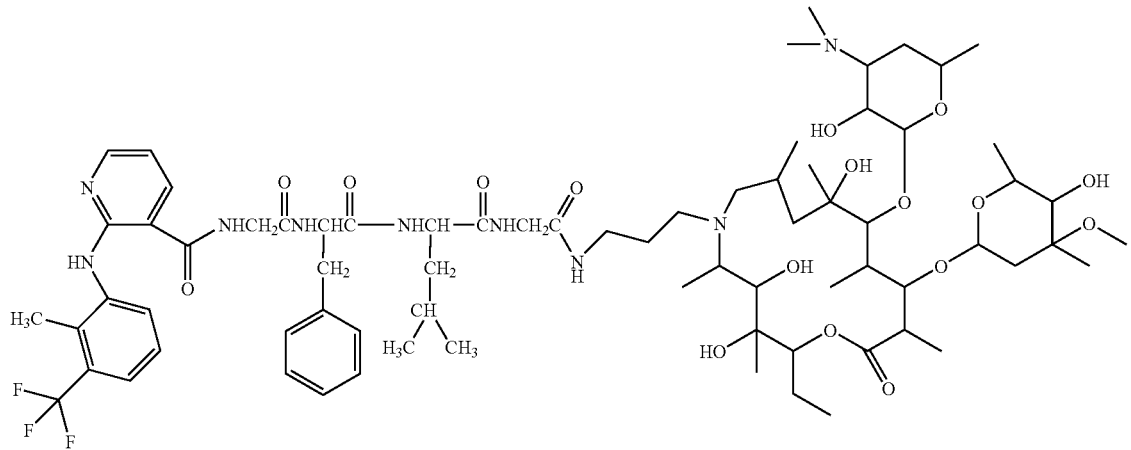
or a pharmaceutically acceptable salt or solvate thereof.

24. A compound of the Formula:
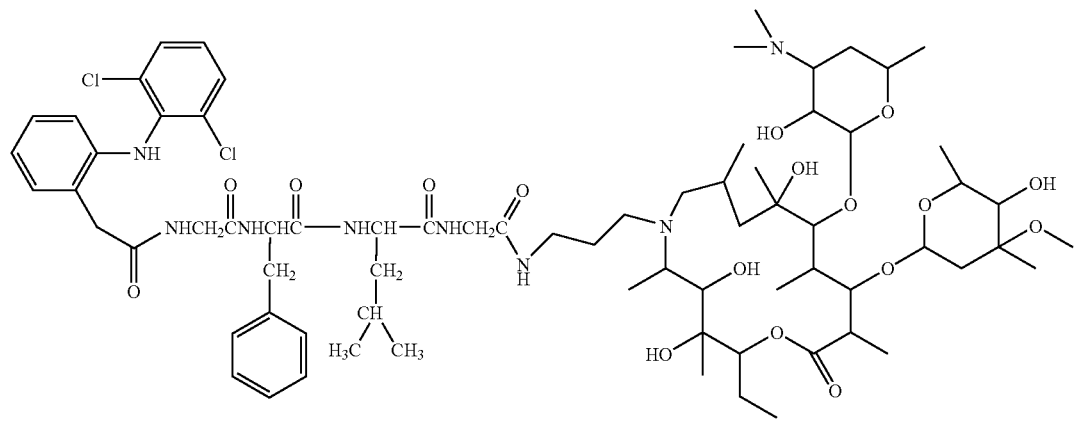
or a pharmaceutically acceptable salt or solvate thereof.
25. A compound of the Formula:
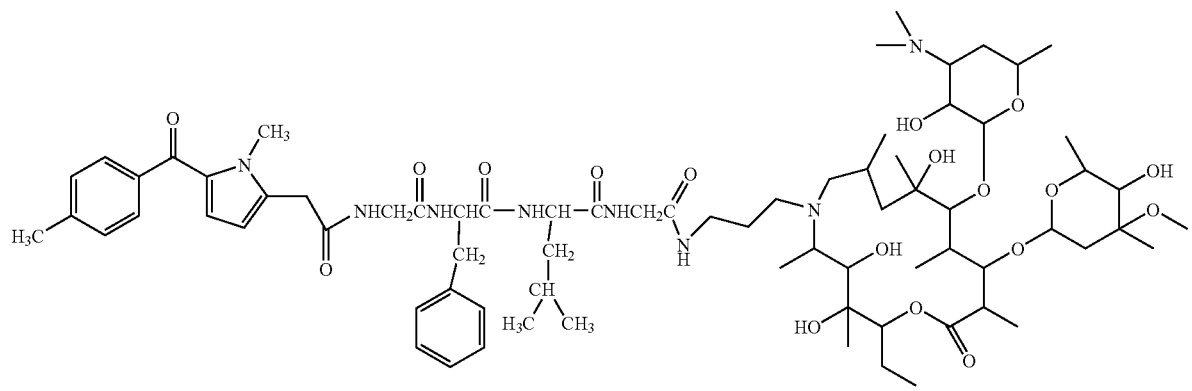
or a pharmaceutically acceptable salt or solvate thereof.
26. A compound of the Formula:
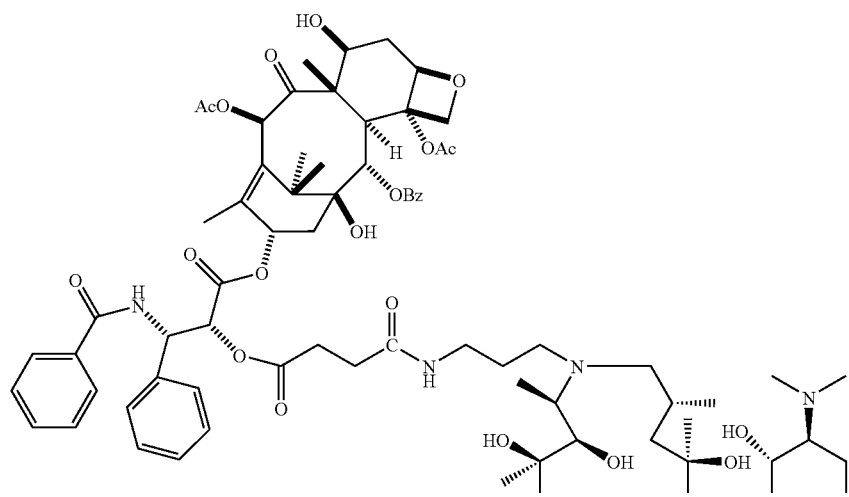

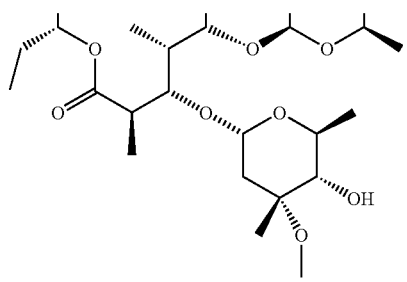
or a pharmaceutically acceptable salt or solvate thereof.
27. A compound of the Formula:
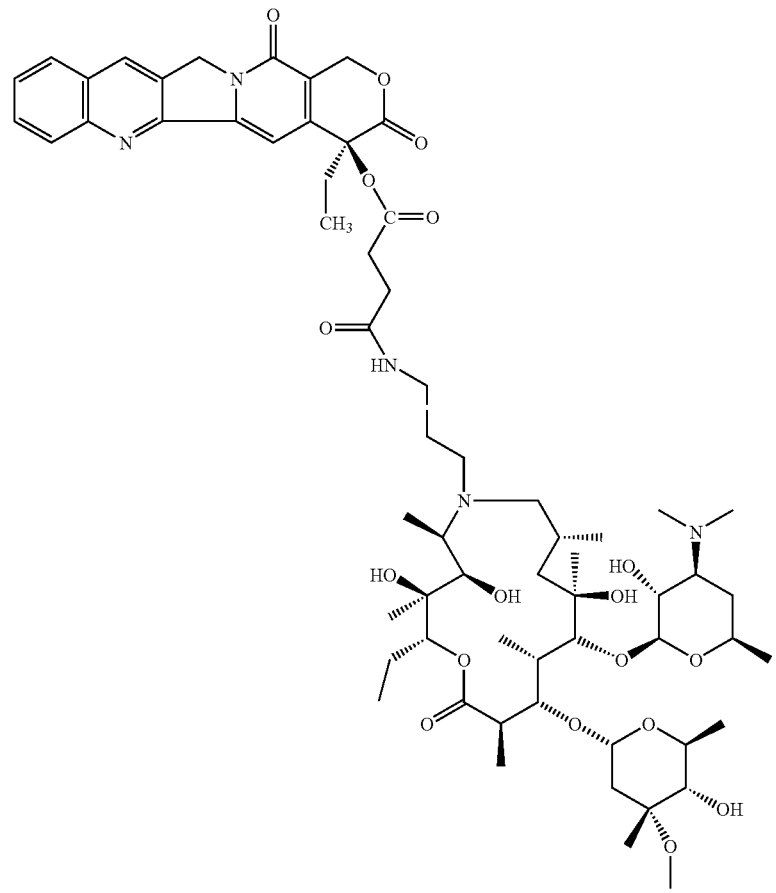
or a pharmaceutically acceptable salt or solvate thereof.

28. A compound of the Formula:

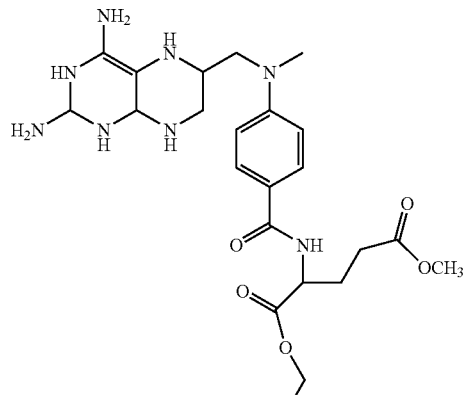

or a pharmaceutically acceptable salt or solvate thereof.

29. A compound of the Formula:

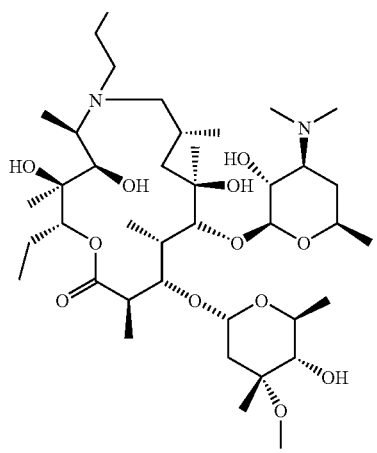

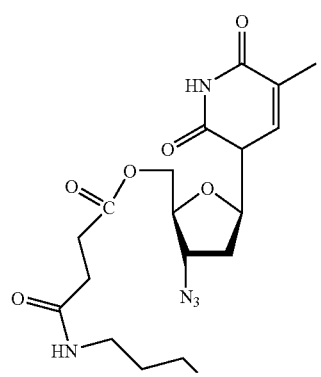

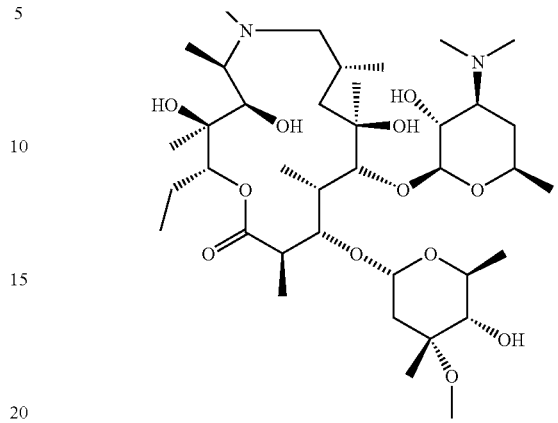

or a pharmaceutically acceptable salt or solvate thereof.

30. Process for the preparation of a compound of Formula I

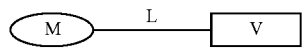

M represents a group of Formula II:

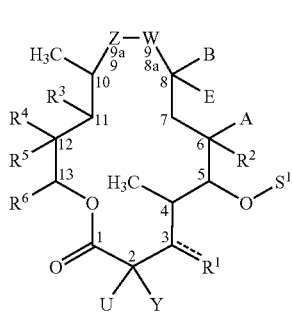

wherein:
(i) Z and W independently are: >C═O, >CH$_2$, >CH—NR$_t$R$_s$, >N—R$_N$ or >C═N—R$_M$ or a bond wherein:
R$_t$ and R$_s$ independently are hydrogen or alkyl;
R$_M$ is hydroxy, alkoxy, substituted alkoxy or OR$^P$;
R$_N$ is hydrogen, R$^P$, alkyl, alkenyl, alkynyl, alkoxy, alkoxyalkyl, or —C(X)—NR$_t$R$_s$; wherein X is ═O or ═S;
provided that Z and W cannot both simultaneously be, >C═O, >CH$_2$, >CH—NR$_t$R$_s$, >N—R$_N$ or >C═N—R$_M$ or a bond,
(ii) U and Y independently are hydrogen, halogen, alkyl, or hydroxyalkyl;
(iii) R$^1$ is hydroxy, OR$^P$, —O—S$^2$ group or an ═O;
(iv) S$^1$ is a sugar moiety of formula:

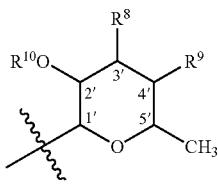

wherein
R[8] and R[9] are both hydrogen or together form a bond, or R[9] is hydrogen and R[8] is —N(CH$_3$)R[y], wherein R[y] is R[p], R[z] or —C(O)R[z] wherein R[z] is hydrogen or alkyl or alkenyl or alkynyl or cycloalkyl or aryl or heteroaryl or alkyl substituted with C$_2$–C$_7$-alkyl, C$_2$–C$_7$-alkenyl, C$_2$–C$_7$-alkynyl, aryl or heteroaryl R[10] is hydrogen or R[p];

(v) S[2] is a sugar moiety of formula:

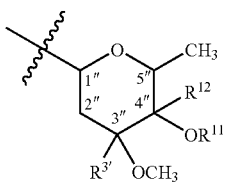

wherein:
R[3] is hydrogen or methyl;
R[11] is hydrogen, R[p] or O—R[11] is a group that with R[12] and with C/4" carbon atom forms a >C=O or epoxy group;
R[12] is hydrogen or a group that with O—R[11] group and with C/4" carbon atom forms a >C=O or epoxy group;

(vi) R[2] is hydrogen, hydroxy, OR[p] or alkoxy
(vii) A is hydrogen or methyl;
(viii) B is methyl or epoxy;
(ix) E is hydrogen or halogen;
(x) R[3] is hydroxy, OR[p], alkoxy or R[3] is a group that with R[5] and with C/11 and C/12 carbon atoms forms a cyclic carbonate or carbamate; or if W or Z is >N—R$_N$ R[3] is a group that with W or Z forms a cyclic carbamate;
(xi) R[4] is C$_1$–C$_4$ alkyl;
(xii) R[5] is hydrogen, hydroxy, OR[p], C$_1$–C$_4$-alkoxy, or a group that with R[3] and with C/11 and C/12 carbon atoms forms a cyclic carbonate or carbamate;
(xiii) R[6] is hydrogen or C$_1$–C$_4$-alkyl; and
R[p] is hydroxyl or amino protective group;
wherein M has a linkage site through which it is linked to V via linking group L; provided that the linkage site is at one or more of the following:
a) any reactive hydroxy, nitrogen, or epoxy group located on S[1], S[2], or an aglycone oxygen if S[1] or/and S[2] is cleaved off wherein if V is an antineoplastic subunit or an antiviral subunit, the linkage site is not on S[1];
b) a reactive >N—R$_N$ or —NR$_r$R$_s$ or =O group located on Z or W wherein if V is an antiviral subunit, Z or W is >C=O or >N—R$_N$;
c) a reactive hydroxy group located at any one of R[1], R[2], R[3], and R[5];
d)
wherein L is group of Formula IV:

X[1]—(CH$_2$)$_m$—Q—(CH$_2$)$_n$—X[2]      IV wherein
X[1] is selected from: —CH$_2$—, —C(O)—, OC(O)—, N—O—, —OC(O)NH— or —C(O)NH—;
X[2] is —NH— or —NHC(O)—, —OC(O)—, —C(O)—, —O or —CH$_2$—;
Q is —NH— or —CH$_2$—, or absent;
wherein each —CH$_2$— or NH— group may be optionally substituted by C$_1$–C$_7$-alkyl, C$_2$–C$_7$-alkenyl, C$_2$–C$_7$-alkynyl, C(O)R[x], C(O)OR[x], C(O)NHR[x] wherein R[x] may be C$_1$–C$_7$-alkyl, aryl or heteroaryl;
the symbols m and n independently are a whole number from 0 to 4, with the proviso that if Q is NH, n cannot be 0,
with proviso that if L is group of Formula IV, V is an antineoplastic subunit or an antiviral subunit; or
L represents a polypeptide of between about two and about 50 amino acids joined together;
V is selected from the group consisting of
(i) anti-inflammatory steroid subunit which represents a member of the group of Formula X:

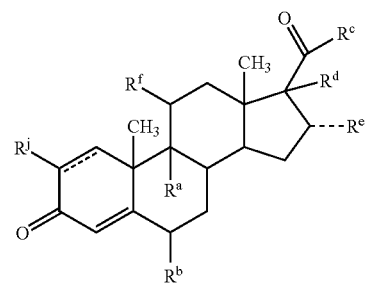

wherein
R[a] and R[b] independently represents, hydrogen or halogen;
R[c] is hydroxy, alkoxy, alkyl, thiocarbamoyl, carbamoyl or a valence-bond;
R[d] and R[e] independently represents: hydrogen, hydroxy, methyl or C$_1$–C$_4$-alkoxy or each are a group that forms a 1,3-dioxolane ring with the other or a valence bond;
R[f] is hydrogen, hydroxy, chloro, or forming a keto group with the carbon atom it is attached to;
R[j] is hydrogen or halogen;
(ii) a non-steroidal anti-inflammatory subunit derived from the NSAID selected from the group consisting of: aceclofenac, acemetacin, acetaminophen, acetaminosalol, acetyl-salicylic acid, acetyl-salicylic-2-amino-4-picoline-acid, 5-aminoacetylsalicylic acid, alclofenac, aminoprofen, amfenac, ampyrone, ampiroxicam, anileridine, bendazac, benoxaprofen, bermoprofen, α-bisabolol, bromfenac, 5-bromosalicylic acid acetate, bromosaligenin, bucloxic acid, butibufen, carprofen, celexocib, chromoglycate, cinmetacin, clindanac, clopirac, sodium diclofenac, diflunisal, ditazol, droxicam, enfenamic acid, etodolac, etofenamate, felbinac, fenbufen, fenclozic acid, fendosal, fenoprofen, fentiazac, fepradinol, flufenac, flufenamic acid, flunixin, flunoxaprofen, flurbiprofen, glutametacin, glycol salicylate, ibufenac, ibuprofen, ibuproxam, indomethacin, indoprofen, isofezolac, isoxepac, isoxicam, ketoprofen, ketorolac, lornoxicam, loxoprofen, meclofenamic acid, mefenamic acid, meloxicam, mesalamine, metiazinic acid, mofezolac, montelukast, nabumetone, naproxen, niflumic acid, nimesulide, olsalazine, oxaceprol, oxaprozin, oxyphenbutazone, paracetamol, parsalmide, perisoxal, phenyl-acethyl-salicylate, phenylbutazone, phenylsalicylate, pyrazolac, piroxicam, pirprofen, pranoprofen, protizinic acid, reserveratol, salacetamide, salicylamide, salicylamide-O-acetyl acid, salicylsulphuric acid, salicin, salicylamide, salsalate, sulindac, suprofen, suxibutazone, tamoxifen, tenoxicam, tiaprofenic acid, tiaramide, ticlopridine, tinoridine, tolfenamic acid, tolmetin, tropesin, xenbucin, ximoprofen, zaltoprofen, zomepirac, tomoxiprol, zafirlukast and cyclosporine;

(iii) an antineoplastic subunit derived from the antineoplastic compounds selected from a group consisting of bicaluatnide, camptothecin, estramustine phosphate, flutamide, mechlorethamine, thiotepa, ifosfamide, hydroxyurea, bleomycin, paclitaxel, lomustine, irinotecan, methotrexate, vinorelbine, anastrazole, floxuridine, melphalan, vincristine, vinblastine, mitomycin, nandrolone, goserelin, leuprolide, triptorelin, aminogluthetemide, mitotane, cisplatine, chlorambucil, pentostatin, cladribine, busulfan, etoposide, mitoxantrone, idarubicin, cyclophosphamide, mercaptopurine, thioguanine, cytarbine, cyclophosphamide, doxorubicin, daunoribicin, teniposide tamoxifen, taxotere and topotecan; and (iv) an antiviral subunit derived from the anti-viral compounds selected from a group consisting of aciclovir, famciclovir, ganciclovir, cidofovir, lamivudine, ritonavir, indinavir, nevirapine, zidovudine, didanosine, stavudine, abacavir, amprenavir, ribavirin and adamantane; and or a pharmaceutically acceptable salt or solvate thereof or an individual diastereoisomer thereof which comprises the steps of:

a) for a compound of Formula I, where $X^2$ is —NHC(O)—, by reacting a compound of Formula VI:

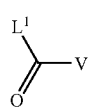

VI wherein $L^1$ represents a leaving group, and a free amino group of a macrolide represented by Formula VIIa:

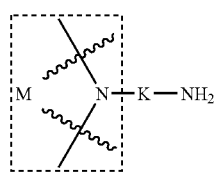

VIIa b) for a compound of Formula I, where $X^2$ is —OC(O)—, by reacting a compound of Formula VI and the free hydroxyl group of a macrolide represented by Formula VIIb:

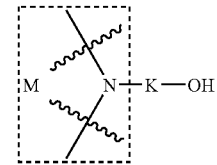

VIIb c) for a compound of Formula I, wherein $X^1$ is —OC(O)—, Q is —NH— and $X^2$ is —NHC(O)—, by reacting a macrolide represented by Formula VIIc:

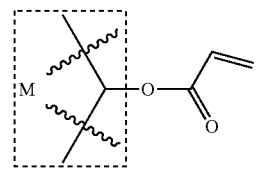

VIIc and a free amino group of the compound represented by Formula VIb:

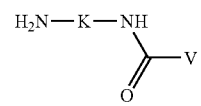

d) for a compound of Formula I, where $X^1$ is —OC(O)NH— and $X^2$ is —NHC(O)—, by reacting a macrolide represented by Formula VIId and free amino group of of the compound represented by Formula VIb:

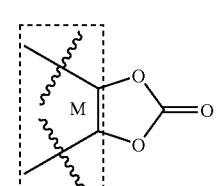

VIId

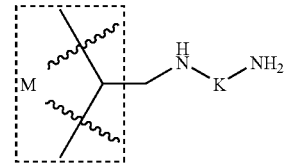

VIIe e) for a compound of Formula I, where $X^1$ is —CH$_2$—, Q is —NH— and $X^2$ is —NHC(O)—, by reacting a macrolide represented by Formula VIIe and a compound of Formula VI:

f) for any L compound of Formula I by reacting a macrolide represented by Formula VIIf or by Formula VIIg or by Formula VIIh having a leaving group $L^2$ VIIf

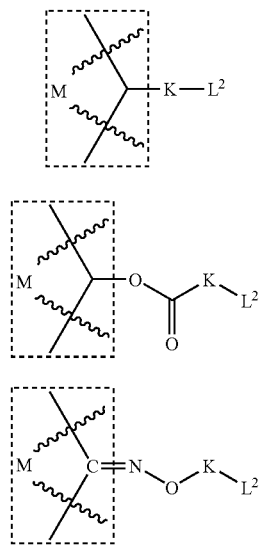

VIIg

VIIh with a free carboxylic acid of a nonsteroid anti inflammatory subunit represented by the Formula VIc:

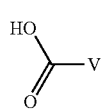

VIc

31. A pharmaceutical composition comprising a compound or a pharmaceutically acceptable salt or solvate of said compound according to claim 1 as well as a pharmaceutically acceptable diluent or carrier.

32. A method for the treatment of inflammatory diseases, disorders and conditions characterized by or associated with an undesirable inflammatory immune response, comprising administering to a subject afflicted with one of said disorders or conditions a compound according to claim 1 wherein;

V is chosen from the group consisting of (i) an anti-inflammatory steroid subunit of Formula X:

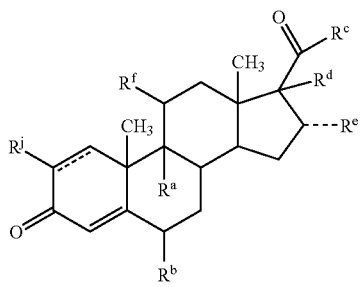

X wherein $R^a$ and $R^b$ independently represents, hydrogen or halogen;
$R^c$ is hydroxy, alkoxy, alkyl, thiocarbamoyl, carbamoyl or a valence-bond;

$R^d$ and $R^e$ independently represents: hydrogen, hydroxy, methyl or $C_1$–$C_4$-alkoxy or each are a group that forms a 1,3-dioxolane ring with the other or a valence bond;
$R^f$ is hydrogen, hydroxy, chloro, or forming a keto group with the carbon atom it is attached to;
$R^j$ is hydrogen or halogen;

and (ii) an NSAIDs selected from: aceclofenac, acemetacin, acetaminophen, acetaminosalol, acetyl-salicylic acid, acetyl-salicylic-2-amino-4-picoline-acid, 5-aminoacetylsalicylic acid, alclofenac, aminoprofen, amfenac, ampyrone, ampiroxicam, anileridine, bendazac, benoxaprofen, bermoprofen, α-bisabolol, bromfenac, 5-bromosalicylic acid acetate, bromosaligenin, bucloxic acid, butibufen, carprofen, celexocib, chromoglycate, cinmetacin, clindanac, clopirac, sodium diclofenac, diflunisal, ditazol, droxicam, enfenamic acid, etodolac, etofenamate, felbinac, fenbufen, fenclozic acid, fendosal, fenoprofen, fentiazac, fepradinol, flufenac, flufenamic acid, flunixin, flunoxaprofen, flurbiprofen, glutametacin, glycol salicylate, ibufenac, ibuprofen, ibuproxam, indomethacin, indoprofen, isofezolac, isoxepac, isoxicam, ketoprofen, ketorolac, lornoxicam, loxoprofen, meclofenamic acid, mefenamic acid, meloxicam, mesalamine, metiazinic acid, mofezolac, montelukast, nabumetone, naproxen, niflumic acid, nimesulide, olsalazine, oxaceprol, oxaprozin, oxyphenbutazone, paracetamol, parsalmide, perisoxal, phenyl-acetyl-salicylate, phenylbutazone, phenylsalicylate, pyrazolac, piroxicam, pirprofen, pranoprofen, protizinic acid, reserveratol, salacetamide, salicylamide, salicylamide-O-acetyl acid, salicylsulphuric acid, salicin, salicylamide, salsalate, sulindac, suprofen, suxibutazone, tamoxifen, tenoxicam, tiaprofenic acid, tiaramide, ticlopridine, tinoridine, tolfenamic acid, tolmetin, tropesin, xenbucin, ximoprofen, zaltoprofen, zomepirac, tomoxiprol, zafirlukast and cyclosporine.

33. A method of treating an inflammatory condition or an immune or anaphylactic disorder associated with infiltration of leukocytes into inflamed tissue in a subject in need thereof which comprises administering to said subject a therapeutically effective amount of a compound according to claim 1 wherein;

V is chosen from the group consisting of (i) an anti-inflammatory steroid subunit of Formula X:

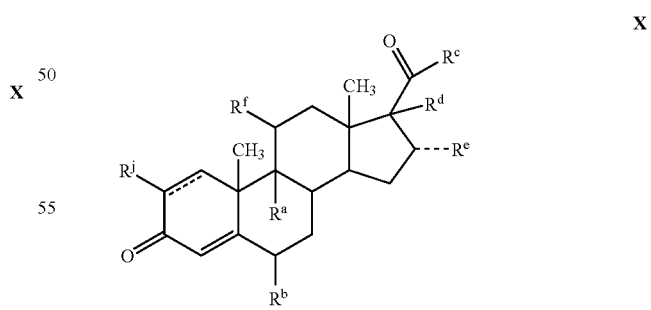

X wherein
$R^a$ and $R^b$ independently represents, hydrogen or halogen;
$R^c$ is hydroxy, alkoxy, alkyl, thiocarbamoyl, carbamoyl or a valence-bond;
$R^d$ and $R^e$ independently represents: hydrogen, hydroxy, methyl or $C_1$–$C_4$-alkoxy or each are a group that forms a 1,3-dioxolane ring with the other or a valence bond;

R$^f$ is hydrogen, hydroxy, chloro, or forming a keto group with the carbon atom it is attached to;

R$^j$ is hydrogen or halogen;

and (ii) a nonsteroidal anti-inflammatory subunit derived from an NSAID selected from the group consisting of: aceclofenac, acemetacin, acetaminophen, acetaminosalol, acetyl-salicylic acid, acetyl-salicylic-2-amino-4-picoline-acid, 5-aminoacetylsalicylic acid, alclofenac, aminoprofen, amfenac, ampyrone, ampiroxicam, anileridine, bendazac, benoxaprofen, bermoprofen, α-bisabolol, bromfenac, 5-bromosalicylic acid acetate, bromosaligenin, bucloxic acid, butibufen, carprofen, celexocib, chromoglycate, cinmetacin, clindanac, clopirac, sodium diclofenac, diflunisal, ditazol, droxicam, enfenamic acid, etodolac, etofenamate, felbinac, fenbufen, fenclozic acid, fendosal, fenoprofen, fentiazac, fepradinol, flufenac, flufenamic acid, flunixin, flunoxaprofen, flurbiprofen, glutametacin, glycol salicylate, ibufenac, ibuprofen, ibuproxam, indomethacin, indoprofen, isofezolac, isoxepac, isoxicam, ketoprofen, ketorolac, lornoxicam, loxoprofen, meclofenamic acid, mefenamic acid, meloxicam, mesalamine, metiazinic acid, mofezolac, montelukast, nabumetone, naproxen, niflumic acid, nimesulide, olsalazine, oxaceprol, oxaprozin, oxyphenbutazone, paracetamol, parsalmide, perisoxal, phenyl-acetyl-salicylate, phenylbutazone, phenylsalicylate, pyrazolac, piroxicam, pirprofen, pranoprofen, protizinic acid, reserveratol, salacetamide, salicylamide, salicylamide-O-acetyl acid, salicylsulphuric acid, salicin, salicylamide, salsalate, sulindac, suprofen, suxibutazone, tamoxifen, tenoxicam, tiaprofenic acid, tiaramide, ticlopridine, tinoridine, tolfenamic acid, tolmetin, tropesin, xenbucin, ximoprofen, zaltoprofen, zomepirac, tomoxiprol, zafirlukast and cyclosporine.

34. Method according to claim 33, wherein said condition or disorder is selected from the group consisting of asthma, adult respiratory distress syndrome, bronchitis, and cystic fibrosis.

35. A method according to claim 33, wherein said inflammatory condition or disorder is selected from the group consisting of inflammatory conditions or immune disorders of the lungs, joints, eyes, bowel, skin, and heart.

36. A method according to claim 33, wherein said inflammatory condition or disorder is selected from the group consisting of asthma, adult respiratory distress syndrome, bronchitis, cystic fibrosis, rheumatoid arthritis, rheumatoid spondylitis, osteoarthritis, gouty arthritis, uveitis, conjunctivitis, inflammatory bowel conditions, Crohn's disease, ulcerative colitis, distal proctitis, psoriasis, eczema, dermatitis, coronary infarct damage, chronic inflammation, endotoxin shock, and smooth muscle proliferation disorders.

37. A method for abating inflamation in an affected organ or tissue comprising delivering to said organ or tissue a therapeutically effective amount of a compound according to claim 1 wherein V is selected from the group consisting of (i) an anti-inflammatory steroid subunit of Formula X:

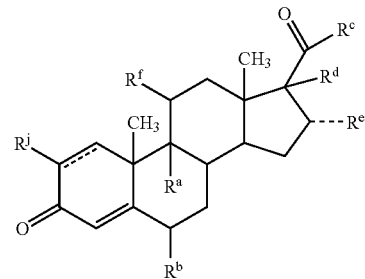

wherein

R$^a$ and R$^b$ independently represents, hydrogen or halogen;

R$^c$ is hydroxy, alkoxy, alkyl, thiocarbamoyl, carbamoyl or a valence-bond;

R$^d$ and R$^e$ independently represents: hydrogen, hydroxy, methyl C$_1$–C$_4$-alkoxy or each are a group that forms a 1,3-dioxolane ring with the other or a valence bond;

R$^f$ is hydrogen, hydroxy, chloro, or forming a keto group with the carbon atom it is attached to;

R$^1$ is hydrogen or halogen; and (ii) a non-steroidal anti-inflammatory subunit derived from the NSAID selected from the group consisting of: aceclofenac, acemetacin, acetaminophen, acetaminosalol, acetyl-salicylic acid, acetyl-salicylic-2-amino-4-picoline-acid, 5-aminoacetylsalicylic acid, alclofenac, aminoprofen, amfenac, ampyrone, ampiroxicam, anileridine, bendazac, benoxaprofen, bermoprofen, α-bisabolol, bromfenac, 5-bromosalicylic acid acetate, bromosaligenin, bucloxic acid, butibufen, carprofen, celexocib, chromoglycate, cinmetacin, clindanac, clopirac, sodium diclofenac, diflunisal, ditazol, droxicam, enfenamic acid, etodolac, etofenamate, felbinac, fenbufen, fenclozic acid, fendosal, fenoprofen, fentiazac, fepradinol, flufenac, flufenamic acid, flunixin, flunoxaprofen, flurbiprofen, glutametacin, glycol salicylate, ibufenac, ibuprofen, ibuproxam, indomethacin, indoprofen, isofezolac, isoxepac, isoxicam, ketoprofen, ketorolac, lornoxicam, loxoprofen, meclofenamic acid, mefenamic acid, meloxicam, mesalamine, metiazinic acid, mofezolac, montelukast, nabumetone, naproxen, niflumic acid, nimesulide, olsalazine, oxaceprol, oxaprozin, oxyphenbutazone, paracetamol, parsalmide, perisoxal, phenyl-acetyl-salicylate, phenylbutazone, phenylsalicylate, pyrazolac, piroxicam, pirprofen, pranoprofen, protizinic acid, reserveratol, salacetamide, salicylamide, salicylamide-O-acetyl acid, salicylsulphuric acid, salicin, salicylamide, salsalate, sulindac, suprofen, suxibutazone, tamoxifen, tenoxicam, tiaprofenic acid, tiaramide, ticlopridine, tinoridine, tolfenamic acid, tolmetin, tropesin, xenbucin, ximoprofen, zaltoprofen, zomepirac, tomoxiprol, zafirlukast and cyclosporine.

38. A method for the treatment of viral diseases, disorders and conditions, comprising administering to a subject afflicted with one of said diseases or disorders an effective amount of a compound according to claim 1 wherein V is an antiviral subunit derived from the anti-viral compounds selected from the group consisting of aciclovir, famciclovir, ganciclovir, cidofovir, lamivudine, ritonavir, indinavir, nevirapine, zidovudine, didanosine, stavudine, abacavir, amprenavir, ribavirin and adamantane.

39. The method according to claim 38 wherein said viral disease is HIV.

40. A method for abating a sign or symptom or markers of a viral infection comprising administering to a subject presenting with said sign or symptom or marker a therapeutically effective amount of a compound according to claim 1, wherein V is an antiviral subunit derived from the anti-viral compounds selected from the group consisting of aciclovir, famciclovir, ganciclovir, cidofovir, lamivudine, ritonavir, indinavir, nevirapine, zidovudine, didanosine, stavudine, abacavir, amprenavir, ribavirin and adamantane 41. A method for treating a symptom or sign or marker of viral infection, comprising administering to a subject presenting with said sign or symptom or marker a therapeutically effective amount of a compound according to claim 1, wherein V is an antineoplastic subunit derived from the antineoplastic compounds selected from the group consisting of bicaluatnide, camptothecin, estramustine phosphate, flutamide, mechlorethamine, thiotepa, ifosfamide, hydroxyurea, bleomycin, paclitaxel, lomustine, irinotecan, methotrexate, vinorelbine, anastrazole, floxuridine, melphalan, vincristine, vinblastine, mitomycin, nandrolone, goserelin, leuprolide, triptorelin, aminogluthetemide, mitotane, cisplatine, chlorambucil, pentostatin, cladribine, busulfan, etoposide, mitoxantrone, idarubicin, cyclophosphamide, mercaptopurine, thioguanine, cytarbine, cyclophosphamide, doxorubicin, daunoribicin, teniposide tamoxifen, taxotere and topotecan.

42. The method according to claim 41 wherein said symptom or sign is selected from the group consisting of viral load, viral replication, viral activity, viremia, viral-specific antigens, viral RNA, viral DNA, reverse transcriptase activity, antiviral cytoxic cell activity in the subject, and T-cell or CD4+ cell count of the subject.

43. A method of treating a symptom or sign or marker of neoplasia comprising administering to a subject presenting with said symptom or sign a therapeutically effective amount of a compound according to claim 1, wherein V is an antineoplastic subunit derived from the antineoplastic compounds selected from the group consisting of bicaluatnide, camptothecin, estramustine phosphate, flutamide, mechlorethamine, thiotepa, ifosfamide, hydroxyurea, bleomycin, paclitaxel, lomustine, irinotecan, methotrexate, vinorelbine, anastrazole, floxuridine, melphalan, vincristine, vinblastine, mitomycin, nandrolone, goserelin, leuprolide, triptorelin, aminogluthetemide, mitotane, cisplatine, chlorambucil, pentostatin, cladribine, busulfan, etoposide, mitoxantrone, idarubicin, cyclophosphamide, mercaptopurine, thioguanine, cytarbine, cyclophosphamide, doxorubicin, daunoribicin, teniposide tamoxifen, taxotere and topotecan.

44. The method according to claim 43 wherein said symptom or sign of neoplasia is selected from the group consisting of tumor burden, tumor size, afflicted organ weight, tumor recurrence, survival time, length or extent of subject remission, growth of cancer cells, cancer cell survival, apoptosis index, metatasis extent or metastasis rate, a biological marker associated with a particular type of neoplasia, proliferation markers, activation of relevant oncogenes dysregulation of tumor associated receptor function, tumor-specific antigens and tumor associated angiogensis.

45. A method of treating neoplasia comprising administering to a subject afflicted with neoplasia a therapeutically effective amount of a compound according to claim 1, wherein V is an antineoplastic subunit derived from the antineoplastic compounds selected from the group consisting of bicaluatnide, camptothecin, estramustine phosphate, flutamide, mechlorethamine, thiotepa, ifosfamide, hydroxyurea, bleomycin, paclitaxel, lomustine, irinotecan, methotrexate, vinorelbine, anastrazole, floxuridine, melphalan, vincristine, vinblastine, mitomycin, nandrolone, goserelin, leuprolide, triptorelin, aminogluthetemide, mitotane, cisplatine, chlorambucil, pentostatin, cladribine, busulfan, etoposide, mitoxantrone, idarubicin, cyclophosphamide, mercaptopurine, thioguanine, cytarbine, cyclophosphamide, doxorubicin, daunoribicin, teniposide tamoxifen, taxotere and topotecan.

46. The compound according to claim 2 wherein said polypeptide is chosen from the group consisting of:
Gly-Phe-Leu, Gly-Gly-Phe, Gly-Phe-Phe, Gly-Phe-Gly, Gly-Leu-Gly, Gly-Val-Ala, Gly-Phe-Ala, Gly-Leu-Phe, Gly-Leu-Ala, Ala-Val-Ala, Gly-Gly-Phe-Leu, Gly-Phe-Leu-Gly, Gly-Phe-Ala-Leu, Ala-Leu-Ala-Leu, Gly-Phe-Phe-Leu, Gly-Leu-Leu-Gly, Gly-Phe-Tyr-Ala, Gly-Phe-Gly-Phe, Ala-Gly-Val-Phe, and Gly-Phe-Phe-Gly.

47. The method of claim 32, wherein the inflammatory disease, disorder or condition is induced by or associated with an excessive secretion of TNF-α and IL-1.

48. A method of treating an inflammatory condition or an immune or anaphylactic disorder associated with infiltration of leukocytes into inflamed tissue in a subject in need thereof which comprises administering to said subject a therapeutically effective amount of a compound according to claim 2 wherein;
V is chosen from the group consisting of (i) an anti-inflammatory steroid subunit of Formula X:

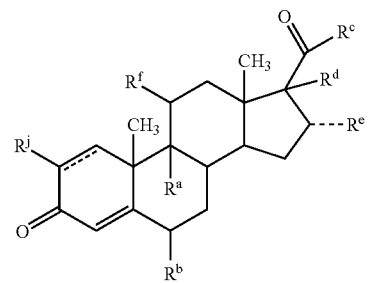

X wherein
$R^a$ and $R^b$ independently represents, hydrogen or halogen;
$R^c$ is hydroxy, alkoxy, alkyl, thiocarbamoyl, carbamoyl or a valence-bond;
$R^d$ and $R^e$ independently represents: hydrogen, hydroxy, methyl or $C_1$–$C_4$-alkoxy or each are a group that forms a 1,3-dioxolane ring with the other or a valence bond;
$R^f$ is hydrogen, hydroxy, chloro, or forming a keto group with the carbon atom it is attached to;
$R^j$ is hydrogen or halogen;
and (ii) a nonsteroidal anti-inflammatory subunit derived from an NSAID selected from the group consisting of: aceclofenac, acemetacin, acetaminophen, acetaminosalol, acetyl-salicylic acid, acetyl-salicylic-2-amino-4-picoline-acid, 5-aminoacetylsalicylic acid, alclofenac, aminoprofen, amfenac, ampyrone, ampiroxicam, anileridine, bendazac, benoxaprofen, bermoprofen, α-bisabolol, bromfenac, 5-bromosalicylic acid acetate, bromosaligenin, bucloxic acid, butibufen, carprofen, celexocib, chromoglycate, cinmetacin, clindanac, clopirac, sodium diclofenac, diflunisal, ditazol, droxicam, enfenamic acid, etodolac, etofenamate, felbinac, fenbufen, fenclozic acid, fendosal, fenoprofen, fentiazac, fepradinol, flufenac, flufenamic acid, flunixin, flunoxaprofen, flurbiprofen, glutametacin, glycol salicylate, ibufenac, ibuprofen, ibuproxam, indomethacin, indoprofen, isofezolac, isoxepac, isoxicam, ketoprofen, ketorolac, lornoxicam, loxoprofen, meclofenamic acid, mefenamic acid, meloxicam, mesalamine, metiazinic acid, mofezolac, montelukast, nabumetone, naproxen, niflumic acid, nimesulide, olsalazine, oxaceprol, oxaprozin, oxyphenbutazone, paracetamol, parsalmide, perisoxal, phenyl-acethyl-salicylate, phenylbutazone, phenylsalicylate, pyrazolac, piroxicam, pirprofen, pranoprofen, protizinic acid, reserveratol, salacetamide, salicylamide, salicylamide-O-acetyl acid, salicylsulphuric acid, salicin, salicylamide, salsalate, sulindac, suprofen, suxibutazone, tamoxifen, tenoxicam, tiaprofenic acid, tiaramide, ticlopridine, tinoridine, tolfenamic acid, tolmetin, tropesin, xenbucin, ximoprofen, zaltoprofen, zomepirac, tomoxiprol, zafirlukast and cyclosponne.

49. Method according to claim 48, wherein said condition or disorder is selected from the group consisting of asthma, adult respiratory distress syndrome, bronchitis, and cystic fibrosis.

50. A method according to claim 48, wherein said inflammatory condition or disorder is selected from the group consisting of inflammatory conditions or immune disorders of the lungs, joints, eyes, bowel, skin, and heart.

51. A method according to claim 48, wherein said inflammatory condition or disorder is selected from the group consisting of asthma, adult respiratory distress syndrome, bronchitis, cystic fibrosis, rheumatoid arthritis, rheumatoid spondylitis, osteoarthritis, gouty arthritis, uveitis, conjunctivitis, inflammatory bowel conditions, Crohn's disease, ulcerative colitis, distal proctitis, psoriasis, eczema, dermatitis, coronary infarct damage, chronic inflammation, endotoxin shock, and smooth muscle proliferation disorders.

52. A method for abating inflamation in an affected organ or tissue comprising delivering to said organ or tissue a therapeutically effective amount of a compound according to claim 2 wherein V is selected from the group consisting of (i) an anti-inflammatory steroid subunit of Formula X:

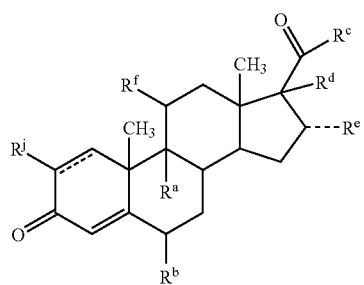

X wherein
$R^a$ and $R^b$ independently represents, hydrogen or halogen;
$R^c$ is hydroxy, alkoxy, alkyl, thiocarbamoyl, carbamoyl or a valence-bond;
$R^d$ and $R^e$ independently represents: hydrogen, hydroxy, methyl or $C_1$–$C_4$-alkoxy or each are a group that forms a 1,3-dioxolane ring with the other or a valence bond;

$R^f$ is hydrogen, hydroxy, chloro, or forming a keto group with the carbon atom it is attached to;
$R^j$ is hydrogen or halogen;
and (ii) a non-steroidal anti-inflammatory subunit derived from the NSAID selected from the group consisting of: aceclofenac, acemetacin, acetaminophen, acetaminosalol, acetyl-salicylic acid, acetyl-salicylic-2-amino-4-picoline-acid, 5-aminoacetylsalicylic acid, alclofenac, aminoprofen, amfenac, ampyrone, ampiroxicam, anileridine, bendazac, benoxaprofen, bermoprofen, α-bisabolol, bromfenac, 5-bromosalicylic acid acetate, bromosaligenin, bucloxic acid, butibufen, carprofen, celexocib, chromoglycate, cinmetacin, clindanac, clopirac, sodium diclofenac, diflunisal, ditazol, droxicam, enfenamic acid, etodolac, etofenamate, felbinac, fenbufen, fenclozic acid, fendosal, fenoprofen, fentiazac, fepradinol, flufenac, flufenamic acid, flunixin, flunoxaprofen, flurbiprofen, glutametacin, glycol salicylate, ibufenac, ibuprofen, ibuproxam, indomethacin, indoprofen, isofezolac, isoxepac, isoxicam, ketoprofen, ketorolac, lornoxicam, loxoprofen, meclofenamic acid, mefenamic acid, meloxicam, mesalamine, metiazinic acid, mofezolac, montelukast, nabumetone, naproxen, niflumic acid, nimesulide, olsalazine, oxaceprol, oxaprozin, oxyphenbutazone, paracetamol, parsalmide, perisoxal, phenyl-acethyl-salicylate, phenylbutazone, phenylsalicylate, pyrazolac, piroxicam, pirprofen, pranoprofen, protizinic acid, reserveratol, salacetamide, salicylamide, salicylamide-O-acetyl acid, salicylsulphuric acid, salicin, salicylamide, salsalate, sulindac, suprofen, suxibutazone, tamoxifen, tenoxicam, tiaprofenic acid, tiaramide, ticlopridine, tinoridine, tolfenamic acid, tolmetin, tropesin, xenbucin, ximoprofen, zaltoprofen, zomepirac, tomoxiprol, zafirlukast and cyclosporine.

53. A method for the treatment of viral diseases, disorders and conditions, comprising administering to a subject afflicted with one of said diseases or disorders an effective amount of a compound according to claim 2 wherein V is an antiviral subunit derived from the anti-viral compounds selected from the group consisting of aciclovir, famciclovir, ganciclovir, cidofovir, lamivudine, ritonavir, indinavir, nevirapine, zidovudine, didanosine, stavudine, abacavir, amprenavir, ribavirin and adamantane.

54. The method according to claim 53 wherein said viral disease is HIV.

55. A method for abating a sign or symptom or markers of a viral infection comprising administering to a subject presenting with said sign or symptom or marker a therapeutically effective amount of a compound according to claim 2, wherein V is an antiviral subunit derived from the anti-viral compounds selected from the group consisting of aciclovir, famciclovir, ganciclovir, cidofovir, lamivudine, ritonavir, indinavir, nevirapine, zidovudine, didanosine, stavudine, abacavir, amprenavir, ribavirin and adamantane 56. A method for treating a symptom or sign or marker of viral infection, comprising administering to a subject presenting with said sign or symptom or marker a therapeutically effective amount of a compound according to claim 2, wherein V is an antineoplastic subunit derived from the antineoplastic compounds selected from the group consisting of bicaluatnide, camptothecin, estramustine phosphate, flutamide, mechlorethamine, thiotepa, ifosfamide, hydroxyurea, bleomycin, paclitaxel, lomustine, irinotecan, methotrexate, vinorelbine, anastrazole, floxuridine, melphalan, vincristine, vinblastine, mitomycin, nandrolone, goserelin, leuprolide, triptorelin, aminogluthetemide, mitotane, cisplatine, chlorambucil, pentostatin, cladribine, busulfan, etoposide, mitoxantrone, idarubicin, cyclophosphamide, mercaptopurine, thioguanine, cytarbine, cyclophosphamide, doxorubicin, daunoribicin, teniposide tamoxifen, taxotere and topotecan.

57. The method according to claim 56 wherein said symptom or sign is selected from the group consisting of viral load, viral replication, viral activity, viremia, viral-specific antigens, viral RNA, viral DNA, reverse transcriptase activity, antiviral cytoxic cell activity in the subject, and T-cell or CD4+ cell count of the subject.

58. A method of treating a symptom or sign or marker of neoplasia comprising administering to a subject presenting with said symptom or sign a therapeutically effective amount of a compound according to claim 2, wherein V is an antineoplastic subunit derived from the antineoplastic compounds selected from the group consisting of bicaluatnide, camptothecin, estramustine phosphate, flutamide, mechlorethamine, thiotepa, ifosfamide, hydroxyurea, bleomycin, paclitaxel, lomustine, irinotecan, methotrexate, vinorelbine, anastrazole, floxuridine, melphalan, vincristine, vinblastine, mitomycin, nandrolone, goserelin, leuprolide, triptorelin, aminogluthetemide, mitotane, cisplatine, chlorambucil, pentostatin, cladribine, busulfan, etoposide, mitoxantrone, idarubicin, cyclophosphamide, mercaptopurine, thioguanine, cytarbine, cyclophosphamide, doxorubicin, daunoribicin, teniposide tamoxifen, taxotere and topotecan.

59. The method according to claim 58 wherein said symptom or sign of neoplasia is selected from the group consisting of tumor burden, tumor size, afflicted organ weight, tumor recurrence, survival time, length or extent of subject remission, growth of cancer cells, cancer cell survival, apoptosis index, metatasis extent or metastasis rate, a biological marker associated with a particular type of neoplasia, proliferation markers, activation of relevant oncogenes dysregulation of tumor associated receptor function, tumor-specific antigens and tumor associated angiogensis.

60. A method of treating neoplasia comprising administering to a subject afflicted with neoplasia a therapeutically effective amount of a compound according to claim 2, wherein V is an antineoplastic subunit derived from the antineoplastic compounds selected from the group consisting of bicaluatnide, camptothecin, estramustine phosphate, flutamide, mechlorethamine, thiotepa, ifosfamide, hydroxyurea, bleomycin, paclitaxel, lomustine, irinotecan, methotrexate, vinorelbine, anastrazole, floxuridine, melphalan, vincristine, vinblastine, mitomycin, nandrolone, goserelin, leuprolide, triptorelin, aminogluthetemide, mitotane, cisplatine, chlorambucil, pentostatin, cladribine, busulfan, etoposide, mitoxantrone, idarubicin, cyclophosphamide, mercaptopurine, thioguanine, cytarbine, cyclophosphamide, doxorubicin, daunoribicin, teniposide tamoxifen, taxotere and topotecan.

61. The compound of claim 1, wherein Z is >N—$R_N$ and M is linded to L at Z.

62. The compound of claim 1 wherein L is a peptide.

63. A compound of the formula I:

wherein

M represents a group of Formula II:

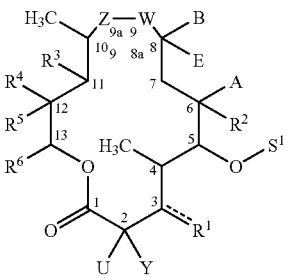

wherein:
(i) Z and W independently are: >C=O, >CH$_2$, >CH—NR$_t$R$_s$, >N—R$_N$ or >C=N—R$_M$ or a bond wherein:
R$_t$ and R$_s$ independently are hydrogen or alkyl;
R$_M$ is hydroxy, alkoxy, substituted alkoxy or OR$^p$;
R$_N$ is hydrogen, R$^p$, alkyl, alkenyl, alkynyl, alkoxy, alkoxyalkyl, or —C(X)—NR$_t$R$_s$; wherein X is =O or =S;
provided that Z and W cannot both simultaneously be, >C=O, >CH$_2$, >CH—NR$_t$R$_s$, >N—R$_N$ or >C=N—R$_M$ or a bond,
(ii) U and Y independently are hydrogen, halogen, alkyl, or hydroxyalkyl;
(iii) R$^1$ is hydroxy, OR$^p$, —O—S$^2$ group or an =O;
(iv) S$^1$ is a sugar moiety of formula:

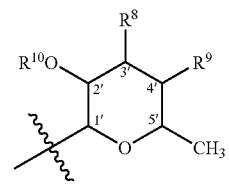

wherein
R$^8$ and R$^9$ are both hydrogen or together form a bond, or R$^9$ is hydrogen and R$^8$ is —N(CH$_3$)R$^y$, wherein R$^y$ is R$^p$, R$^z$ or —C(O)R$^z$ wherein R$^z$ is hydrogen or alkyl or alkenyl or alkynyl or cycloalkyl or aryl or heteroaryl or alkyl substituted with C$_2$–C$_7$-alkyl, C$_2$–C$_7$-alkenyl, C$_2$–C$_7$-alkynyl, aryl or heteroaryl
R$^{10}$ is hydrogen or R$^p$;
(v) S$^2$ is a sugar moiety of formula:

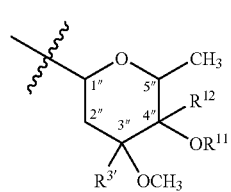

wherein:
R$^3$ is hydrogen or methyl;
R$^{11}$ is hydrogen, R$^p$ or O—R$^{11}$ is a group that with R$^{12}$ and with C/4" carbon atom forms a >C=O or epoxy group;
R$^{12}$ is hydrogen or a group that with O—R$^{11}$ group and with C/4" carbon atom forms a >C=O or epoxy group;

(vi) $R^2$ is hydrogen, hydroxy, $OR^p$ or alkoxy
(vii) A is hydrogen or methyl;
(viii) B is methyl or epoxy;
(ix) E is hydrogen or halogen;
(x) $R^3$ is hydroxy, $OR^p$, alkoxy or $R^3$ is a group that with $R^5$ and with C/11 and C/12 carbon atoms forms a cyclic carbonate or carbamate; or if W or Z is >N—$R_N$ $R^3$ is a group that with W or Z forms a cyclic carbamate;
(xi) $R^4$ is $C_1$–$C_4$ alkyl;
(xii) $R^5$ is hydrogen, hydroxy, $OR^p$, $C_1$–$C_4$-alkoxy, or a group that with $R^3$ and with C/11 and C/12 carbon atoms forms a cyclic carbonate or carbamate;
(xiii) $R^6$ is hydrogen or $C_1$–$C_4$-alkyl; and
$R^p$ is hydroxyl or amino protective group;
wherein M has a linkage site through which it is linked to V via linking group L; provided that the linkage site is at one or more of the following:
  a) any reactive hydroxy, nitrogen, or epoxy group located on $S^1$, $S^2$, or an aglycone oxygen if $S^1$ or/and $S^2$ is cleaved off;
  b) a reactive >N—$R_N$ or —$NR_tR_s$ or =O group located on Z or W;
  c) a reactive hydroxy group located at any one of $R^1$, $R^2$, $R^3$, and $R^5$;
  d) any other group that can be first derivatized to a hydroxy or —$NR_tR_s$ group and
V is chosen from the group consisting of (i) an anti-inflammatory steroid subunit of the Formula X:

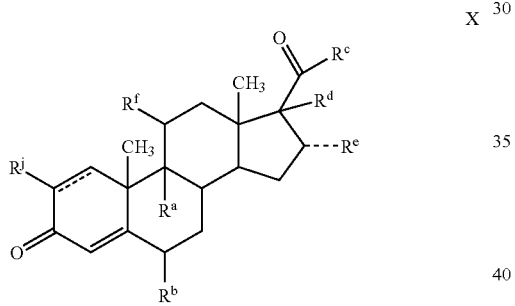

wherein
$R^a$ and $R^b$ independently represents, hydrogen or halogen;
$R^c$ is hydroxy, alkoxy, alkyl, thiocarbamoyl, carbamoyl or a valence-bond;
$R^d$ and $R^e$ independently represents: hydrogen, hydroxy, methyl or $C_1$–$C_4$-alkoxy or each are a group that forms a 1,3-dioxolane ring with the other or a valence bond;
$R^f$ is hydrogen, hydroxy, chloro, or forming a keto group with the carbon atom it is attached to;
$R^j$ is hydrogen or halogen;
(ii) a non-steroidal anti-inflammatory subunit derived from the NSAIDs selected from: aceclofenac, acemetacin, acetaminophen, acetaminosalol, acetyl-salicylic acid, acetyl-salicylic-2-amino-4-picoline-acid, 5-aminoacetylsalicylic acid, alclofenac, aminoprofen, amfenac, ampyrone, ampiroxicam, anileridine, bendazac, benoxaprofen, bermoprofen, α-bisabolol, bromfenac, 5-bromosalicylic acid acetate, bromosaligenin, bucloxic acid, butibufen, carprofen, celexocib, chromoglycate, cinmetacin, clindanac, clopirac, sodium diclofenac, diflunisal, ditazol, droxicam, enfenamic acid, etodolac, etofenamate, felbinac, fenbufen, fenclozic acid, fendosal, fenoprofen, fentiazac, fepradinol, flufenamic acid, flunixin, flunoxaprofen, flurbiprofen, glutametacin, glycol salicylate, ibufenac, ibuprofen, ibuproxam, indomethacin, indoprofen, isofezolac, isoxepac, isoxicam, ketoprofen, ketorolac, lornoxicam, loxoprofen, meclofenamic acid, mefenamic acid, meloxicam, mesalamine, metiazinic acid, mofezolac, montelukast, nabumetone, naproxen, niflumic acid, nimesulide, olsalazine, oxaceprol, oxaprozin, oxyphenbutazone, paracetamol, parsalmide, perisoxal, phenyl-acetyl-salicylate, phenylbutazone, phenylsalicylate, pyrazolac, piroxicam, pirprofen, pranoprofen, protizinic acid, reserveratol, salacetamide, salicylamide, salicylamide-O-acetyl acid, salicylsulphuric acid, salicin, salicylamide, salsalate, sulindac, suprofen, suxibutazone, tamoxifen, tenoxicam, tiaprofenic acid, tiaramide, ticlopridine, tinoridine, tolfenamic acid, tolmetin, tropesin, xenbucin, ximoprofen, zaltoprofen, zomepirac, tomoxiprol, zafirlukast and cyclosporine;
(iii) an antineoplastic subunit derived from the antineoplastic compounds selected from bicaluatnide, camptothecin, estramustine phosphate, flutamide, mechlorethamine, thiotepa, ifosfamide, hydroxyurea, bleomycin, paclitaxel, lomustine, irinotecan, methotrexate, vinorelbine, anastrazole, floxuridine, melphalan, vincristine, vinblastine, mitomycin, nandrolone, goserelin, leuprolide, triptorelin, aminogluthetemide, mitotane, cisplatine, chlorambucil, pentostatin, cladribine, busulfan, etoposide, mitoxantrone, idarubicin, cyclophosphamide, mercaptopurine, thioguanine, cytarbine, cyclophosphamide, doxorubicin, daunoribicin, teniposide tamoxifen, taxotere and topotecan; and
(iv) an antiviral subunit derived from the anti-viral compounds selecting from aciclovir, famciclovir, ganciclovir, cidofovir, lamivudine, ritonavir, indinavir, nevirapine, zidovudine, didanosine, stavudine, abacavir, amprenavir, ribavirin and adamantane;
L is a peptide linker molecule to which each of M and V are covalently linked; or a pharmaceutically acceptable salt or solvate thereof or an individual diastereoisomer thereof.
64. A compound of the formula I:

wherein
M represents a group of Formula II:

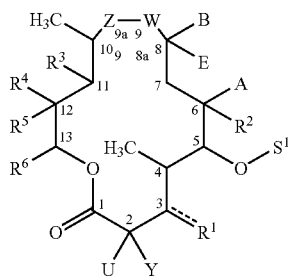

wherein
(i) Z and W independently are: >C=O, >$CH_2$, >CH—$NR_tR_s$, >N—$R_N$ or >C=N—$R_M$ or a bond wherein:
$R_t$ and $R_s$ independently are hydrogen or alkyl;
$R_M$ is hydroxy, alkoxy, or $OR^p$;
$R_N$ is hydrogen, $R^p$, alkyl, alkoxy, alkoxyalkyl, or —C(X)—$NR_tR_s$; wherein X is =O or =S;
provided that Z and W cannot both simultaneously be, >C=O, >$CH_2$, >CH—$NR_tR_s$, >N—$R_N$ or >C=N—$R_M$ or a bond, (ii) U and Y independently are hydrogen, halogen, alkyl, or hydroxyalkyl;
(iii) $R^1$ is hydroxy, $OR^p$, —O—$S^2$ group or an =O;
(iv) $S^1$ is a sugar moiety of formula:

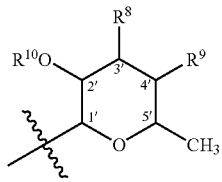

wherein
$R^8$ and $R^9$ are both hydrogen or together form a bond, or $R^9$ is hydrogen and $R^8$ is —N(CH$_3$)$R^y$, wherein $R^y$ is $R^p$, $R^z$ or —C(O)$R^z$ wherein $R^z$ is hydrogen or alkyl which may be substituted with $C_2$–$C_7$-alkyl, $C_2$–$C_7$-alkenyl, aryl or heteroaryl
$R^{10}$ is hydrogen or $R^p$;
(v) $S^2$ is a sugar moiety of formula:

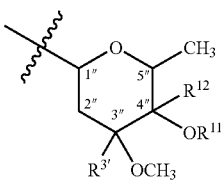

wherein:
$R^3$ is hydrogen or methyl;
$R^{11}$ is hydrogen,
$R^{12}$ is hydrogen;
(vi) $R^2$ is hydrogen, hydroxy, $OR^p$ or alkoxy
(vii) A is hydrogen or methyl;
(viii) B is methyl or epoxy;
(ix) E is hydrogen or halogen;
(x) $R^3$ is hydroxy, $OR^p$, alkoxy or $R^3$ is a group that with $R^5$ and with C/11 and C/12 carbon atoms forms a cyclic carbonate or carbamate; or if W or Z is >N—$R_N$ $R^3$ is a group that with W or Z forms a cyclic carbamate;
(xi) $R^4$ is $C_1$–$C_4$ alkyl;
(xii) $R^5$ is hydrogen, $OR^p$, $C_1$–$C_4$-alkoxy, or a group that with $R^3$ and with C/11 and C/12 carbon atoms forms a cyclic carbonate or carbamate;
(xiii) $R^6$ is hydrogen or $C_1$–$C_4$-alkyl; and
$R^p$ is hydroxyl or amino protective group;
wherein M has a linkage site through which it is linked to V via linking group L; provided that the linkage site is at one or more of the following:
a) any reactive hydroxy, nitrogen, or epoxy group located on $S^1$, $S^2$, or an aglycone oxygen if $S^1$ or/and $S^2$ is cleaved off;
b) a reactive >N—$R_N$ or —$NR_rR_s$ or =O group located on Z or W;
c) a reactive hydroxy group located at any one of $R^1$, $R^2$, $R^3$, and $R^5$;
d) any other group that can be first derivatized to a hydroxy or —$NR_rR_s$ group;
V is chosen from the group consisting of (i) an anti-inflammatory steroid subunit steroid selected from cortisol, cortisone, clobetasol, hydrocortisone, fludrocortisone, fludroxycortide, flumetasone, flunisolide, fluocinolone, fluocinonide, fluocortolone, fluorometholone, prednisone, prednisolone, 6-alpha-methyiprednisolone, triamcinolone, alciometasone, beclometasone, betamethasone, budesonide, dexamethasone, amcinonide, cortivazol, desonide, desoximethasone diflucortolone, difluprednate, fluclorolone and dichiorisone, fluperinidene, fluticasone, halcinonide, meprednisone, methyiprednisolone, paramethasone, prednazoline, prednylidene, tixocortol, triamincinolone, and acid derivatives thereof
(ii) a non-steroidal anti-inflammatory subunit derived from the NSAIDs selected from: aceclofenac, acemetacin, acetaminophen, acetaminosalol, acetyl-salicylic acid, acetyl-salicylic-2-amino-4-picoline-acid, 5-aminoacetylsalicylic acid, alclofenac, aminoprofen, amfenac, ampyrone, ampiroxicam, anileridine, bendazac, benoxaprofen, bermoprofen, α-bisabolol, bromfenac, 5-bromosalicylic acid acetate, bromosaligenin, bucloxic acid, butibufen, carprofen, celexocib, chromoglycate, cinmetacin, clindanac, clopirac, sodium diclofenac, diflunisal, ditazol, droxicam, enfenamic acid, etodolac, etofenamate, felbinac, fenbufen, fenclozic acid, fendosal, fenoprofen, fentiazac, fepradinol, flufenac, flufenamic acid, flunixin, flunoxaprofen, flurbiprofen, glutametacin, glycol salicylate, ibufenac, ibuprofen, ibuproxam, indomethacin, indoprofen, isofezolac, isoxepac, isoxicam, ketoprofen, ketorolac, lornoxicam, loxoprofen, meclofenamic acid, mefenamic acid, meloxicam, mesalamine, metiazinic acid, mofezolac, montelukast, nabumetone, naproxen, niflumic acid, nimesulide, olsalazine, oxaceprol, oxaprozin, oxyphenbutazone, paracetamol, parsalmide, perisoxal, phenyl-acethyl-salicylate, phenylbutazone, phenylsalicylate, pyrazolac, piroxicam, pirprofen, pranoprofen, protizinic acid, reserveratol, salacetamide, salicylamide, salicylamide-O-acetyl acid, salicylsulphuric acid, salicin, salicylamide, salsalate, sulindac, suprofen, suxibutazone, tamoxifen, tenoxicam, tiaprofenic acid, tiaramide, ticlopridine, tinoridine, tolfenamic acid, tolmetin, tropesin, xenbucin, ximoprofen, zaltoprofen, zomepirac, tomoxiprol, zafirlukast and cyclosporine;
(iii) an antineoplastic subunit derived from the antineoplastic compounds selected from bicaluatnide, estramustine phosphate, flutamide, mechlorethamine, thiotepa, ifosfamide, hydroxyurea, bleomycin, paclitaxel, lomustine, irinotecan, methotrexate, vinorelbine, anastrazole, floxuridine, melphalan, vincristine, vinblastine, mitomycin, nandrolone, goserelin, leuprolide, triptorelin, aminogluthetemide, mitotane, cisplatine, chlorambucil, pentostatin, cladribine, busulfan, etoposide, mitoxantrone, idarubicin, cyclophosphamide, mercaptopurine, thioguanine, cytarbine, cyclophosphamide, doxorubicin, daunoribicin, teniposide, and tamoxifen; and
(iv) an antiviral subunit derived from the anti-viral compounds selecting from aciclovir, lamivudine, ritonavir, indinavir, nevirapine, zidovudine, amprenavir, ribavirin and adamantane;
provided that when V is a steroid or non-steroidal anti-inflammatory subunit, L is a peptide; and
L is a linker molecule to which each of M and V are covalently linked.

* * * * *

UNITED STATES PATENT AND TRADEMARK OFFICE
CERTIFICATE OF CORRECTION

PATENT NO. : 7,157,433 B2
APPLICATION NO. : 10/616046
DATED : January 2, 2007
INVENTOR(S) : Mercep et al.

It is certified that error appears in the above-identified patent and that said Letters Patent is hereby corrected as shown below:

On the Title page:

Item (54) should read as follows:

(54) -- COMPOUNDS, COMPOSITIONS AS CARRIERS FOR STEROID/NONSTEROID ANTI-INFLAMMATORY, ANTINEOPLASTIC AND ANTIVIRAL ACTIVE MOLECULES --

Claim 2 (Column 57, Line 34) should read as follows:

-- $R^{12}$ is hydrogen or a group that with O–$R^{11}$ group and --

Claim 2 (Column 59, Line 13) should read as follows:

-- phosphate, flutamide, mechlorethamine, thiotepa, ifos- --

Claim 3 (Column 59, Lines 34-36) should read as follows:
    -- A and B are methyl;
    ~~B is hydrogen;~~
    E is hydrogen; --

Claim 3 (Column 60, Line 7) should read as follows:

-- C/4" carbon atom forms a >C=O or epoxy group; --

Claim 4 (Column 60, Line 25) should read as follows:

-- $X^2$ is –NHC(O)–; --

Signed and Sealed this
Third Day of July, 2012

David J. Kappos
*Director of the United States Patent and Trademark Office*

The Formula of Claim 15 (Columns 65-66, Lines 1-20) should read as follows:
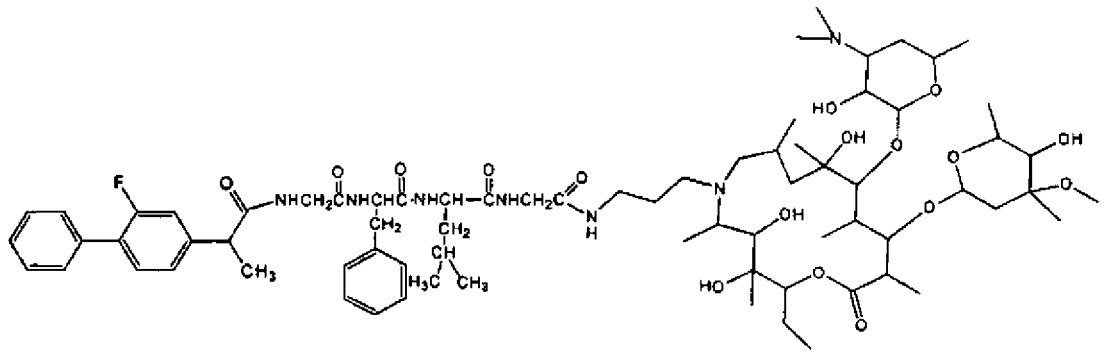
--
The Formula of Claim 17 (Columns 65-66, Lines 40-67) should read as follows:
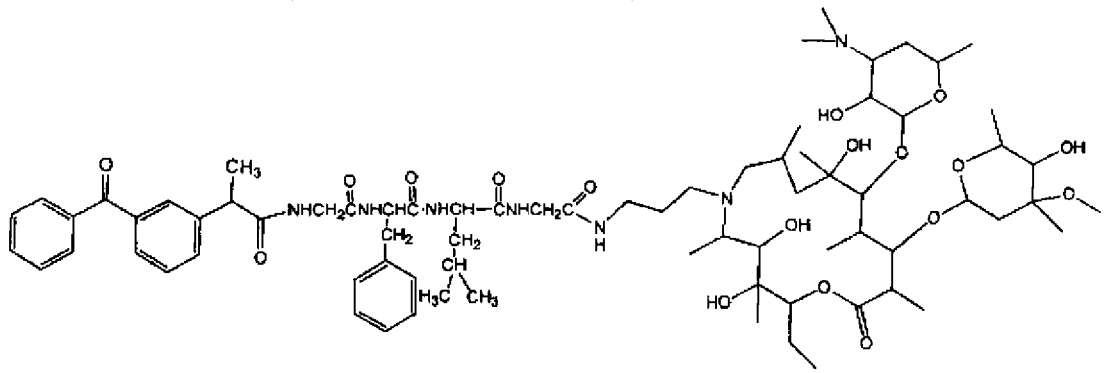
--
The Formula of Claim 28 (Column 75, Lines 1-44) should read as follows:
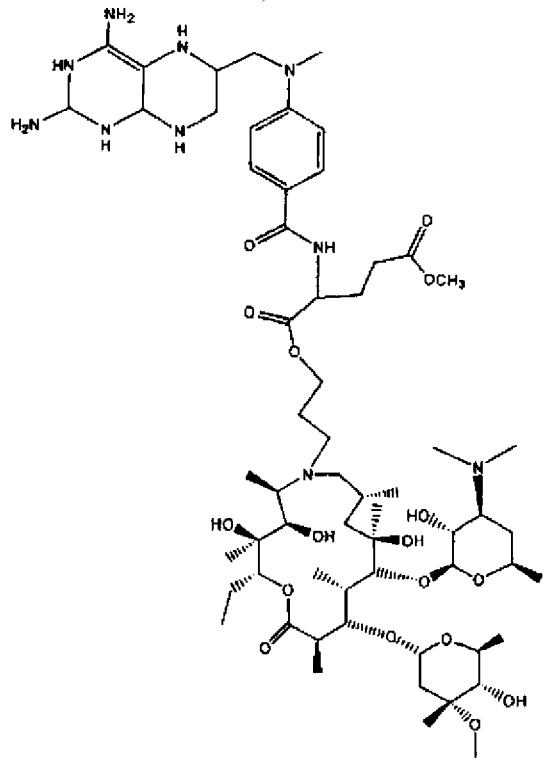
--

The Formula of Claim 29 (Column 75, Line 46) and (Column 76, Lines 1-22) should read as follows:

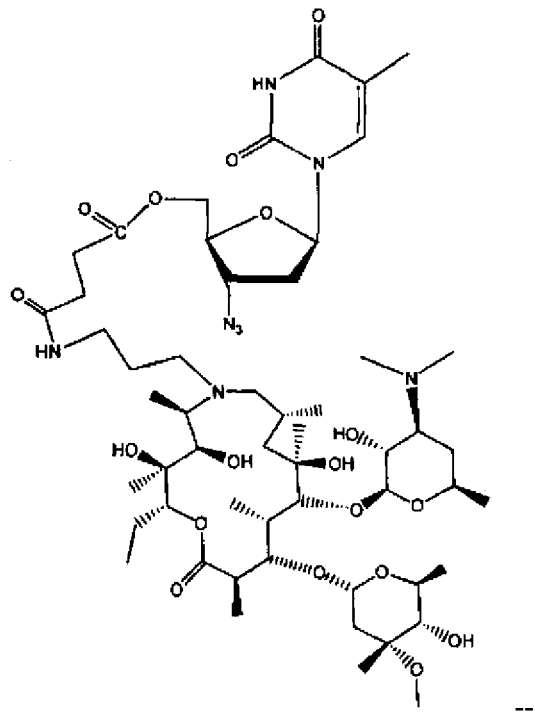

Claim 30 (Column 77, Line 29) should read as follows:

-- $R^{3'}$ is hydrogen or methyl; --

Claim 30 (Column 80, Line 40) should read as follows:

-- amino group of the compound represented by --

Claim 37 (Column 84, Line 26) should read as follows:

-- $R^j$ is hydrogen or halogen; and (ii) a non-steroidal anti- --

Claim 48 (Column 87, Line 22) should read as follows:

-- cyclosporine. --

Claim 61 (Column 89, Line 56) should read as follows:

-- M is linked to L at Z. --

Claim 63 (Column 90, Line 61) should read as follows:

-- $R^{3'}$ is hydrogen or methyl; --

CERTIFICATE OF CORRECTION (continued)
U.S. Pat. No. 7,157,433 B2

Claim 64 (Column 93, Line 34) should read as follows:

-- $R^{3'}$ is hydrogen or methyl; --

Claim 64 (Column 93, Line 65) should read as follows:

-- inflammatory steroid subunit derived from a steroid selected from --

Claim 64 (Column 94, Line 4) should read as follows:

-- thylprednisolone, triamcinolone, alclometasone, --

Claim 64 (Column 94, Lines 8-9) should read as follows:

-- rolone and dichlorisone, fluperinidene, fluticasone, halcinonide, meprednisone, methylprednisolone, --

Claim 64 (Column 94, Line 11) should read as follows:

-- triamincinolone, and acid derivatives thereof; --

UNITED STATES PATENT AND TRADEMARK OFFICE
CERTIFICATE OF CORRECTION

| | | |
|---|---|---|
| PATENT NO. | : 7,157,433 B2 | Page 1 of 4 |
| APPLICATION NO. | : 10/616046 | |
| DATED | : January 2, 2007 | |
| INVENTOR(S) | : Mercep et al. | |

It is certified that error appears in the above-identified patent and that said Letters Patent is hereby corrected as shown below:

<u>On the Title page, Item (54) and at Column 1, lines 1-4, Title</u> should read as follows:

-- COMPOUNDS, COMPOSITIONS AS
CARRIERS FOR STEROID/NONSTEROID
ANTI-INFLAMMATORY, ANTINEOPLASTIC
AND ANTIVIRAL ACTIVE MOLECULES --

Claim 2 (Column 57, Line 34) should read as follows:

-- $R^{12}$ is hydrogen or a group that with O–$R^{11}$ group and --

Claim 2 (Column 59, Line 13) should read as follows:

-- phosphate, flutamide, mechlorethamine, thiotepa, ifos- --

Claim 3 (Column 59, Lines 34-36) should read as follows:

-- A and B are methyl;
~~B is hydrogen;~~
E is hydrogen; --

Claim 3 (Column 60, Line 7) should read as follows:

-- C/4" carbon atom forms a >C=O or epoxy group; --

This certificate supersedes the Certificate of Correction issued July 3, 2003.

Signed and Sealed this
Fourteenth Day of August, 2012

David J. Kappos
*Director of the United States Patent and Trademark Office*

CERTIFICATE OF CORRECTION (continued)
U.S. Pat. No. 7,157,433 B2

Claim 4 (Column 60, Line 25) should read as follows:

-- $X^2$ is –NHC(O)–; --

The Formula of Claim 15 (Columns 65-66, Lines 1-20) should read as follows:

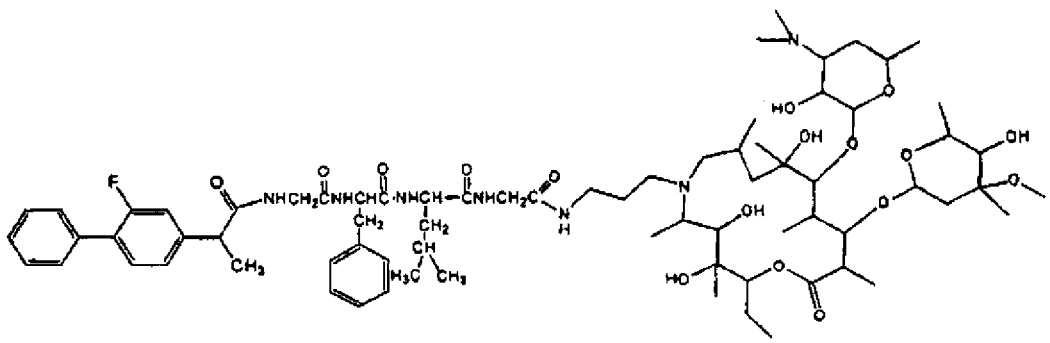

--                                                                                           --

The Formula of Claim 17 (Columns 65-66, Lines 40-67) should read as follows:

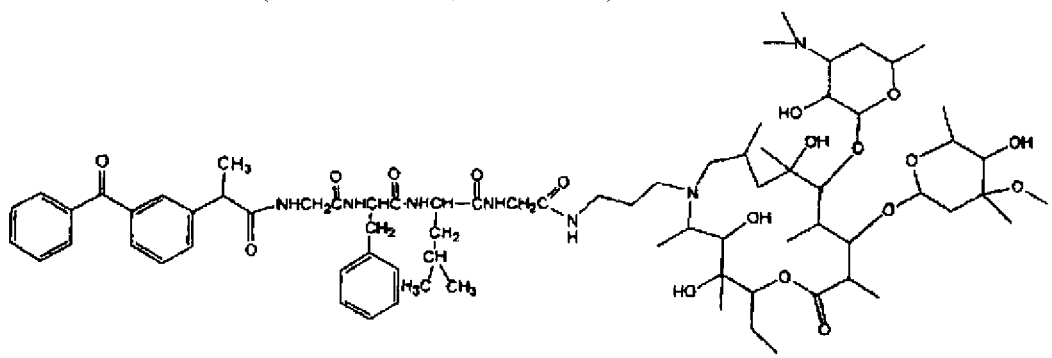

--                                                                                           --

CERTIFICATE OF CORRECTION (continued)
U.S. Pat. No. 7,157,433 B2

The Formula of Claim 28 (Column 75, Lines 1-44) should read as follows:

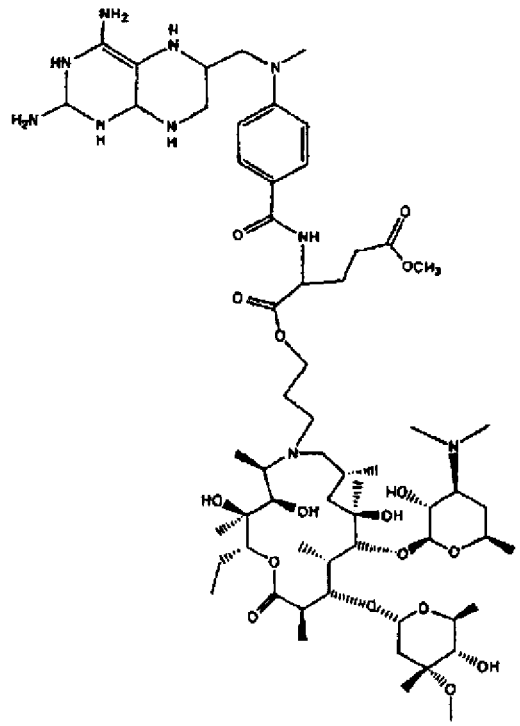

--                                                                   --

The Formula of Claim 29 (Column 75, Line 46) and (Column 76, Lines 1-22) should read as follows:

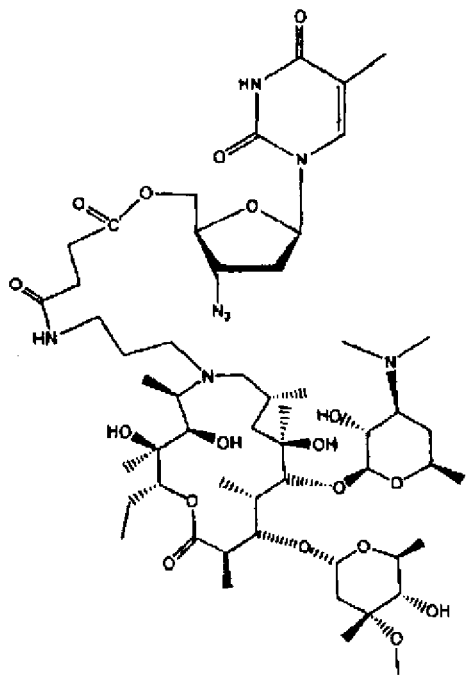

--                                                                   --

Claim 30 (Column 77, Line 29) should read as follows:

-- $R^{3'}$ is hydrogen or methyl; --

Claim 30 (Column 80, Line 40) should read as follows:

-- amino group of the compound represented by --

Claim 37 (Column 84, Line 26) should read as follows:

-- $R^j$ is hydrogen or halogen; and (ii) a non-steroidal anti- --

Claim 48 (Column 87, Line 22) should read as follows:

-- cyclosporine. --

Claim 61 (Column 89, Line 56) should read as follows:

-- M is linked to L at Z. --

Claim 63 (Column 90, Line 61) should read as follows:

-- $R^{3'}$ is hydrogen or methyl; --

Claim 64 (Column 93, Line 34) should read as follows:

-- $R^{3'}$ is hydrogen or methyl; --

Claim 64 (Column 93, Line 65) should read as follows:

-- inflammatory steroid subunit derived from a steroid selected from --

Claim 64 (Column 94, Line 4) should read as follows:

-- thylprednisolone, triamcinolone, alclometasone, --

Claim 64 (Column 94, Lines 8-9) should read as follows:

-- rolone and dichlorisone, fluperinidene, fluticasone, halcinonide, meprednisone, methylprednisolone, --

Claim 64 (Column 94, Line 11) should read as follows:

-- triamincinolone, and acid derivatives thereof; --